United States Patent
Scharp et al.

(10) Patent No.: US 7,427,415 B2
(45) Date of Patent: Sep. 23, 2008

(54) IMPLANTATION OF ENCAPSULATED BIOLOGICAL MATERIALS FOR TREATING DISEASES

(75) Inventors: David Scharp, Mission Viejo, CA (US); Paul Latta, Irvine, CA (US); Chengyun Yue, Irvine, CA (US); Xiaojie Yu, Irvine, CA (US); Jeffrey Alan Hubbell, Morges (CH)

(73) Assignee: Novocell, Inc., San Diego, CA (US)

( * ) Notice: Subject to any disclaimer, the term of this patent is extended or adjusted under 35 U.S.C. 154(b) by 712 days.

(21) Appl. No.: 10/684,859

(22) Filed: Oct. 14, 2003

(65) Prior Publication Data

US 2004/0136971 A1    Jul. 15, 2004

Related U.S. Application Data

(60) Provisional application No. 60/419,015, filed on Oct. 11, 2002.

(51) Int. Cl.
*A61K 9/16* (2006.01)

(52) U.S. Cl. .................. 424/497; 424/489; 424/490

(58) Field of Classification Search .................. None
See application file for complete search history.

(56) References Cited

U.S. PATENT DOCUMENTS 5,232,984 A    8/1993    Hubbell et al.

(Continued)

FOREIGN PATENT DOCUMENTS

AT    154242T T    6/1997

(Continued)

OTHER PUBLICATIONS

Gu, Y., et al., 2001, Development of a New Method to Induce Angiogenesis at Subcutaneous Site of Streptozotocin- Induced Diabetic Rats for Islet Transplantation, *Cell Transplantation*, 10, 453-457.

(Continued)

*Primary Examiner*—Carlos Azpuru
(74) *Attorney, Agent, or Firm*—Knobbe, Martens, Olson & Bear, LLP

(57) ABSTRACT

The present invention relates to compositions and methods of treating a disease, such as diabetes, by implanting encapsulated biological material into a patient in need of treatment. This invention provides for the placement of biocompatible coating materials around biological materials using photopolymerization while maintaining the pre-encapsulation status of the biological materials. Several methods are presented to accomplish coating several different types of biological materials. The coatings can be placed directly onto the surface of the biological materials or onto the surface of other coating materials that hold the biological materials. The components of the polymerization reactions that produce the coatings can include natural and synthetic polymers, macromers, accelerants, cocatalysts, photoinitiators, and radiation. This invention also provides methods of utilizing these encapsulated biological materials to treat different human and animal diseases or disorders by implanting them into several areas in the body including the subcutaneous site. The coating materials can be manipulated to provide different degrees of biocompatibility, protein diffusivity characteristics, strength, and biodegradability to optimize the delivery of biological materials from the encapsulated implant to the host recipient while protecting the encapsulated biological materials from destruction by the host inflammatory and immune protective mechanisms without requiring long-term anti-inflammatory or anti-immune treatment of the host.

36 Claims, 33 Drawing Sheets

A

B

U.S. PATENT DOCUMENTS

| Patent No. | | Date | Inventor |
|---|---|---|---|
| 5,334,640 | A | 8/1994 | Desai et al. |
| 5,380,536 | A | 1/1995 | Hubbell et al. |
| 5,410,016 | A | 4/1995 | Hubbell et al. |
| 5,462,990 | A | 10/1995 | Hubbell et al. |
| 5,529,914 | A | 6/1996 | Hubbell et al. |
| 5,545,423 | A | 8/1996 | Soon-Shiong et al. |
| 5,550,178 | A | 8/1996 | Desai et al. |
| 5,567,435 | A | 10/1996 | Hubbell et al. |
| 5,573,934 | A | 11/1996 | Hubbell et al. |
| 5,578,442 | A | 11/1996 | Desai et al. |
| 5,626,863 | A | 5/1997 | Hubbell et al. |
| 5,627,233 | A | 5/1997 | Hubbell et al. |
| 5,700,848 | A | 12/1997 | Soon-Shiong et al. |
| 5,705,270 | A | 1/1998 | Soon-Shiong et al. |
| 5,759,578 | A | 6/1998 | Soon-Shiong et al. |
| 5,788,988 | A | 8/1998 | Soon-Shiong et al. |
| 5,801,033 | A | 9/1998 | Hubbell et al. |
| 5,820,882 | A | 10/1998 | Hubbell et al. |
| 5,834,274 | A * | 11/1998 | Hubbell et al. ............... 435/177 |
| 5,834,556 | A * | 11/1998 | Desai et al. ................. 525/54.1 |
| 5,837,747 | A | 11/1998 | Soon-Shiong et al. |
| 5,843,743 | A | 12/1998 | Hubbell et al. |
| 5,846,530 | A | 12/1998 | Soon-Shiong et al. |
| 5,849,839 | A | 12/1998 | Hubbell et al. |
| 5,858,746 | A | 1/1999 | Hubbell et al. |
| 5,879,709 | A | 3/1999 | Soon-Shiong et al. |
| 5,986,043 | A | 11/1999 | Hubbell et al. |
| 6,007,833 | A | 12/1999 | Chudzik et al. |
| 6,060,582 | A | 5/2000 | Hubbell et al. |
| 6,077,698 | A | 6/2000 | Swan et al. |
| 6,156,345 | A | 12/2000 | Chudzik et al. |
| 6,231,892 | B1 | 5/2001 | Hubbell et al. |
| 6,258,870 | B1 | 7/2001 | Hubbell et al. |
| 6,306,922 | B1 | 10/2001 | Hubbell et al. |
| 6,326,201 | B1 | 12/2001 | Fung et al. |
| 6,368,612 | B1 | 4/2002 | Lanza et al. |
| 6,410,044 | B1 | 6/2002 | Chudzik et al. |
| 6,495,161 | B1 | 12/2002 | Soon-Shiong et al. |
| 6,565,842 | B1 | 5/2003 | Sojomihardjo et al. |
| 6,602,975 | B2 | 8/2003 | Hubbell et al. |
| 6,603,040 | B1 | 8/2003 | Swan et al. |
| 2002/0058318 | A1 | 5/2002 | Hubbell et al. |
| 2002/0091229 | A1 | 7/2002 | Hubbell et al. |
| 2002/0155598 | A1 | 10/2002 | Kerr-Conte et al. |
| 2003/0031697 | A1 | 2/2003 | Chudzik et al. |
| 2003/0087985 | A1 | 5/2003 | Hubbell et al. |

FOREIGN PATENT DOCUMENTS

| | | | |
|---|---|---|---|
| AT | 197125T | T | 11/2000 |
| AU | 8755791 | A | 5/1992 |
| AU | 3124793 | A | 6/1993 |
| AU | 3780993 | A | 9/1993 |
| AU | 3735393 | A | 10/1993 |
| AU | 7967994 | A | 5/1995 |
| AU | 673160 | B2 | 10/1996 |
| AU | 683209 | B2 | 11/1997 |
| AU | 683312 | B2 | 11/1997 |
| BR | 9306041 | A | 11/1997 |
| BR | 9306038 | A | 1/1998 |
| CA | 2121129 | A1 | 5/1993 |
| CA | 2117584 | A1 | 9/1993 |
| CA | 2117588 | A1 | 9/1993 |
| CA | 2173317 | A1 | 4/1995 |
| CA | 2117588 | C | 8/1998 |
| CA | 2117584 | C | 9/1998 |
| DE | 69126535D | D1 | 7/1997 |
| DE | 69126535T | T2 | 9/1997 |
| DE | 69425577D | D1 | 9/2000 |
| DE | 69329594D | D1 | 11/2000 |
| DE | 69425577T | T2 | 4/2001 |
| DE | 69329594T | T2 | 5/2001 |
| DK | 627911T | T3 | 11/2000 |
| DK | 722470T | T3 | 12/2000 |
| EP | 0553195 | A1 | 8/1993 |
| EP | 0553195 | A4 | 9/1993 |
| EP | 0610441 | A1 | 8/1994 |
| EP | 0627911 | A1 | 12/1994 |
| EP | 0627912 | A1 | 12/1994 |
| EP | 0627911 | A4 | 7/1995 |
| EP | 0627912 | A4 | 7/1995 |
| EP | 0610441 | A4 | 1/1996 |
| EP | 0722470 | A1 | 7/1996 |
| EP | 0553195 | B1 | 6/1997 |
| EP | 0722470 | B1 | 8/2000 |
| EP | 0627911 | B1 | 10/2000 |
| ES | 210472T | T3 | 10/1997 |
| ES | 2152334T | T3 | 2/2001 |
| ES | 2153378T | T3 | 3/2001 |
| GR | 3034767T | T3 | 2/2001 |
| GR | 3035172T | T3 | 4/2001 |
| JP | 7503943T | T | 4/1995 |
| JP | 7506961T | T | 8/1995 |
| JP | 7507056T | T | 8/1995 |
| JP | 9506012T | T | 6/1997 |
| JP | 11502552T | T | 3/1999 |
| JP | 3011767B2 | B2 | 2/2000 |
| JP | 3011768B2 | B2 | 2/2000 |
| JP | 2002514235T | T | 5/2002 |
| KR | 266912 | B1 | 12/2000 |
| NZ | 251039 | A | 3/1996 |
| NZ | 249770 | A | 9/1996 |
| PT | 722470T | T | 11/2000 |
| PT | 627911T | T | 4/2001 |
| WO | WO9206678 | A1 | 4/1992 |
| WO | WO9309176 | A2 | 5/1993 |
| WO | WO9309176 | A3 | 7/1993 |
| WO | WO9316687 | A1 | 9/1993 |
| WO | WO9317669 | A1 | 9/1993 |
| WO | WO9509883 | A1 | 4/1995 |
| WO | WO9629370 | A2 | 9/1996 |
| WO | WO9629370 | A3 | 11/1996 |
| WO | WO 00/09666 | | 2/2000 |
| WO | WO 00/53159 | | 9/2000 |
| WO | WO 03/102171 | | 12/2003 |

OTHER PUBLICATIONS

Kawakami, Y. et al., 2000, Modified Subcutaneous Tissue with Neovascularization is Useful as the Site for Pancreatic Islet Transplantation, *Cell Transplantation*, 9, 729-732.

Kawakami, Y., et al., 2001, Successful Subcutaneous Pancreatic Islet Transplantation Using an Angiogeneic Growth Factor-Releasing Device, *Pancreas*, 23(4), 375-381.

Wang, W., et al., 2003, Subcutaneous Transplantation of Macroencapsulated Procine Pancreatic Endocrine Cells Normalizes Hyperglycemia in Diabetic Mice, *Transplantation*, 76(2), 290-296.

Bonner-Weir, et al. "In Vitro Cultivation of Human Islets from Expanded Ductal Tissue," *Proceedings of the National Academy of Sciences of USA*, vol. 97, No. 14, pp. 7999-8004, Jul. 5, 2000.

Gu, et al. "Transitional Cells in the Regenerating Pancreas," *Development*, vol. 120, pp. 1873-1881, 1994.

* cited by examiner

A

B

| Score | Histology |
|---|---|
| 1 |  |
| 2 |  |
| 4 |  |

IMPLANTATION OF ENCAPSULATED BIOLOGICAL MATERIALS FOR TREATING DISEASES

RELATED APPLICATIONS

This application claims priority to U.S. provisional application No. 60/419,015, filed Oct. 11, 2002 which is incorporated herein by reference in its entirety.

FIELD OF THE INVENTION

The present invention relates to compositions and methods of treating a disease, such as diabetes, by implanting encapsulated biological material into a patient in need of treatment.

BACKGROUND OF THE INVENTION

Diabetes mellitus is a disease caused by the loss of the ability to transport glucose into the cells of the body, because of either a lack insulin production or diminished insulin response. In a healthy person, minute elevations in blood glucose stimulate the production and secretion of insulin, the role of which is to increase glucose uptake into cells, returning the blood glucose to the optimal level. Insulin stimulates liver and skeletal muscle cells to take up glucose from the blood and convert it into glycogen, an energy storage molecule. It also stimulates skeletal muscle fibers to take up amino acids from the blood and convert them into protein, and it acts on adipose (fat) cells to stimulate the synthesis of fat. In diabetes, glucose saturates the blood stream, but it cannot be transported into the cells where it is needed and utilized. As a result, the cells of the body are starved of needed energy, which leads to the wasted appearance of many patients with poorly controlled insulin-dependent diabetes.

Prior to the discovery of insulin and its use as a treatment for diabetes, the only available treatment was starvation followed predictably by death. Death still occurs today with insulin treatment from over dosage of insulin, which results in extreme hypoglycemia and coma followed by death unless reversed by someone who can quickly get glucose into the patient. Also, death still occurs from major under dosage of insulin, which leads to hyperglycemia and ketoacidosis that can result in coma and death if not properly and urgently treated.

While diabetes is not commonly a fatal disease thanks to the treatments available to diabetics today, none of the standard treatments can replace the body's minute-to-minute production of insulin and precise control of glucose metabolism. Therefore, the average blood glucose levels in diabetics generally remain too high. The chronically elevated blood glucose levels cause a number of long-term complications. Diabetes is the leading cause of new blindness, renal failure, premature development of heart disease or stroke, gangrene and amputation, and impotence. It decreases the sufferer's overall life expectancy by one to two decades.

Diabetes mellitus is one of the most common chronic diseases in the world. In the United States, diabetes affects approximately 16 million people—more than 12% of the adult population over 45. The number of new cases is increasing by about 150,000 per year. In addition to those with clinical diabetes, there are approximately 20 million people showing symptoms of abnormal glucose tolerance. These people are borderline diabetics, midway between those who are normal and those who are clearly diabetic. Many of them will develop diabetes in time and some estimates of the potential number of diabetics are as high as 36 million or 25-30% of the adult population over 45 years.

Diabetes and its complications have a major socioeconomic impact on modem society. Of the approximately $700 billion dollars spent on healthcare in the US today, roughly $100 billion is spent to treat diabetes and its complications. Since the incidence of diabetes is rising, the costs of diabetes care will occupy an ever-increasing fraction of total healthcare expenditures unless steps are taken promptly to meet the challenge. The medical, emotional and financial toll of diabetes is enormous, and increase as the numbers of those suffering from diabetes grows.

Diabetes mellitus can be subdivided into two distinct types: Type 1 diabetes and Type 2 diabetes. Type 1 diabetes is characterized by little or no circulating insulin, and it most commonly appears in childhood or early adolescence. There is a genetic predisposition for Type 1 diabetes. It is caused by the destruction of the insulin-producing beta cells in the islets of Langerhans; which are scattered throughout the pancreas, an elongated gland located transversely behind the stomach. The beta cells are attacked by an autoimmune reaction initiated by some as yet unidentified environmental event. Possibly a viral infection or noninfectious agent (a toxin or a food) triggers the immune system to react to and destroy the patient's beta cells in the pancreas. The pathogenic sequence of events leading to Type 1 diabetes is thought to consist of several steps. First, it is believed that genetic susceptibility is an underlying requirement for the initiation of the pathogenic process. Secondly, an environmental insult mediated by a virus or noninfectious pathogen in food triggers the third step, the inflammatory response in the pancreatic islets (insulitis). The fourth step is an alteration or transformation of the beta cells such that they are no longer recognized as "self" by the immune system, but rather seen as foreign cells or "nonself". The last step is the development of a full-blown immune response directed against the "targeted" beta cells, during which cell-mediated immune mechanisms cooperate with cytotoxic antibodies in the destruction of the insulin-producing beta cells. Despite this immune attack, for a period, the production of new beta cells is fast enough to stay ahead of the destruction by the immune system and a sufficient number of beta cells are present to control blood glucose levels. However, the number of beta cells gradually declines. When the number of beta cells drops to a critical level (10% of normal), blood glucose levels no longer can be controlled and progression to total insulin production failure is almost inevitable. It is thought that the regeneration of beta cells continues for a few years, even after functional insulin production ceases, but that the cells are destroyed as they develop to maturity.

To reduce their susceptibility to both the acute and chronic complications of diabetes, people with Type 1 diabetes must take multiple insulin injections daily and test their blood sugar multiple times per day by pricking their fingers for blood. They then have to decide how much insulin to take based on the food eaten and level of physical activity, amount of stress, and existence of any illness over the next few hours. The multiple daily injections of insulin do not adequately mimic the body's minute-to-minute production of insulin and precise control of glucose metabolism. Blood sugar levels are usually higher than normal, causing complications that include blindness, heart attack, kidney failure, stroke, nerve damage, and amputations. Even with insulin, the average life expectancy of a diabetic is 15-20 years less than a healthy person.

Type 2 diabetes usually appears in middle age or later, and particularly affects those who are overweight. Over the past few years, however, the incidence of Type 2 diabetes mellitus in young adults has increased dramatically. In the last several years, the age of onset for Type 2 diabetes in obese people has dropped from 40 years to 30 years. These are the new younger victims of this disease. In Type 2 diabetes, the body's cells that normally require insulin lose their sensitivity and fail to respond to insulin normally. This insulin resistance may be overcome for many years by extra insulin production by the pancreatic beta cells. Eventually, however, the beta cells are gradually exhausted because they have to produce large amounts of excess insulin due to the elevated blood glucose levels. Ultimately, the overworked beta cells die and insulin secretion fails, bringing with it a concomitant rise in blood glucose to sufficient levels that it can only be controlled by exogenous insulin injections. High blood pressure and abnormal cholesterol levels usually accompany Type 2 diabetes. These conditions, together with high blood sugar, increase the risk of heart attack, stroke, and circulatory blockages in the legs leading to amputation. Drugs to treat Type 2 diabetes include some that act to reduce glucose absorption from the gut or glucose production by the liver, others that reduce the formation of more glucose by the liver and muscle cells, and others that stimulate the beta cells directly to produce more insulin. However, high levels of glucose are toxic to beta cells, causing a progressive decline of function and cell death. Consequently, many patients with Type 2 diabetes eventually need exogenous insulin.

Another form of diabetes is called Maturity Onset Diabetes of the Young (MODY). This form of diabetes is due to one of several genetic errors in insulin-producing cells that restrict their ability to process the glucose that enters via special glucose receptors. Beta cells in patients with MODY cannot produce insulin correctly in response to glucose, which results in hyperglycemia. The patients treatment eventually leads to the requirement for insulin injections.

The currently available medical treatments for insulin-dependent diabetes are limited to insulin administration and pancreas transplantation with either whole pancreata or pancreatic segments.

Insulin therapy is by far more prevalent than pancreas transplantation. Insulin administration is conventionally either by a few blood glucose measurements and subcutaneous injections, intensively by multiple blood glucose measurements and through multiple subcutaneous injections of insulin, or by continuous subcutaneous injections of insulin with a pump. Conventional insulin therapy involves the administration of one or two injections a day of intermediate-acting insulin with or without the addition of small amounts of regular insulin. The intensive insulin therapy involves multiple administration of intermediate- or long-acting insulin throughout the day together with regular or short-acting insulin prior to each meal. Continuous subcutaneous insulin infusion involves the use of a small battery-driven pump that delivers insulin subcutaneously to the abdominal wall, usually through a 27-gauge butterfly needle. This treatment modality has insulin delivered at a basal rate continuously throughout the day and night, with increased rates programmed prior to meals. In each of these methods, the patient is required to frequently monitor his or her blood glucose levels and, if necessary, adjust the insulin dose. However, controlling blood sugar is not simple. Despite rigorous attention to maintaining a healthy diet, exercise regimen, and always injecting the proper amount of insulin, many other factors can adversely affect a person's blood-sugar including stress, hormonal changes, periods of growth, illness, infection and fatigue. People with Type 1 diabetes must constantly be prepared for life threatening hypoglycemic (low blood sugar) and hyperglycemic (high blood sugar) reactions. Insulin-dependent diabetes is a life threatening disease, which requires never-ending vigilance.

In contrast to insulin administration, whole pancreas transplantation or transplantation of segments of the pancreas is known to eliminate the elevated glucose values by regulating insulin release from the new pancreas in diabetic patients. Histologically, the pancreas is composed of three types of functional cells; a) exocrine cells that secrete their enzymes into a small duct, b) ductal cells that carry the enzymes to the gut, and c) endocrine cells that secrete their hormones into the bloodstream. The exocrine portion is organized into numerous small glands (acini) containing columnar to pyramidal epithelial cells known as acinar cells. Acinar cells comprise approximately 80% of the pancreatic cells and secrete into the pancreatic duct system digestive enzymes, such as, amylases, lipases, phospholipases, trypsin, chymotrypsin, aminopeptidases, elastase and various other proteins. Approximately 1.5 and 3 liters of alkaline fluid are released per day into the common bile duct to aid digestion.

The pancreatic duct system consists of an intricate, tributary-like network of interconnecting ducts that drain each secretory acinus, draining into progressively larger ducts, and ultimately draining into the main pancreatic duct. The lining epithelium of the pancreatic duct system consists of duct cells. Approximately 10% of the pancreas cells is duct cells. Duct cell morphology ranges from cuboidal in the fine radicles draining the secretory acini to tall, columnar, mucus secreting cells in the main ductal system.

Hormone producing islets are scattered throughout the pancreas and secrete their hormones into the bloodstream, rather than ducts. Islets are richly vascularized. Islets comprise only 1-2% of the pancreas, but receive about 10 to 15% of the pancreatic blood flow. There are three major cell types in the islets, each of which produces a different endocrine product: alpha cells secrete the hormone glucagon (glucose release); beta cells produce insulin (glucose use and storage) and are the most abundant of the islet cells; and delta cells secrete the hormone somatostatin (inhibits release of other hormones). These cell types are not randomly distributed within an islet. The beta cells are located in the central portion of the islet and are surrounded by an outer layer of alpha and delta cells. Besides insulin, glucagon and somatostatin, gastrin and Vasoactive Intestinal Peptide (VIP) have been identified as products of pancreatic islets cells.

Pancreas transplantation is usually only performed when kidney transplantation is required, which makes pancreas-only transplantations relatively infrequent operations. Although pancreas transplants are very successful in helping people with insulin-dependent diabetes improve their blood sugar control without the need for insulin injections and reduce their long-term complications, there are a number of drawbacks to whole pancreas transplants. Most importantly, getting a pancreas transplant involves a major operation and requires the use of life-long immune suppressant drugs to prevent the body's immune system from destroying the pancreas. The pancreas is destroyed in a manner of days without these drugs. Some risks in taking these immuno-suppressive drugs are the increased incidence of infections and tumors that can be life threatening in their own right. The risks inherent in the operative procedure, the requirement for life-long immunosuppression of the patient to prevent rejection of the transplant, and the morbidity and mortality rate associated with this invasive procedure, illustrate the serious disadvantages associated with whole pancreas transplantation for the treatment of diabetes. Thus, an alternative to insulin injections or pancreas transplantation would fulfill a great public health need.

Islet transplants are much simpler (and safer) procedures than whole pancreas transplants and can achieve the same effect by replacing the destroyed beta cells. As discussed above, when there are insufficient numbers of beta cells, or insufficient insulin secretion, regardless of the underlying reason, diabetes results. Reconstituting the islet beta cells in a diabetic patient to a number sufficient to restore normal glucose-responsive insulin production would solve the problems associated with both insulin injection and major organ transplantation. Microencapsulation and implantation of islet cells into diabetic patients holds promise for treatment of those with diabetes.

Encapsulation of cells for the potential of treating a number of diseases and disorders has been discussed in the literature. The concept was suggested as early as 100 years ago, but little work was done prior to the 1950's when immunologists began using encapsulated cells with membrane devices to separate the cells from the host to better understand the different aspects of the immune system. Research on implantation was underway in the 1970's and 1980's with the first review written in 1984. Several additional reviews have been written since then explaining the different approaches and types of devices under development. Cell encapsulation technology has potential applications in many areas of medicine. For example, some important potential applications are treatment of diabetes (Goosen, M. F. A., et al. (1985) Biotechnology and Bioengineering, 27:146), production of biologically important chemicals (Omata, T., et al. (1979) "Transformation of Steroids by Gel-Entrapped Nacardia rhodocrous Cells in Organic Solvent" Eur. J. Appl. Microbiol. Biotechnol. 8:143-155), and evaluation of anti-human immunodeficiency virus drugs (McMahon, J., et al. (1990) J. Nat. Cancer Inst., 82(22) 1761-1765).

There are three main types of encapsulated devices, which can best be categorized by describing the form of encapsulation. The three categories are a] macrodevices, b] microcapsules, and c] conformal coatings.

Macrodevices are larger devices containing membranes in the form of sheets or tubes for permselectivity and usually supporting structures. They contain one or several compartments for the encapsulated cells. They are designed for implantation into extravascular or vascular sites. Some are designed to grow into the host to increase oxygen diffusion into these large devices. Others are designed to have no reaction by the host, thus increasing their ease of removal from different sites. There have been two major types of macrodevices developed: a] flat sheet and b] hollow fiber.

Among the flat sheet devices, one type (Baxter, Theracyte) is made of several layers for strength and has diffusion membranes between support structures with loading ports for replacing the cells. The other type is more simple in design. The device uses alginate based membranes and other supporting membranes to encapsulate islets within an alginate matrix between the sheets. The complex device is designed to grow into the body to increase diffusion of oxygen. Due to its relatively large size, there are few sites in the body able to accommodate it for the treatment of a disease like diabetes. Since it grows into the body and the contained cells are not expected to survive for more than a few years, multiple cell removals and reloadings of new cells is required for the long-term application of this device. It has proven quite difficult to flush and reload this type of device while at the same time maintaining the critical cell compartment distance for oxygen diffusion.

The second flat sheet style of device is designed to be an "all in/all out" device with little interaction with the host. For the diabetes product, it has been quite difficult to place this device into the intraperitoneal cavity of large animals, while maintaining its integrity. This has been due to the difficulty in securing it in the abdomen so that the intestines cannot cause it to move or wrinkle, which may damage or break the device.

The other major macrodevice type is the hollow fiber, made by extruding thermoplastic materials into hollow fibers. These hollow fibers can be made large enough to act as blood conduits. One model is designed to be fastened into the host's large blood vessels and the encapsulated cells are behind a permselective membrane within the device. This type has shown efficacy in large animal diabetic trials, but has been plagued by problems in the access to the vascular site. Both thrombosis and hemorrhage have complicated the development of this approach with it currently being abandoned as a clinically relevant product. Another model using hollow fibers is much smaller in diameter and designed to be used as an extravascular device. Due to low packing densities, the required cell mass for encapsulation causes the length of this type of hollow to approach many meters. Therefore, this approach was abandoned for treating diabetes since it was not clinically relevant. In addition, sealing the open ends of the fiber is not trivial and strength has been a problem depending upon the extravascular site.

The microcapsule was one of the first to offer potential clinical efficacy. Alginate microcapsules were used to encapsulate islets, which eliminated diabetes in rodents when implanted intraperitoneally. However, nearly 25 years have passed since these first reports without the ability to demonstrate clinical efficacy. One of the problems associated with microcapsules is their relatively large size in combination with low packing densities of cells, especially for the treatment of diabetes. Another is the use of alginate; an ionically crosslinked hydrogel dependent upon the calcium concentration for its degree of crosslinking. The permselectivity of pure alginate capsules has been difficult to control with the vast majority being wide open in terms of molecular weight cut-off. Varieties of positively charged crosslinked agents, such as polylysine, have been added as a second coating to provide permselectivity to the capsule. However, polylysine and most other similar molecules invite an inflammatory reaction requiring an additional third coating of alginate to reduce the host's response to the capsule. In addition, it has been difficult to produce very pure alginates that are not reactive within the host after implantation. Trying to reduce the size of the alginate microcapsules causes two major problems. First, the production of very large quantities of empty capsules without any cells. Second, the formation of smaller capsules results in poorly coated cells. There is no force to keep the contained cells within the center of the microcapsule, which causes the risk of incomplete coatings to go up exponentially with the decrease in the size of the capsules. Production of conformal coatings has not been demonstrated with alginate microcapsules.

The last category of cell encapsulation is conformal coating. A conformally coated cell aggregate is one that has a substantially uniform cell coating around the cell aggregate regardless of size or shape of the aggregate. This coating not only may be uniform in thickness, but it also may be uniform in the protective permselective nature of the coating that provides uniform immune protection. Furthermore, it may be uniform in strength and stability, thus preventing the coated material from being violated by the host's immune system.

An important aspect to the feasibility of using these various methods is the relevant size and implant site needed to obtain a physiological result of 15,000 IEQ/kg-BW. Injecting isolated islets into the Portal Vein requires 2-3 ml of pack cells.

A macro-device consisting of a flat sheet that is 1 islet thick (~500 μm) requires a surface area equivalent to 2 US dollar bills. A macro-device consisting of hollow fibers with a loading density of 5% would need 30 meters of fiber. Alginate microcapsules with an average diameter of 400-600 μm would need a volume of 50-170 ml. However, PEG conformal coating of islets which produces a 25-50 μm thick covering would only need a volume of 6-12 ml and could be injected into almost any area in the body.

The stringent requirements of encapsulating polymers for biocompatibility, chemical stability, immunoprotection and resistance to cellular overgrowth restrict the applicability of prior art methods of encapsulating cells and other biological materials. The membranes must be non-toxically produced in the presence of cells, with the qualities of being permselective, chemically stable, and very highly biocompatible.

Synthetic or natural materials intended to be exposed to biological fluids or tissues are broadly classified as biomaterials. These biomaterials are considered biocompatible if they produce a minimal or no adverse response in the body. For many uses of biomaterials, it is desirable that the interaction between the physiological environment and the material be minimized. For these uses, the material is considered "biocompatible" if there is minimal cellular growth on its surface subsequent to implantation, minimal inflammatory reaction, and no evidence of anaphylaxis during use. Thus, the material should neither elicit a specific humoral or cellular immune response nor a nonspecific foreign body response.

Materials that are successful in preventing all of the above responses are relatively rare. Biocompatibility is more a matter of degree rather than an absolute state. The first event occurring at the interface of any implant with surrounding biological fluids is protein adsorption (Andrade, J. D. et al. (1986) V. Adv. Polym. Sci., 79:1-63). In the case of materials of natural origin, it is conceivable that specific antibodies for that material exist in the repertoire of the immune defense mechanism of the host. In this case, a strong immune response can result. Most synthetic materials, however, do not elicit such a reaction. They can either activate the complement cascade and/or adsorb serum proteins, such as, cell adhesion molecules (CAMs), which mediate cell adhesion (Buck, C. A. et al. (1987) Ann. Rev. Cell Biol., 3:179-205).

Proteins can adsorb on almost any type of material. They have regions that are positively and/or negatively charged, as well as, hydrophilic and hydrophobic. Thus, they can interact with implanted material through any of these various regions, resulting in cellular proliferation at the implant surface. Complement fragments such as C3b can be immobilized on the implant surface and act as chemoattractants. They in turn can activate inflammatory cells, such as macrophages and neutrophils, and cause their adherence and activation on the implant. These cells attempt to degrade and digest the foreign material.

In the event that the implant is nondegradable and is too large to be ingested by large single activated macrophages, the inflammatory cells may undergo frustrated phagocytosis. Several such cells can combine to form foreign body giant cells. In this process, these cells release peroxides, hydrolytic enzymes, and chemoattractant and anaphylactic agents such as interleukins, which increase the severity of the reaction. They also induce the proliferation of fibroblasts on foreign surfaces.

Past approaches to enhancing biocompatibility of materials started with attempts at minimization of interfacial energy between the material and its aqueous surroundings. Similar interfacial tensions of the solid and liquid were expected to minimize the driving force for protein adsorption and this was expected to lead to reduced cell adhesion and thrombogenicity of the surface. For example, Amudeshwari et al. used collagen gels crosslinked in the presence of HEMA and MMA (Amudeswari, S., et al. (1986) J. Biomed. Mater. Res. 20:1103-1109). Desai and Hubbell showed a poly(HEMA)-MMA copolymer to be somewhat non-thrombogenic (Desai, N. P. et al. (1989) J. Biomaterials Sci., Polym. Ed., 1:123-146; Desai, N. P. et al. (1989) Polym. Materials Sci. Eng., 62:731).

Hubbell et al. (U.S. Pat. No. 5,529,914 and related patents) disclose methods for the formation of biocompatible membranes around biological materials using photopolymerization of water-soluble molecules. Each of these methods utilizes a polymerization system containing water-soluble macromers, polymerization using a photoinitiator (such as a dye), and radiation in the form of visible or long wavelength UV light.

Due to the inability of those of skill in the art to provide one or more important properties of successful cell encapsulation, none of the encapsulation technologies developed in the past have resulted in a clinical product. These properties can be broken down into the following categories:

Biocompatibility—The materials used to make an encapsulating device must not elicit a host response, which may cause a non-specific activation of the immune system by these materials alone. When considering immunoisolation, one must recognize that it will only work in the situation where there is no activation of the host immune cells to the materials. If there is activation of the host immune cells by the materials, then the responding immune cells will surround the device and attempt to destroy it. This process produces many cytokines that will certainly diffuse through the capsule and most likely destroy the encapsulated cells. Most devices tested to date have failed in part by their lack of biocompatibility in the host.

Permselectivity—There exists an important balance between having the largest pores as possible in the capsule surrounding the encapsulated cells to permit all the nutrients and waste products to pass through the capsule to permit optimal survival and function, while at the same time, the smallest pore size as possible in the capsule to keep all elements of the immune system away from the encapsulated cells to prevent degradation of the cells. Small pores capable of keeping out immune cytokines also cause the death of the encapsulated cells from a lack of diffusion of nutritional elements and waste products. The optimal cell encapsulation has an exact and consistent permselectivity, which allows maximal cell survival and function, as well as, provides isolation from the host immune response. Ideally, this encapsulation technology should offer the ability to select and change the pore size as required by the encapsulated cells and their function, as well as pore size variation based on whether the cells are allograft or xenograft cells.

Encapsulated Cell Viability and Function—The encapsulating materials should not exhibit cytotoxicity to the encapsulated cells either during the formation of the coatings or on an ongoing basis, otherwise the number of encapsulated cells will decrease and risk falling short of the number required for a therapeutically effective treatment of a disease or disorder.

Relevant Size—Many devices are of such a large size that the number of practical implantation sites in the host is limited. Another factor is the relative diffusion distance between the encapsulated cells and the host. The most critical diffusive agent for cell survival is oxygen. These diffusion distances should be minimal since the starting partial pressure of oxygen is in the range of 30-40 mm Hg at the tissue level in the body. There is little tolerance for a reduction in diffusive distances, due to the initially low oxygen partial pressure.

This would further lower the oxygen concentration to a point where the cells cannot adequately function or survive.

Cell Retrieval or Replacement—The encapsulating device should be retrievable, refillable, or biodegradable, allowing for replacement or replenishment of the cells. Many device designs have not considered the fact that encapsulated cells have a limited lifetime in the host and require regular replacement.

Therapeutic Effect—The implant should contain sufficient numbers of functional cells to have a therapeutic effect for the disease application in the host.

Clinical Relevance—The encapsulating cell device should have a total volume or size that allows it to be implanted in the least invasive or most physiologic site for function, which has a risk/benefit ratio below that faced by the host with the current disease or disorder.

Commercial Relevance—The encapsulating cell device should be able to meet the above requirements in order for it to be produced on an ongoing basis for the long-term treatment of the disease process for which it has been designed.

All of the above factors must be taken into consideration when evaluating a specific technique, method or product for use in implantation of islets to alleviate the effects of diabetes.

Transplantation of human islets with immunosuppression is done by injecting unencapsulated islets into the portal vein by direct injection percutaneously between the ribs, into the liver, and then the portal vein by fluoroscopic direction. Essentially all of the human islet transplants have been done by this technique, except for the first ones done by umbilical vein injection via a cutdown. A major risk of this procedure is the fact that injection of islets into the portal vein leads to increased portal venous pressures depending on the rate of infusion and the amount infused. Another risk has been elevated portal venous pressures from large volumes of injected islet tissues that are not sufficiently purified. This also leads to portal venous thrombosis as a complication of this procedure. As the interventional radiologist prepares to withdraw the catheter, a bolus of gelatin is left behind to prevent hemorrhaging from the injection site. Unfortunately, several patients have had bleeding episodes following this procedure.

In addition to injecting the islets into the portal vein, a few patients have had their islets injected into the body of the spleen. The spleen is more fragile than the liver so these injections were performed at the time of kidney transplantation at which time the splenic injection could be done as an open procedure. Freely injecting the islets into the peritoneal cavity has been performed in mouse transplants without difficulty. In using this site in larger animals or humans, it has been found that twice the number of islets is needed in the peritoneal cavity than required in the portal vein implants. If any rejection or inflammatory reactions occur, then adhesions tend to form between the loops of intestine, as well as, to the omentum. This reaction can lead to additional problems long term, such as, bowel obstruction. Thus, the ability to perform encapsulated islet implants into the subcutaneous site would significantly reduce the complications associated with these other sites.

Attempts at subcutaneous implantation of encapsulated islets have been unable to produce sustainable results in the treatment of diabetes, probably due to some or all of the scientific challenges described above. Tatarkiewicz et al. (Transplantation Proceedings 1998, 30, 479-480) discloses the implantation of rat islets, enclosed in tissue diffusion ported devices, subcutaneously in mice. Kawakami et al. (Cell Transplantation 1997 6, 5:541-545) implanted pancreatic beta cells, encapsulated in agarose-PSSa, subcutaneously in rats. Insulin secretion from the cells was maintained after transplantation. However, this study only examined subcutaneous implantation of the encapsulated islet cells over a one-week period. No evidence has been provided that the insulin secretion response of the cells could be maintained long term in a subcutaneous implant. Kawakami et al. (Transplantation 2002, 73,122-129) enclosed rat islets in an agarose/poly(styrene sulfonic acid) mixed gel and implanted the encapsulated cells into a prevascularized subcutaneous site. Stockley et al. (J. Lab. Clin. Med. 135:484-492) encapsulated allogenic MDCK cells engineered to secrete human growth hormone in alginate-poly-L-lysine-alginate and implanted them subcutaneously. The encapsulated cells of Stockley et al. can be estimated as having a diameter of approximately 1.5 mm, if it is assumed that the capsule volume used is 100 µl and this volume does not comprise components other than the encapsulated cells. Stockley provides no information about the actual volume of encapsulated cells that are applied. One of skill in the art would be unable to determine the desired volume of encapsulated cells needed to administer to a subject.

SUMMARY OF THE INVENTION

In one embodiment, the invention is directed to a composition for cellular therapy, which includes a plurality of encapsulating devices including a polyethylene glycol (PEG) coating, said PEG having a molecular weight between about 900 and about 3,000 Daltons; and a plurality of cells encapsulated in the encapsulating devices, wherein said composition has a cell density of at least about 100,000 cells/ml. In a preferred embodiment, the encapsulating devices are microcapsules. In a more preferred embodiment, the microcapsules are conformally coated cell aggregates. Preferably, the cell aggregates are pancreatic islets with a cell density which is at least about 6,000,000 cells/ml.

In a preferred embodiment, the cell is neurologic, cardiovascular, hepatic, endocrine, skin, hematopoietic, immune, neurosecretory, metabolic, systemic, or genetic. Preferably, the cell is autologous, allogeneic, xenogeneic or genetically-modified. In a most preferred embodiment, the cell is an insulin producing cell.

In another aspect, the invention is directed to a therapeutically effective composition which includes a plurality of encapsulating devices having an average diameter of less than 400 µm, where the encapsulating devices include encapsulated cells in an encapsulation material, and the composition comprises at least about 500,000 cells/ml. In a more preferred embodiment, the average diameter of the encapsulating device is less than 300 micron. In yet a more preferred embodiment, the average diameter of the encapsulating device is less than 200 micron. In yet a more preferred embodiment, the average diameter of the encapsulating device is less than 100 micron. And in yet a more preferred embodiment, the average diameter of the encapsulating device is less than 50 micron.

In yet another embodiment, the invention is directed to a therapeutically effective composition including a plurality of encapsulating devices having an average diameter of less than 400 µm, where the encapsulating devices include encapsulated cells in an encapsulation material, and the composition has a ratio of volume of encapsulating device to volume of cells of less than about 20:1. In a more preferred embodiment, the composition has a ratio of volume of encapsulating device to volume of cells of less than about 10:1. In a yet more preferred embodiment, the composition has a ratio of volume of encapsulating device to volume of cells of less than about 2:1.

In another embodiment, the invention is directed to using a therapeutic composition as described herein in a method which includes the step of implanting the composition into an implantation site in an animal in need of treatment for a disease or disorder.

In a preferred embodiment, the invention is directed to a method of using the therapeutic composition which includes encapsulating devices with a polyethylene glycol (PEG) coating having a molecular weight between 900 and 3,000 Daltons, where the composition has a cell density of at least about 100,000 cells/ml in a method which includes the step of implanting the composition into an implantation site in an animal in need of treatment for a disease or disorder. Preferably, the implanting is an injection.

In preferred embodiments, the disease or disorder is neurologic, cardiovascular, hepatic, endocrine, skin, hematopoietic, immune, neurosecretory, metabolic, systemic, or genetic. In a most preferred embodiment, the disease is an endocrine disease which is diabetes.

In a preferred embodiment, the animal is from an Order of Subclass Theria which is Artiodactyla, Carnivora, Cetacea, Perissodactyla, Primate, Proboscides, or Lagomorpha. Preferably, the animal is a Human.

In a preferred embodiment, the implantation site is subcutaneous, intramuscular, intraorgan, arterial/venous vascularity of an organ, cerebro-spinal fluid, or lymphatic fluid. More preferably, the implantation site is subcutaneous. In a most preferred embodiment, the method includes implanting encapsulated islets in a subcutaneous implantation site.

In a preferred embodiment, the method of implanting the composition into an implantation site in an animal in need of treatment for a disease or disorder also includes the step of administering an immunosuppressant or anti-inflammatory agent. Preferably, the immunosuppressant or anti-inflammatory agent is administered for less than 6 months. More preferably, the immunosuppressant or anti-inflammatory agent is administered for less than 1 month.

In another preferred embodiment, the invention is directed to using a therapeutic composition which includes a plurality of encapsulating devices having an average diameter of less than 400 μm, where the encapsulating devices include encapsulated cells in an encapsulation material and the composition has at least about 500,000 cells/ml, in a method which includes the step of implanting the composition into an implantation site in an animal in need of treatment for a disease or disorder. Preferably, the implantation is an injection.

Preferably, the disease or disorder is neurologic, cardiovascular, hepatic, endocrine, skin, hematopoietic, immune, neurosecretory, metabolic, systemic, or genetic. In a most preferred embodiment, the disease is diabetes.

Preferably, the animal is from an Order of Subclass Theria which is Artiodactyla, Carnivora, Cetacea, Perissodactyla, Primate, Proboscides, or Lagomorpha. More preferably, the animal is a Human.

Preferably, the implantation site is subcutaneous, intramuscular, intraorgan, arterial/venous vascularity of an organ, cerebro-spinal fluid, or lymphatic fluid. More preferably, the implantation site is subcutaneous. In a most preferred embodiment, the method includes implanting encapsulated islets in a subcutaneous implantation site.

In a preferred embodiment, the method of implanting the composition into an implantation site in an animal in need of treatment for a disease or disorder also includes the step of administering an immunosuppressant or anti-inflammatory agent. Preferably, the immunosuppressant or anti-inflammatory agent is administered for less than 6 months. More preferably, the immunosuppressant or anti-inflammatory agent is administered for less than 1 month.

In another embodiment the invention is directed to a method of encapsulating a biological material which includes the steps of:

adding a solution which includes a first buffer to the biological material;

centrifuging the biological material to form a pelleted biological material;

removing supernatant;

adding a solution which includes a photoinitiator dye conjugated to a cell adsorbing material to the pelleted biological material;

resuspending and incubating the pelleted biological material with the solution including the photoinitiator dye conjugated to the cell adsorbing material for an effective amount of time;

centrifugating mixture;

removing the solution including the photoinitiator dye conjugated to the cell adsorbing material;

resuspending the pelleted biological material with a second solution including a second buffer;

centrifugating and removing the second buffer;

resuspending and mixing the biological material with a photoactive polymer solution; and irradiating the resuspended biological material with a photoactive polymer solution with an energy source to form an encapsulated biological material. Preferably, the encapsulated biological material is a PEG conformal coated islet allograft.

Preferably, the cell adsorbing material is a polycationic polymer. In a preferred embodiment, the polycationic polymer is a PAMAM Dendrimer. In an alternate preferred embodiment, the polycationic polymer is poly(ethyleneimine).

Preferably, the biological material is an organ, tissue or cell. More preferably, the tissue is a cluster of insulin producing cells. More preferably, the cell is an insulin producing cell.

In a preferred embodiment, the first and second buffer is 1 to 200 mM. More preferably, the first and second buffer is 10 to 50 mM. More preferably, the first and second buffer is 20 mM.

In a preferred embodiment, the photoinitiator is carboxyeosin, ethyl eosin, eosin Y, fluorescein, 2,2-dimethoxy, 2-phenylacetophenone, 2-methoxy, 2-phenylacetophenono, camphorquinone, rose bengal, methylene blue, erythrosin, phloxine, thioinine, riboflavin or methylene green. More preferably, the photoinitiator is carboxyeosin.

In a preferred embodiment, the photoactive polymer solution includes a polymerizable high density ethylenically unsaturated PEG and a sulfonated comonomer. In a more preferred embodiment, the polymerizable high density ethylenically unsaturated PEG is a high density acrylated PEG. Preferably, the polymerizable high density acrylated PEG has a molecular weight of 1.1 kD.

In a preferred embodiment, the sulfonated comonomer is 2-acrylamido-2-methyl-1-propanesulfonic acid, vinylsulfonic acid, 4-styrenesulfonic acid, 3-sulfopropyl acrylate, 3-sulfopropyl methacrylate, or n-vinyl maleimide sulfonate. In a more preferred embodiment, the sulfonated comonomer is 2-acrylamido-2-methyl-1-propanesulfonic acid.

In a preferred embodiment, the photoactive polymer solution also includes a cocatalyst which is triethanolamine, triethylamine, ethanolamine, N-methyl diethanolamine, N,N-dimethyl benzylamine, dibenzyl amino, N-benzyl ethanolamine, N-isopropyl benzylamine, tetramethyl ethylenediamine, potassium persulfate, tetramethyl ethylenediamine, lysine, omithine, histidine or arginine. More preferably, the cocatalyst is triethanolamine.

In a preferred embodiment, the photoactive polymer solution also includes an accelerator which is N-vinyl pyrrolidinone, 2-vinyl pyridine, 1-vinyl imidazole, 9-vinyl carbazone, 9-vinyl carbozol, acrylic acid, n-vinylcarpolactam, 2-allyl-2-methyl-1,3-cyclopentane dione, or 2-hydroxyethyl acrylate. More preferably, the accelerator is N-vinyl pyrrolidinone.

In a preferred embodiment, the photoactive polymer solution also includes a viscosity enhancer which is selected from the group including natural and synthetic polymers. In a more preferred embodiment, the viscosity enhancer is 3.5 kD PEG-triol or 4 kD PEG-diol.

In a preferred embodiment, the photoactive polymer solution also includes a density adjusting agent. More preferably, the density adjusting agent is Nycodenz or Ficoll.

In a preferred embodiment, the photoactive polymer solution also includes a "Good" buffer. In a more preferred embodiment, the "Good" buffer is HEPES or MOPS. In a most preferred embodiment, the "Good" buffer is MOPS.

In a preferred embodiment, the energy source is an Argon laser.

In a preferred embodiment, the biological material for the encapsulation method is neurologic, cardiovascular, hepatic, endocrine, skin, hematopoietic, immune, neurosecretory, metabolic, systemic, or genetic.

In a preferred embodiment, the biological material is from an animal of Subclass Theria of Class Mammalia. In a more preferred embodiment, the animal is from an Order of Subclass Theria which is Artiodactyla, Carnivora, Cetacea, Perissodactyla, Primate, Proboscides, or Lagomorpha. In a most preferred embodiment, the animal is a Human.

In another embodiment, the invention is directed to a composition for encapsulating biological material which includes a polymerizable high density ethylenically unsaturated PEG having a molecular weight between 900 and 3,000 Daltons, and a sulfonated comonomer. In a preferred embodiment, the polymerizable high density ethylenically unsaturated PEG is a polymerizable high density acrylated PEG. In a more preferred embodiment, the polymerizable high density acrylated PEG has a molecular weight of 1.1 kD.

In a preferred embodiment, the sulfonated comonomer is 2-acrylamido-2-methyl-1-propanesulfonic acid, vinylsulfonic acid, 4-styrenesulfonic acid, 3-sulfopropyl acrylate, 3-sulfopropyl methacrylate, or n-vinyl maleimide sulfonate. In a most preferred embodiment, the sulfonated comonomer is 2-acrylamido-2-methyl-1-propanesulfonic acid.

In a preferred embodiment, the composition for encapsulating biological material further includes a cocatalyst which is triethanolamine, triethylamine, ethanolamine, N-methyl diethanolamine, N,N-dimethyl benzylamine, dibenzyl amino, N-benzyl ethanolamine, N-isopropyl benzylamine, tetramethyl ethylenediamine, potassium persulfate, tetramethyl ethylenediamine, lysine, omithine, histidine or arginine. In a more preferred embodiment, the cocatalyst is triethanolamine.

In a preferred embodiment, the composition for encapsulating biological material further includes an accelerator which is N-vinyl pyrrolidinone, 2-vinyl pyridine, 1-vinyl imidazole, 9-vinyl carbazone, 9-vinyl carbozol, acrylic acid, n-vinylcarpolactam, 2-allyl-2-methyl-1,3-cyclopentane dione, or 2-hydroxyethyl acrylate. In a more preferred embodiment, the accelerator is N-vinyl pyrrolidinone.

In a preferred embodiment, the composition for encapsulating biological material is biocompatible with a score of at least about a "2". More preferably, the composition is biocompatible with a score of at least about a "2" in a mammal, even more preferably in a sub-human primate and most preferably in a human.

In a preferred embodiment, the composition for encapsulating biological material has the quality of permselectivity. More preferably, the permselectivity can be engineered by manipulating the composition.

In a preferred embodiment, the composition for encapsulating biological material has an allowance of cell functionality with a score of at least about a "2". In a more preferred embodiment, the allowance of cell functionality with a score of at least about a "2" is in a mammal, even more preferably in a sub-human primate and most preferably in a human.

In a preferred embodiment, the composition for encapsulating biological material further is biodegradable. More preferably, the composition is biodegradable in a mammal. Even more preferably, the composition is biodegradable in a sub-human primate. In a most preferred embodiment, the composition is biodegradable in a human.

Further aspects, features and advantages of this invention will become apparent from the detailed description of the preferred embodiments which follow.

BRIEF DESCRIPTION OF THE DRAWINGS

FIG. 88A shows the cells under normal light and FIG. 88B shows the cells under fluorescent light with FDA/EB staining.

FIG. 28A shows human cells after 2 weeks of culture under fluorescent light with FDA/EB staining.

DETAILED DESCRIPTION OF THE PREFERRED EMBODIMENT

Figure 1:
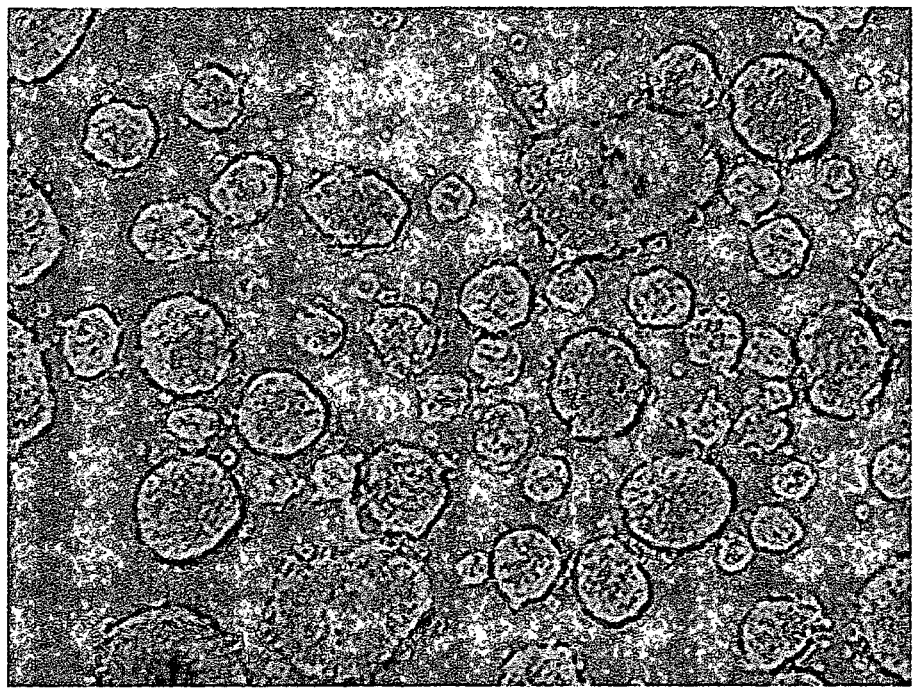
FIG. 1A is a photograph of isolated Cynomolgus primate islets.
FIG. 1B is a photograph of PEG conformally coated Cynomolgus primate islets.
Figure 1:
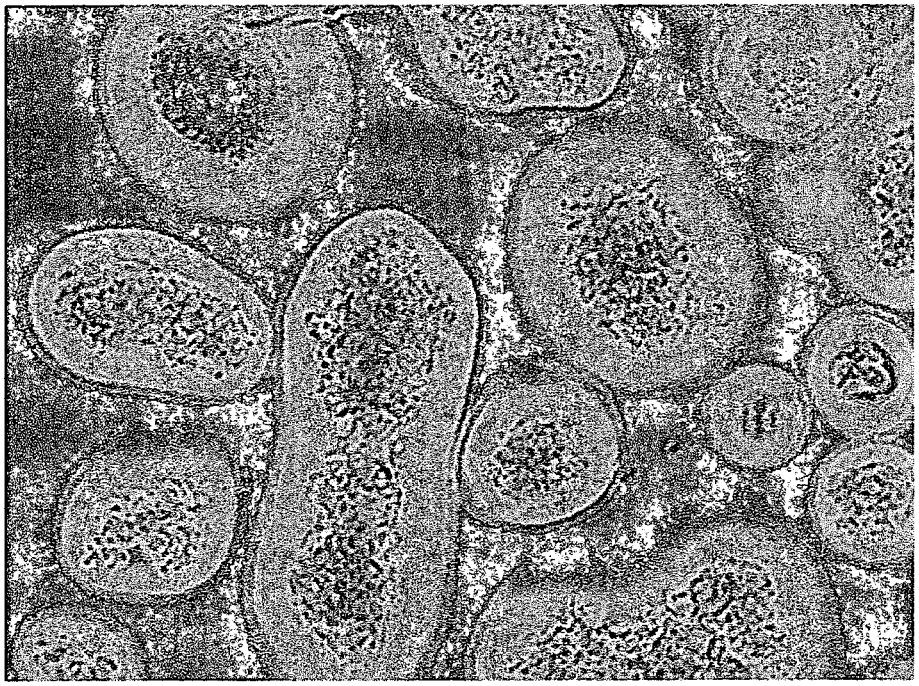

One preferred embodiment of the invention is related to compositions and methods of treating one or more diseases or disorders, such as neurologic (e.g., Parkinson's disease, Alzheimer's disease, Huntington's disease, Multiple Sclerosis, blindness, peripheral nerve injury, spinal cord injury, pain and addiction), cardiovascular (e.g., coronary artery, angiogenesis grafts, valves and small vessels), hepatic (e.g., acute liver failure, chronic liver failure, and genetic diseases effecting the liver), endocrine (e.g., diabetes, obesity, stress and adrenal, parathyroid, testicular and ovarian diseases), skin (e.g., chronic ulcers and diseases of the dermal and hair stem cells), hematopoietic (e.g., Factor VIII and erythropoietin), or immune (e.g., immune intolerance or auto-immune disease), in a subject in need of treatment comprising:

providing cells or tissue, such as pancreatic islets, hepatic tissue, endocrine tissues, skin cells, hematopoietic cells, bone marrow stem cells, renal tissues, muscle cells, neural cells, stem cells, embryonic stem cells, or organ specific progenitor cells, or genetically engineered cells to produce specific factors, or cells or tissue derived from such;

enclosing said cells or tissue within at least one encapsulating material, such as a hydrogel, made of physically or chemically crosslinkable polymers, including polysaccharides such as alginate, agarose, chitosan, poly(amino acids), hyaluronic acid, chondroitin sulfate, dextran, dextran sulfate, heparin, heparin sulfate, heparan sulfate, gellan gum, xanthan gum, guar gum, water soluble cellulose derivatives, carrageenan, or proteins, such as gelatin, collagen, albumin, or water soluble synthetic polymers with ethylenically unsaturated groups or their derivatives, such as poly(methyl methacrylate) (PMMA), or poly(2-hydroxyethyl methacrylate) (PHEMA), poly(ethylene glycol) (PEG), poly(ethylene oxide) (PEO), poly(vinyl alcohol) (PVA), poly(vinylpyrrolidone) (PVP), poly(thyloxazoline) (PEOX); or a combination of the above, such as alginate mixed with PEG, or more hydrophobic or water insoluble polymers, such as poly(glycolic acid) (PGA), poly(lactic acid) (PLA), or their copolymers (PLA-GA), or polytetrafluoroethylene (PTFE) and administering a therapeutically effective amount of said encapsulated cells or tissue to the subject in need of treatment via subcutaneous injection or implant, or directly into organs via either direct injection into the substance of the organ or injection through the vascular system of those organs.

Organs maybe selected from, but not limited to, liver, spleen, kidney, lung, heart, brain, spinal cord, muscle, and bone marrow. The subject in need of treatment may be selected from, but not limited to, mammals, such as humans, sub-human primates, cows, sheep, horses, swine, dogs, cats, and rabbits as well as other animals such as chickens, turkeys, or fish.

In a further embodiment of the invention, the encapsulated cell or tissue may be administered to a subject in need of treatment in combination with an immunosuppressant and/or an anti-inflammatory agent. The immunosuppressant may be selected from, but not limited to cyclosporine, sirolimus, rapamycin, or tacrolimus. The anti-inflammatory agent may be selected from, but not limited to, aspirin, ibuprofen, steroids, and non-steroidal anti-inflammatory agents. Preferably, the immunosuppressant and/or an anti-inflammatory agent is administered for six months following implantation or injection of the encapsulated cells or tissue. More preferably the immunosuppressant and/or an anti-inflammatory agent is administered for one month following implantation or injection of the encapsulated cells or tissue In a preferred embodiment, encapsulated islets are implanted or injected subcutaneously or into liver or spleen. In one aspect of the invention, conformally coated islets are administered subcutaneously.

Preferably, the encapsulated material comprises acrylated PEG and at least one comonomer, such as N-vinyl pyrrolidinone, 2-vinyl pyridine, 1-vinyl imidazole, 9-vinyl carbazone, acrylic acid, and 2-allyl-2-methyl-1,3-cyclopentane dione, 2-acrylamido-2-methyl-1-propanesulfonic acid, vinylsulfonic acid, 3-sulfopropyl acrylate, 3-sulfopropyl methacrylate, and 2-acrylamido-2-methyl-1-propanesulfonic acid, plus N-vinyl pyrrolidinone. Most preferably the encapsulating material comprises acrylated PEG with 2-acrylamido-2-methyl-1-propanesulfonic acid (AMPS) and/or N-vinyl pyrrolidinone (NVP) as a comonomer, to form encapsulated cells or tissue that are conformally coated by a process such as an interfacial photopolymerization process.

In some embodiments of the invention, the concentration of ingredients and composition of encapsulating solution may vary. Preferred concentration ranges are as follows.

For Buffer solution a preferred concentration is 1 to 200 mM, yet more preferred is 5 to 100 mM, and yet more preferred is 10 to 50 mM.

For $CaCl_2$ a preferred concentration is 0.1 to 40 mM, yet more preferred is 0.5 to 20 mM, and yet more preferred is 1 to 5 mM.

For Manitol a preferred concentration is 10 mM to 6M, yet more preferred is 50 mM to 3M, yet more preferred is 100 mM to 1M, and yet more preferred is 200 to 300 mM.

For pH of $CaCl_2$/Manitol solution a preferred value is 6 to 8, yet more preferred is 6.4 to 7.6, and yet more preferred is 6.6 to 7.4.

For DEN-EY a preferred concentration is 0.005 to 8 mg/ml, yet more preferred is 0.01 to 4 mg/ml, and yet more preferred is 0.05 to 2 mg/ml.

For DEN-EY conjunction level a preferred level is 0.15 to 68, yet more preferred is 1 to 34, and yet more preferred is 1.5 to 15.

For pH of macromer solution a preferred value is 6.5 to 9.5, yet more preferred is 7 to 9, and yet more preferred is 7.5 to 8.5.

For PEG TA a preferred concentration is 0.1 to 100%, yet more preferred is 0.2 to 50%, and yet more preferred is 1 to 25%.

For PEG TA a preferred density is 0.05 to 20 K, yet more preferred is 0.1 to 10 K, yet more preferred is 0.5 to 5 K, and yet more preferred is 0.8 to 2.5 K.

For PEG-triol a preferred concentration is 0.1 to 100%, yet more preferred is 1 to 75%, and yet more preferred is 2 to 50%.

For PEG-triol a preferred density is 0.15 to 70 K, yet more preferred is 0.3 to 35 K, yet more preferred is 1.5 to 15 K, and yet more preferred is 2.3 to 7.5 K.

For PEG-diol a preferred concentration is 0.1 to 100% yet more preferred is 1 to 75%, and yet more preferred is 2 to 50%.

For PEG-diol a preferred density is 0.2 to 80 K, yet more preferred is 0.5 to 40 K, yet more preferred is 1 to 20 K, and yet more preferred is 2 to 10 K.

For TEoA a preferred concentration is 5 mM to 2 M, yet more preferred is 10 mM to 1M, yet more preferred is 50 to 500 mM, and yet more preferred is 75 to 125 mM.

For AMPS a preferred concentration is 2 to 640 mg/ml, yet more preferred is 5 to 300 mg/ml, and yet more preferred is 10 to 150 mg/ml.

For NVP a preferred concentration is 0.01 to 40 µl/ml, yet more preferred is 0.1 to 20 µl/ml, and yet more preferred is 0.5 to 10 µl/ml.

For Nycodenz a preferred concentration is 0.1 to 100%, yet more preferred is 1 to 50%, and yet more preferred is 5 to 25%.

For the Laser a preferred strength is 10 mW/cm$^2$ to 4 W/cm$^2$, yet more preferred is 25 mW/cm$^2$ to 2 W/cm$^2$, and yet more preferred is 75 mW/cm$^2$ to 1 W/cm$^2$.

For the light source a preferred time is 3 seconds to 20 minutes, yet more preferred is 6 seconds to 10 minutes, and yet more preferred is 12 seconds to 3 minutes.

In an embodiment, the encapsulating material comprises a hydrogel that forms a sphere around at least one cell or tissue. In a further embodiment, the encapsulating material is an alginate microcapsule, which is conformally coated with another encapsulating material comprising acrylated PEG. In one embodiment, a cell or tissue may be encapsulated in a biocompatible alginate microcapsule, wherein the alginate is made biocompatible by coating the alginate in a biocompatible material, such as PEG or hyaluronic acid, purifying the alginate and/or removing the poly-lysine and replacing it with PEG.

Most preferably the disease to be treated is diabetes, the cells or tissue comprise insulin producing cells or tissue, or cells or tissue derived from pancreatic cells or tissue, or cells derived from progenitor or stem cells that are converted into insulin producing cells, and the encapsulated cells or tissue are administered to the subject in need of treatment via subcutaneous or liver injection or implant.

According to an embodiment of the invention the microcapsules of encapsulated insulin-producing cells or tissue may have an average diameter of 10 µm to 1000 µm, preferably 100 µm to 600 µm, more preferably 150 µm to 500 µm, and most preferably 200 µm to 300 µm. In another embodiment, the invention relates to an insulin-producing cell or tissue encapsulated in microcapsules having a concentration of at least 2,000 IEQ (islet equivalents)/ml, preferably at least 9,000 IEQ/ml, and more preferably at least 200,000 IEQ/ml. In another embodiment of the invention, the volume of insulin-producing cells or tissue encapsulated in microcapsules administered per kilogram body mass of a subject may be 0.001 ml to 10 ml, preferably 0.01 ml to 7 ml, more preferably 0.05 ml to 2 ml. In a further embodiment of the invention, the ratio of microcapsule volume to insulin producing cell or tissue volume is less than 300 to 1, preferably less than 100 to 1, more preferably less than 50 to 1, and most preferably less than 20 to 1.

According to an embodiment of the invention, conformally coated insulin-producing cells or tissue may have an average membrane thickness of 1 to 400 µm, preferably 10 to 200 µm, and more preferably 10 to 100 µm. In a further embodiment the invention relates to a conformally coated insulin-producing cell or tissue having a concentration of at least 10,000 IEQ/ml, preferably at least 70,000 IEQ/ml, more preferably at least 125,000 IEQ/ml, and most preferably at least 200,000 IEQ/ml. According to an embodiment of the invention the volume of the conformally coated insulin producing cell or tissue administered per kilogram body mass of a subject may be 0.01 to 7 ml, preferably 0.01 to 2 ml, and more preferably 0.04 to 0.5 ml. In another embodiment of the invention the ratio of conformal coating volume to insulin-producing cell or tissue volume is less than 13 to 1, preferably less than 8 to 1, more preferably less than 5 to 1, and most preferably less than 2.5 to 1.

According to an embodiment of the invention the microcapsules of encapsulated cells or tissue may have an average diameter of 10 µm to 1000 µm, preferably 100 µm to 600 µm, more preferably 150 µm to 500 µm, and most preferably 200 µm to 300 µm. In a further embodiment of the invention, the ratio of microcapsule volume to insulin producing cell or tissue volume is less than 300 to 1, preferably less than 100 to 1, more preferably less than 50 to 1, and most preferably less than 20 to 1.

According to an embodiment of the invention, conformally coated cells or tissue may have an average membrane thickness of 1 to 400 µm, preferably 10 to 200 µm, and more preferably 10 to 100 µm. In another embodiment of the invention the ratio of conformal coating volume to cell or tissue volume is less than 13 to 1, preferably less than 8 to 1, more preferably less than 5 to 1, and most preferably less than 2.5 to 1.

An embodiment of the invention relates encapsulated cells or tissue where the cell density is at least about 100,000 cells/ml. Preferably, the encapsulated cell is conformally coated. More preferably, the cell is conformally coated with an encapsulating material comprising acrylated PEG. In a further embodiment, the invention is related to a method of treating diabetes in a subject comprising administering encapsulated islets where the cell density is at least about 6,000,000 cells/ml, preferably where the curative dose is less than about 2 ml per kilogram body mass of the subject.

Another embodiment of the invention is related to agricultural animals or pets, such as cows, sheep, horses, swine, chickens, turkeys, rabbits, fish, or dogs and cats; to change the growth rate, or alter the condition of the animal (e.g., increase meat or dairy production), or protect them from or treat them for different diseases. According to this embodiment, a method of providing cells or tissue to an agriculturally relevant animal comprises:

a) providing a cell or tissue;
b) enclosing said cell or tissue within at least one encapsulating material, such as a hydrogel, made of physically or chemically crosslinkable polymers, including polysaccharides such as alginate, agarose, chitosan, poly(amino acids), hyaluronic acid, chondroitin sulfate, dextran, dextran sulfate, heparin, heparin sulfate, heparan sulfate, gellan gum, xanthan gum, guar gum, water soluble cellulose derivatives, carrageenan, or proteins, such as gelatin, collagen, albumin, or water soluble synthetic polymers or their derivatives, such as methyl methacrylate (MMA), or 2-hydroxyethyl methacrylate (HEMA), polyethylene glycol (PEG), poly(ethylene oxide) (PEO), poly(vinyl alcohol) (PVA), poly(vinylpyrrolidone) (PVP), poly(thyloxazoline) (PEOX); or a combination of the above, such as alginate mixed with PEG, or more hydrophobic or water insoluble polymers, such as poly(glycolic acid) (PGA), poly(lactic acid) (PLA), or their copolymers (PLA-GA), or polytetrafluoroethylene (PTFE); and
c) administering said encapsulated cell or tissue to the subject in need of treatment via subcutaneous injection or implant, or directly into organs via either direct injection into the substance of the organ or injection through the vascular system of those organs.

Definitions:

As used in the present application, the following definitions apply:

Allografts—grafts between two or more individuals with different HLA or BLC immune antigen makeup at one or more loci (usually with reference to histocompatibility loci).

Athymic mice—has an incomplete immune system.

Autograft—graft taken from one part of the body and returned to the same individual.

ApoE2—a protein that shuttles lipids through the body.

Biocompatibility—the ability to exist alongside living things without harming them.

Cell aggregate—a collection of cells into a mass, unit, or an organelle that are held together by connecting substances, matrices, or structures.

Clinically relevant and Clinical relevance—encapsulating cell or tissue device must be of such a total volume or size to be implantable in the least invasive or most physiologic site for function with the risk/benefit ratio below that of what the host with the disease or disorder faces with the current disease or disorder.

CMRL (Connaught Medical Research Labs) media—well suited for growth of cloning monkey kidney cell cultures and for growth of other mammalian cell lines when enriched with horse or calf serum. Particularly rich in nucleosides and some vitamins.

Commercially relevant and Commercial relevance—encapsulating cell device must be able to meet requirements such as biocompatibility, permselectivity, encapsulated cell viability and function, size, cell retrieval or replacement, and therapeutic effect, in order for it to be produced on an ongoing basis for treatment of the disease process for which it has been designed within the acceptance as a product that is successful in the market place.

Conformal Coating—a relatively thin polymer coating that conforms to the shape and size of the coated particle.

C-peptide—the polypeptide chain in proinsulin linking the alpha and beta chains of active insulin. Insulin is initially synthesized in the form of proinsulin. There is one molecule of C-peptide for every molecule of insulin in the blood. C-peptide levels in the blood can be measured and used as an indicator of insulin production when exogenous insulin (from injection) is present and mixed with endogenous insulin (produced by the body). The C-peptide test can also be used to help assess if high blood glucose is due to reduced insulin production or to reduced glucose intake by the cells. Type 1 diabetics have little or no C-peptide in the blood, while Type 2 diabetics can have reduced or normal C-peptide levels. The concentration of C-peptide in non-diabetics is 0.5-3.0 ng/ml.

Cynomolgus primate—crab-eating macaque, Macaca fascicularis, is native to Southeast Asia.

Cytodex beads—microcarrier beads of Dextran with positive-charged trimethyl-2-hydroxyaminopropyl groups on the surface.

Dendrimer—an artificially manufactured or synthesized polymer molecule built up from branched units called monomers. Defined by regular, highly branched monomers leading to a monodisperse, tree-like or generational structure. Synthesized through stepwise reactions, building the dendrimer up one monomer layer, or "generation," at a time. Each dendrimer consists of a multifunctional core molecule with a dendritic wedge attached to each functional site. The core molecule is referred to as "generation 0." Each successive repeat unit along all branches forms the next generation, "generation 1," "generation 2," and so on until the terminating generation.

Diabetes—a variable disorder of carbohydrate metabolism caused by a combination of hereditary and environmental factors and usually characterized by inadequate secretion or utilization of insulin, by excessive urine production, by excessive amounts of sugar in the blood and urine, and by thirst, hunger, and loss of weight DTZ (diphenylthiocarbazone)—a dye which binds to the zinc within insulin granules Eosin Y—$C_{20}H_6O_5Br_4Na_2$ [MW 691.914] a red dye soluble in water (40%) and strongly fluorescent. Structure is similar to Eosin Y ws, Ethyl eosin, Eosin B, Phloxine, Erythrosin B, Fluorescein, Rose bengal, and Mercurochrome.

Evan's blue staining—An azo dye used in blood volume and cardiac output measurement by the dye dilution method. It is very soluble, strongly bound to plasma albumin, and disappears very slowly.

Ficoll™—high molecular weight sucrose-polymers used to separate cells.

FDA/EB (fluorescein diacetate/ethidium bromide) staining—When stained, the live cells show up as green colored cells, whereas the cells with cytotoxicity and those with compromised cell membrane functions show red coloration of the nuclei.

"Good" buffer—group of buffers developed by N. E. Good and S. Izawa (Hydrogen ion buffers, Methods Enzymol (1972) 24, 53-68).

HbA1c test [equivalent to Hemoglobin A1C; Glycated hemoglobin]—Test used to assess long-term glucose control in diabetes. Alternative names for this test include glycosylated hemoglobin or Hgb, hemoglobin glycated or glycosylated protein, and fructosamine. HbA1c refers to total glycosylated hemoglobin present in erythrocytes. Due to the fact that glucose stays attached for the life of the cell (about 3 months), the test shows what the person's average blood glucose level over a period of 4-8 weeks. This is a more appropriate test for monitoring a patient who is capable of maintaining long-term, stable control. Test results are expressed as a percentage, with 4 to 6% considered normal. The HbA1c "big picture" complements the day to day "snapshots" obtained from the self-monitoring of blood glucose (mg/dL), and the two tests can be related with the conversion equation: HbA1c=(Plasma Blood Glucose+77.3)/35.6. Glycated protein in serum/plasma assesses glycemic control over a period of 1-2 weeks. A below normal test value is helpful in establishing the patient's hypoglycemic state in those conditions.

HEMA (2-hydroxyethyl methacrylate)—used in light curing polymer system and high performance coatings for lasting high gloss against scratching, solvents and weathering. It is used in crosslinkable paint resins and emulsions, binders for textiles and paper. It is used as a adhesion promoter for metal coatings.

IBMX—A potent cyclic nucleotide phosphodiesterase inhibitor; due to this action, the compound increases cyclic AMP and cyclic GMP in tissue and thereby activates multiple cell processes.

IP (Intraperitoneal)—Within the peritoneal cavity, the area that contains the abdominal organs.

IEQ (Islet equivalent)—defination based on both insulin content and morphology/size. An insulin granule binding dye, such as diphenylthiocarbazone (DTZ) is commonly used to identify beta cells. Since beta cells are only one of several other cell types needed to constitute an islet, a morphological assessment, based upon a mean diameter of 150 μm, is used in addition to staining by DTZ, to define an islet equivalent.

M199—originally formulated for nutritional studies of chick embryo fibroblasts. Contains Earle's salts, L-glutamine, and 2,200 mg/L sodium bicarbonate.

Maturity Onset Diabetes of the Young (MODY).—A form of diabetes characterized by early age of onset (usually less than 25 years of age), autosomal dominant inheritance (that is, it is inherited by 50% of a parent's children) with diabetes in at least 2 generations of the patient's family. MODY diabetes that can often be controlled with meal planning or diabetes pills, at least in the early stages of diabetes. It differs from type 2 diabetes in that patients have a defect in insulin secretion or glucose metabolism, and are not resistant to insulin. MODY accounts for about 2% of diabetes worldwide and 6 genes have so far been found that cause MODY, although not all MODY patients have one of these genes. Because MODY runs in families, it is useful for studying diabetes genes and has given researchers useful information about how insulin is produced and regulated by the pancreas.

MDCK (Madin-Darby canine kidney) cells—Epithelial-like cell line established from normal kidney of dog, susceptible for many viral species.

Microcapsules—small particles that contain an active agent or core material surrounded by a coating or shell.

MMA (methyl methacrylate)—acrylic monomer, colorless liquid with a slight irritating odor.

NIT (NOD insulinoma tumor) cell line—cell line developed from pancreatic beta cells of a transgenic NOD mouse.

NVP (N-vinyl pyrrolidinone)—monomer produced from the reaction of acetylene with 2-Pyrrolidone. It serves as a reactive diluent in a variety of applications.

Nycodenz™ (Nycomed Pharma, Oslo, Norway)—Diatrizoic acid, a non-ionic X-ray contrast medium, used to make density gradients. A favorable property of Nycodenz solutions is that the osmolality and density can easily be varied over a broad range. An effective non-ionic, water-soluble contrast agent which is used in myelography, arthrography, nephroangiography, arteriography, and other radiographic procedures. Its low systemic toxicity is the combined result of low chemotoxicity and low osmolality.

Oral Glucose Tolerance Testing (OGTT)—A screening test for diabetes that involves testing an individual's plasma glucose level after he drinks a solution containing 75 grams of glucose. Currently, a person is diagnosed with diabetes if his plasma glucose level is 200 mg/dL or higher two hours after ingesting the glucose. Those with a plasma glucose level less than 200 mg/dL but greater than or equal to 140 mg/dL are diagnosed with a condition called impaired glucose tolerance. People with this condition have trouble metabolizing glucose, but the problem is not considered severe enough to classify them as diabetic. Individuals with impaired glucose tolerance are at a slightly elevated risk for developing high blood pressure, blood lipid disorders, and Type 2 diabetes.

Permselectivity—preferential permeation of certain ionic species through a membrane.

PoERV (porcine endogenous retrovirus)—An endogenous retrovirus exists as part of the DNA in all mammals and is passed down to offspring over successive generations.

postprandial—occurring after a meal

Proinsulin—a protein made by the pancreas beta cells which is cleaved into 3 units—C-peptide, alpha chain and beta chain. The alpha and beta chains are the functional units of insulin.

SGS (Static glucose stimulation)—static glucose challenge, evaluating the ability of the islets to secrete insulin in response to different glucose concentrations.

Streptozotocin—an antibiotic, $C_8H_{15}N_3O_7$, produced by an actinomycete (Streptomyces achromogenes) and active against tumors but damaging to insulin-producing cells and now also regarded as a carcinogen.

Theophylline—stimulates the release of catecholamines and reduces cerebral blood flow, thereby facilitating stronger metabolic responses to and a prompter perception of decreasing glucose levels.

Therapeutically effective amount—amount of a therapeutic agent produced by cells or tissue which, when administered to a subject in need thereof, is sufficient to effect treatment for a disease or disorder, or to effectively change the growth rate or alter the condition of an animal. The amount of encapsulated cells or tissue corresponding to a "therapeutically effective amount" will vary depending upon factors such as the disease condition and the severity thereof, the identity of the subject in need thereof, and the type of therapeutic agent delivered by the cells or tissue for the disease or disorder, but can nevertheless be readily determined by one of skill in the art.

Treating and Treatment—to alleviate a disease or disorder in a subject, such as a human, by the dosage of encapsulated cells or tissue to the subject in need of treatment via subcutaneous injection or implant, or directly into organs via either direct injection into the substance of the organ or injection through the vascular system of those organs and includes:

(a) prophylactic treatment in a subject, particularly when the subject is found to be predisposed to having the disease or disorder but not yet diagnosed as having it;

(b) inhibiting the disease or disorder; and/or (c) eliminating, in whole or in part, the disease or disorder; and/or (d) improving the subject's health and well-being.

Type 1 diabetes (also insulin-dependent diabetes, insulin-dependent diabetes mellitus)—a form of diabetes mellitus that usually develops during childhood or adolescence and is characterized by a severe deficiency in insulin secretion resulting from atrophy of the islets of Langerhans, and causing hyperglycemia and a marked tendency towards ketoacidosis.

Type 2 diabetes (also non-insulin-dependent diabetes, non-insulin-dependent diabetes mellitus)—a common form of diabetes mellitus that develops especially in adults and most often in obese individuals and that is characterized by hyperglycemia resulting from impaired insulin utilization coupled with the body's inability to compensate with increased insulin production.

Xenografts—A surgical graft of tissue from one species onto or into individuals of unlike species, genus or family. Also known as a heteroplastic graft.

DETAILED DESCRIPTION

The present invention relates to methods of treating a disease or disorder by implanting encapsulated biological material into patients in need of treatment. Diabetes is of particular interest because a method is needed to prevent complications related to the lack of good glycemic control in insulin-requiring diabetics. Specifically, PEG conformally coated islet allografts in diabetic primates are shown herein to be successfully implanted in the subcutaneous site by injection and achieve relatively normal blood glucose values out to 220 days post-implant. The current complications of clinical islet transplantation and the significant risks and discomfort of continuous immunosuppression may be eliminated by applying the methods described herein to patients with insulin-requiring diabetes. In addition, encapsulated islet implants are expected to protect these insulin-requiring diabetic patients and prevent them from developing the complications from diabetes related to inadequate glycemic control in spite of exogenous insulin therapy.

Methods according to the present invention may provide therapeutic effects for a variety of diseases and disorders, in addition to diabetes, in which critical cell-based products lost by disease or disorder may be replaced through implantation of cells or tissue into the body. A preferred embodiment of the invention is the use of human insulin-producing cells from the pancreas, or cells derived from human insulin-producing cells from the pancreas, that are encapsulated as cell clusters for implantation into the subcutaneous site of insulin-requiring patients. Treatment of disease via encapsulated biological materials requires that the encapsulated material be coated with a biocompatible coating, such that the immune system of the patient being treated does not destroy the material before a therapeutic effect can be realized.

Permselectivity of the coating is a factor in the effectiveness of such treatments, because this regulates the availability of nutrients to the cells or tissue, and plays a role in preventing rejection of the biological materials. Permselectivity of the coating affects the nutrition available to the encapsulated cell or tissue, as well as the function of the cell or tissue. Permselectivity can be controlled by varying the components of the biocompatible coating or by varying how the components are used to make the cell coating. Treatment via injection of encapsulated biological materials according to the present invention provides a stable and safe method of treatment. Size of the implant and the site of implantation, as well as replenishment and/or replacement of the encapsulated materials is also a consideration of the methods described herein. These methods provide a treatment that has a wide range of applications in the treatment of disease at various sites of implantation, while avoiding complications associated with other treatment methods.

The conformal coatings described herein can be produced with different pore sizes that can be produced to limit access to the cells by proteins of widely varying molecular weights, including the exclusion of antibodies. This control allows for survival and maintained function of the encapsulated materials, while excluding components of the host immune system. The appropriate pore size of the conformal coating may be determined by routine experimentation for each cell or tissue type and the disease or disorder to be treated. The conformal coatings described herein provide a small encapsulated cell product with a minimal volume of the coating material, thus allowing the coated materials to be implanted into various sites of the body, including direct injection into the liver, spleen, muscle, or other organs, injection via vascular access to any organ, injection into the abdominal cavity, and implantation into a subcutaneous site.

An important factor for successful encapsulated cell therapy is that the permselective coating used to encapsulate the cells be inert in terms of causing inflammatory reactions in the host. Most previous encapsulating materials were not completely biocompatible. With some devices, not making a large scar is sufficient. However, when using the coating for permselective protection between the encapsulated cells and the host immune system, there cannot be any non-specific inflammatory reaction to the host's complement system or to macrophages. If this occurs, then the inflammatory and/or immune reaction is sufficient to release cytokines that readily cross the membrane and can cause the loss of the encapsulated cells. Most encapsulation technologies for islets, which have had difficulties in working appropriately, had non-specific inflammatory reactions due to biocompatibility reactions to the coating materials.

Problems such as chronic inflammation are significantly reduced due to the lack of host reaction to the biocompatible conformal coatings used to encapsulate cells and tissues used in the methods described herein. The components used to produce the conformal coating described herein have been shown to be completely biocompatible when injected into animals, such as, rodents, dogs, pigs, and primates.

We discovered that biocompatibility of hydrogels synthesized from highly acrylated PEG was exceptionally good, and much better than that shown with moderately acrylated PEG hydrogels. The highly acrylated PEGs were either obtained commercially, or home-made by acrylating corresponding PEGs. Hydrogels with highly acrylated PEGs were conformally coated on the surface of alginate microbeads using an interfacial photopolymerization technology. This discovery also can be extended to other biomedical, biotechnological and pharmaceutical areas where biocompatibility of the devices or formulations is of concern.

Some PEG conformal coatings described herein are biodegradable over time, thus allowing the body to safely break down the materials over the course of time and avoiding the need to retrieve the encapsulated materials, which is required by other treatments. Replacement of cells can be done whenever the previous dose of encapsulated materials has begun to lose function. Encapsulated islets may be expected to last two to five years or longer. In the case of subcutaneous injections, replacement of the encapsulated materials may simply be done via another percutaneous injection of new materials into the patient at a different site prior to loss of the previous dose. In the case of encapsulated islets, this replacement can be done prior to loss of function in the first dose of islets, without fear of low glucose values, because the encapsulated islets autoregulate themselves to prevent hypoglycemia. Different implant timing may have to be determined for treating diseases and disorders using cells or tissues that do not autoregulate the release of their product.

A factor in producing encapsulated cell products is the cell source. Cells may be primary cells, expanded cells, differentiated cells, cell lines, or genetically engineered cells. In the case of human islets, primary islets may be isolated from cadaver-donated pancreases; however, the number of human pancreata available for isolating islets is very limited. Alternative cell sources may be used to provide cells for encapsulation and injection.

One alternative source of cells, particularly insulin-producing cells, is embryonic stem cells. Human embryonic stem cells come from the very early fetus. They are only available when grown from frozen, fertilized human eggs collected from couples that have successfully undergone in vitro fertilization and no longer want to keep these fertilized eggs for future children. Embryonic stem cells have the ability to grow indefinitely, potentially avoiding the need for the mass of tissues required for transplantation. There are a series of steps required to differentiate these embryonic stem cells into insulin producing cells with clinical relevancy. A few studies have shown both mouse and human embryonic stem cells can produce insulin when treated under tissue culture with a variety of factors. Insulin-producing cells developed from embryonic stem cells may be an acceptable cell source for transplantation, and encapsulated cell or tissue implantation.

Cell Sourcing

Additional cell sources, organ specific progenitor cells from the brain, liver, and the intestine, have been shown to produce insulin. In order to produce insulin, each of these organ specific progenitor cells have undergone tissue culture treatments with a variety of growth and differentiation factors. Additional organ specific progenitor cells from many other organs such as bone marrow, kidney, spleen, muscle, bone, cartilage, blood vessels, and other endocrine organs may also be useful in providing insulin producing cells.

Pancreatic progenitor cells may be used according to the methods of the invention. The pancreas seems to have organ specific stem cells that can produce the three pancreatic cell types in the body under normal and repair conditions. It is believed the islet cells bud off from the duct cells to form the discrete islets. The insulin producing beta cells, as well as the other hormone producing cells, may form directly from differentiating duct cells or may form from pancreatic progenitor cells located amongst the duct cells. These pancreatic progenitor cells may be used to provide insulin-producing cells for encapsulation and implantation according to the methods described herein.

There has been a great deal of research on genetically inserting genes into non-insulin producing cells to make them produce insulin. Genetically engineered cells capable of insulin production may also be used for encapsulation and implantation according to the methods described herein.

The use of pig cells has commonly been considered as a source of islet cells for implantation in patients with diabetes. Over 90 million pigs are raised per year for meat production in the USA alone. Therefore, the number of islets to treat the millions of patients with insulin-requiring diabetes are readily available through large scale processing of adult pig pancreata into purified pig islets for encapsulation. One consideration limiting this choice is the recognition that pigs harbor an endogenous retrovirus (PoERV). There have been efforts to eliminate PoERV from strains of pigs. Virus-free pig xenograft islets may be readily encapsulated and available as a preferred cell source for the treatment of human diabetes.

Alternative xenograft sources for human implantation may be obtained from primary cells of species other than pigs. These other species could be agriculturally relevant animals such as beef, sheep, and even fish. With the ability to expand and differentiate insulin producing cells from pancreatic sources or other stem or progenitor cells, one can envision using insulin-producing cells from many other xenogeneic sources such as primates, rodents, rabbits, fish, marsupials, ungulates and others.

Disease Treatment

Diabetes and other diseases in which a local or circulating factor is deficient or absent can be treated according to the methods described herein. Encapsulated cell therapy may be applied in the treatment of neurologic, cardiovascular, hepatic, endocrine, skin, hematopoietic, and immune disorders and diseases. Neurologic diseases and injuries, such as Parkinson's disease, Alzheimer's disease, Huntington's disease, multiple sclerosis, blindness, spinal cord injury, peripheral nerve injury, pain and addiction may be treated by encapsulating cells that are capable of releasing local and/or circulating factors needed to treat these problems. Cardiovascular tissue, such as the coronary artery, as well as angiogenic growth factor releasing cells used for restoring vascular supply to ischemic cardiac muscle, valves and small vessels may be treated. Acute liver failure, chronic live failure, and genetic diseases affecting the liver may be treated. Endocrine disorders and diseases, such as diabetes, obesity, stress and adrenal, parathyroid, testicular and ovarian diseases may be treated. Skin problems, such as chronic ulcers, and diseases of the dermal and hair stem cells can be treated. Hematopoietic factors such as Factor VIII and erythropoietin may be regulated or controlled by administering cells capable of stimulating a hematopoietic response in a patient. Encapsulated biological materials may also be useful in the production of bone marrow stem cells. Encapsulated materials, such as, antigens from primary cells or genetically engineered cells, may be useful in producing immune tolerance or preventing autoimmune disease. In addition, these materials may be used in vaccines.

Conformal Coating Components

Components of the coatings may be altered depending on the specific cell type and permselectivity desired. Various polymerizable monomers or macromers, photoinitiating dyes, cocatalysts, and accelerants may be used to produce conformally coated cells and tissues.

Monomers or Macromers

Monomers or macromers are used as the building blocks to polymerize biocompatible coatings for use in methods disclosed herein. The monomers are small polymers, which are susceptible to polymerization into the larger polymer membranes of this invention. Polymerization is enabled because the macromers contain carbon-carbon double bond moieties, such as, acrylate, methacrylate, ethacrylate, 2-phenyl acrylate, 2-chloro acrylate, 2-bromo acrylate, itaconate, acrylamide, methacrylamide, and styrene groups. The monomers or macromers are non-toxic to biological material before and after polymerization.

Examples of monomers are methyl methacrylate (MMA) and 2-hydroxyethyl methacrylate (HEMA). Examples of macromers are ethylenically unsaturated derivatives of poly (ethylene oxide) (PEO), poly(ethylene glycol) (PEG), poly (vinyl alcohol) (PVA), poly(vinylpyrrolidone) (PVP), poly (thyloxazoline) (PEOX), poly(amino acids), polysaccharides such as alginate, hyaluronic acid, chondroitin sulfate, dextran, dextran sulfate, heparin, heparin sulfate, heparan sulfate, chitosan, gellan gum, xanthan gum, guar gum, water soluble cellulose derivatives and carrageenan, and proteins such as gelatin, collagen and albumin. These macromers can vary in molecular weight and number of branches, depending on the use. For purposes of encapsulating cells and tissue in a manner that has minimum tissue response, the preferred starting macromer is PEG—triacrylate with MW 1.1K. The molecular weight designation is an average molecular weight of the mixed length polymer.

Photoinitiating Dyes

The photoinitiating dyes capture light energy and initiate polymerization of the macromers and monomers. Any dye can be used which absorbs light having frequency between 320 nm and 900 nm, can form free radicals, is at least partially water soluble, and is non-toxic to the biological material at the concentration used for polymerization. Examples of suitable dyes are ethyl eosin, eosin Y, fluorescein, 2,2-dimethoxy, 2-phenylacetophenone, 2-methoxy, 2-phenylacetophenono, camphorquinone, rose bengal, methylene blue, erythrosin, phloxine, thionine, riboflavin and methylene green. To enhance the dye-cell surface binding, the dyes used here are conjugated to polymers that have strong interactions with cell surfaces, such as polycationic polymers, polymers with multiple phenylboronic acid groups attached. Examples of polycationic polymers include PAMAM dendrimer, linear, branched or dendritic poly (ethyleneimine) (PEI), polyvinylamine, polyallylamine, polylysine, chitosan, and polyhistidine. The preferred initiator dye is the carboxyeosin conjugated to PAMAM Dendrimer Generation 4.

Cocatalyst or Radical Generator

The cocatalyst is a nitrogen-based compound capable of stimulating the free radical reaction. Primary, secondary, tertiary or quaternary amines are suitable cocatalysts, as are any nitrogen atom containing electron-rich molecules. Cocatalysts include, but are not limited to, triethanolamine, triethylamine, ethanolamine, N-methyl diethanolamine, N,N-dimethyl benzylamine, dibenzyl amino, N-benzyl ethanolamine, N-isopropyl benzylamine, tetramethyl ethylenediamine, potassium persulfate, tetramethyl ethylenediamine, lysine, ornithine, histidine and arginine. A preferred cocatalyst is triethanolamine.

Accelerator or Co-Monomer

The accelerator, which is optionally included in the polymerization mixture, is a small molecule containing an allyl, vinyl, or acrylate group, and is capable of speeding up the free radical reaction. Incorporating a sulfonic acid group to the accelerant also can improve the biocompatibility of the final product. Accelerators include, but are not limited to, N-vinyl pyrrolidinone, 2-vinyl pyridine, 1-vinyl imidazole, 9-vinyl carbazone, 9-vinyl carbozol, acrylic acid, 2-allyl-2-methyl-1,3-cyclopentane dione, 2-hydroxyethyl acrylate, 2-acrylamido-2-methyl-1-propanesulfonic acid, vinylsulfonic acid, 4-styrenesulfonic acid, 3-sulfopropyl acrylate, 3-sulfopropyl methacrylate, n-vinylcarpolactam, and n-vinyl maleimide sulfonate (from SurModics), with 2-acrylamido-2-methyl-1-propanesulfonic acid plus N-vinyl pyrrolidinone being the preferred combination of accelerators.

Viscosity Enhancer

To generate conformal coating without long tails on cell aggregates, the viscosity of the macromer solution may be optimized. This may be accomplished by viscosity enhancers which are added into the macromer solution. Preferred viscosity enhancers are PEG—triol with MW 3.5 kD and 4 kD PEG-diol.

Density Adjusting Agent

To generate conformal coating without long tails on cell aggregates, the density of the macromer solution may be optimized. This may be accomplished by adding density adjusting agents into the macromer solution. Preferred density adjusting agents are Nycodenz™ and Ficoll™.

Radiation Wavelength

The radiation used to initiate the polymerization is either longwave UV or visible light, with a wavelength in the range of 320-900 nm. Preferably, light in the range of 350-700 nm, and even more preferred in the range of 365-550 nm, is used. This light can be provided by any appropriate source able to generate the desired radiation, such as a mercury lamp, longwave UV lamp, He-Ne laser, or an argon ion laser or an appropriately filtered xenon light source.

The following examples are provided merely for illustrative purposes of the present invention and are not to be read as limiting the scope of protection of the present invention.

EXAMPLES

Example 1

Isolating Islet Cells in Mice

Donor mice [C57BL/6] with an age range of 18 weeks old and average size of 33 grams were obtained from supplier. Pancreas was exposed with euthanasia laparotomy. The pancreata were distended with Sigma collagenase, Type V. The pancreata were removed and kept in cold collagenase during transport to the isolation laboratory. The isolation process combined 30 pancreata for the digestion process. The digestate was washed with 10% fetal bovine serum in RPMI and centrifuged. The COBE was prepared for purification and a continuous gradient marker was used to make the gradient densities. The gradient was loaded into the COBE and the pancreata digestate was loaded on top to perform the purification process. The purified islets were collected and washed in RPMI media. The islets were cultured in T75 flasks in modified ICM media supplemented with 10% fetal bovine serum until ready for encapsulation.

Isolating Islet Cells in Primates

Juvenile Cynomolgus primates (Macaca fascicularis) with a range of size of 2.5-4.5 kg and adult Baboons (Papio anubis) with a range of size of 10-30 kg were used as donors of pancreata (Table 1). The pancreata were removed at necropsy, ductly cannulated and distended with cold UW solution, placed into UW solution with perfluorocarbon bubbled with oxygen, and transported via courier to facility for islet isolation. A modified primate islet isolation procedure (O'Neil, J, Cell Transplantation 10: 539, 2001) using human Liberase was used to free the islets with minimal mechanical disruption and COBE continuous density gradients. The purified islets were cultured in T75 flasks in modified CMRL media supplemented with 10% fetal bovine serum at 37° C. for 3 to 7 days prior to encapsulation to permit their recovery from the processing damages. FIG. 1A demonstrates a typical yield of purified Cynomolgus primate islets from a donor pancreas.

TABLE 1

Comparison of Cynomolgus and Baboon Islet Isolation Procedures

| Cynomolgus | Baboon |
|---|---|
| Methods | Methods |
| juvenile donor | 10-20 year old donors |
| 4 g pancreas | 25 g pancreas |
| multiple pancreas processing | single pancreas processing |
| collagenase conc. 0.5 mg/ml | collagenase conc. = 0.20 mg/ml |
| digest time = 40 min. | digest time = <20 min. |
| Results | Results |
| 30,000-50,00 IEQ per pancreas | 150,000-200,00 IEQ per pancreas |
| islet index = 0.80 | Islet index = 1.00 |
| # of donors per transplant = 5-10 | # donors per transplant = 2 |

Example 2

Preparation of Conformal Coating Materials

Figure 2:
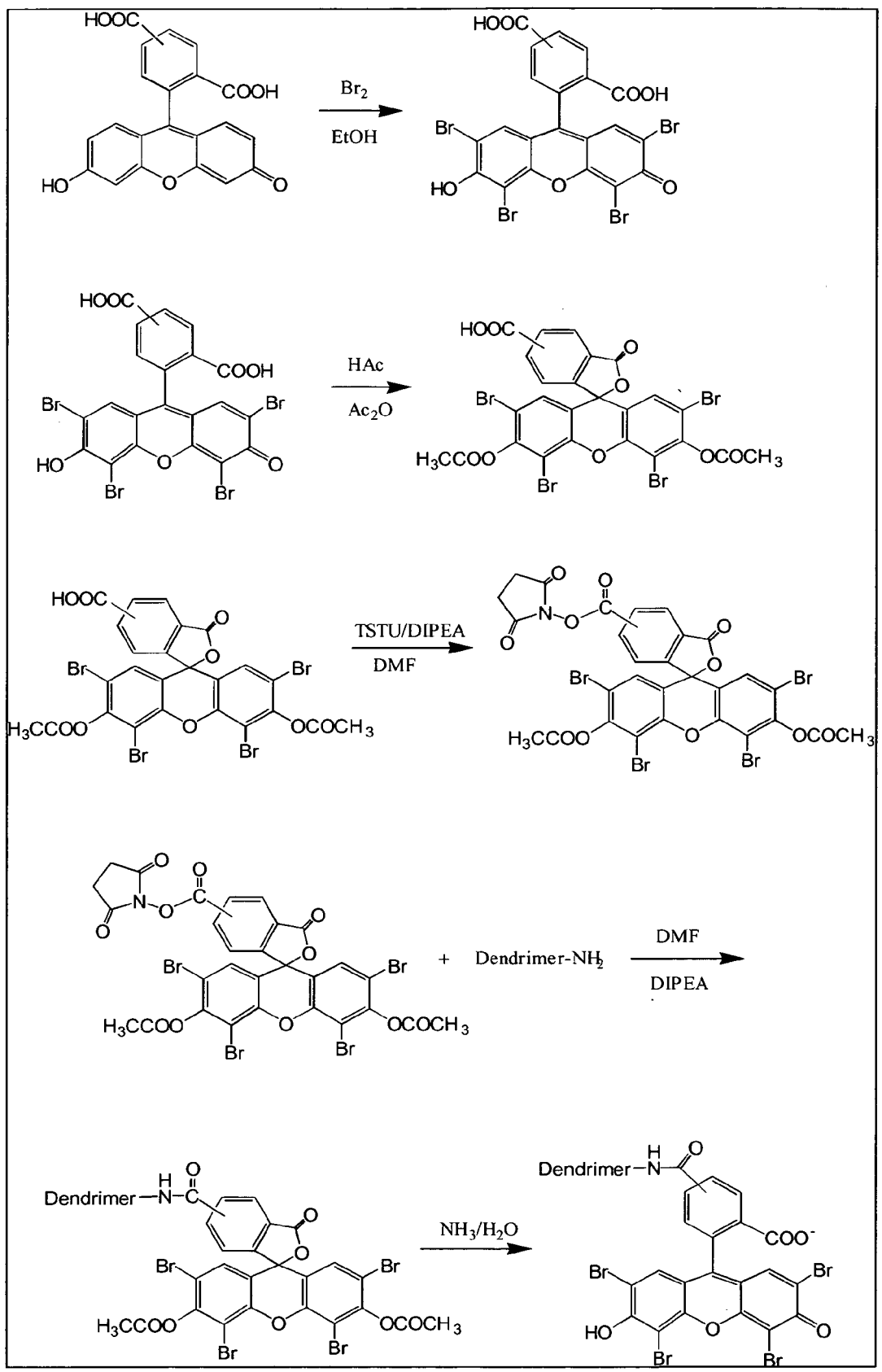
FIG. 2 shows the synthesis of dendrimer eosin Y conjugate.

Depending on the type of cell being encapsulated, the cells were coated directly by a conformal coating or enclosed in a matrix, such as alginate, and then coated with a permselective PEG capsule. FIG. 2 illustrates the synthesis of dendrimer eosin Y conjugate, Dendrimer-EY, a preferred embodiment of this coating, and described as follows.

Figure 3:
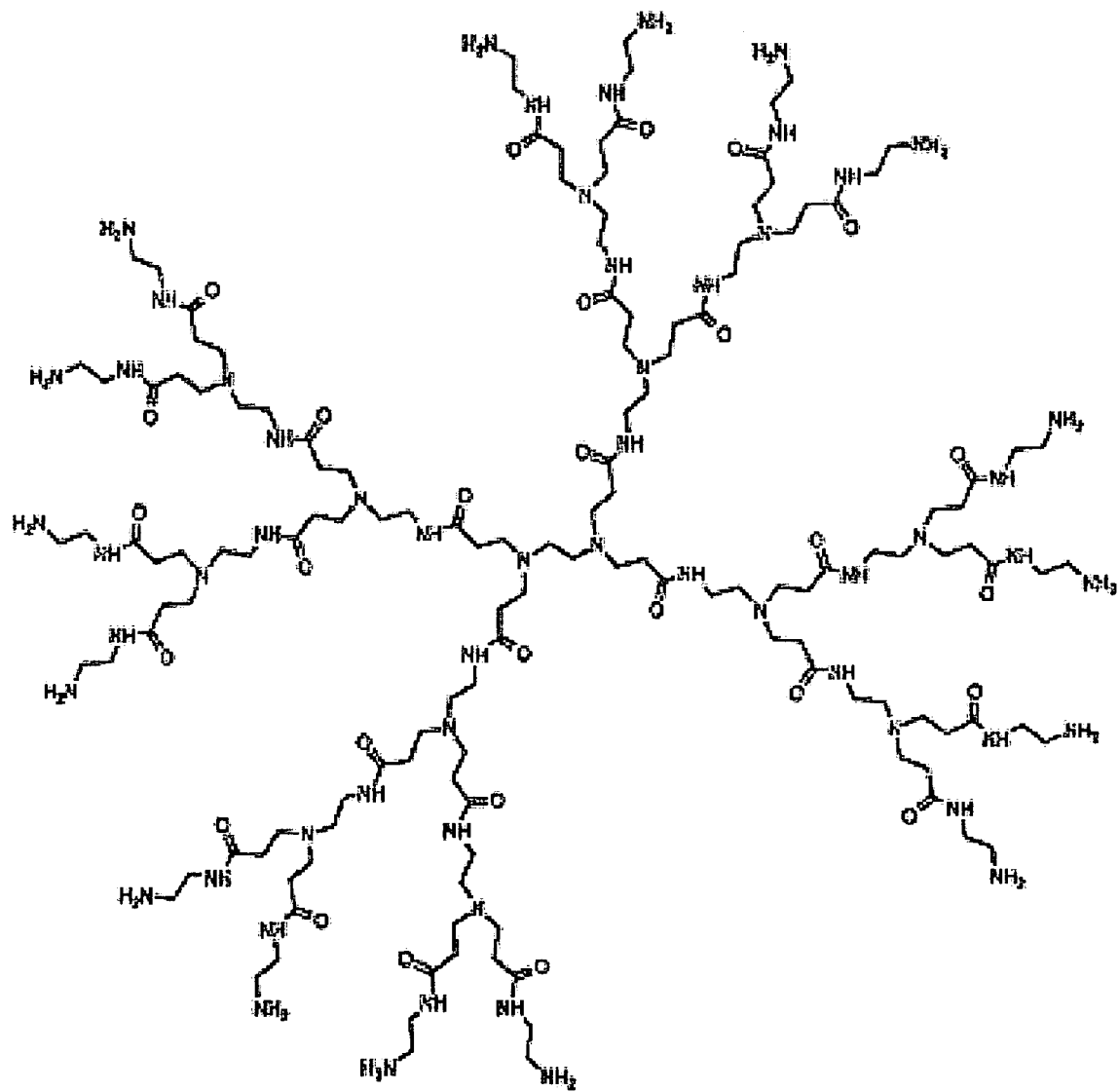
FIG. 3 illustrates a second-generation dendrimer. In the Examples, fourth generation dendrimers are used, which are more highly branched than the second-generation dendrimer illustrated.

The dendrimer used for encapsulation was PAMAM Dendrimer generation 4, which was purchased from Dendritech (FIG. 3). 5(6)-Carboxyeosin was made by bromination of 5(6)-Carboxyfluorescein. The hydroxyl group and 1-carboxyl group were then protected by forming an acetate. The protected 5(6)-Carboxyeosin was activated by N,N,N'N'-Tetramethyl-O-(N-Succinnimidyl)uranium tetrafluoroborate (TSTU). Without further purification, the activated 5(6)-Carboxyeosin diacetate was mixed with PAMAM Dendrimer to form Dendrimer-EY conjugate. The protection group was then removed by reacting with aqueous ammonia. The final product was purified by ultra-purification using a membrane with 5K MWCO, and 50 mM $(NH_4)_2CO_3$ as the washing buffer. Varying the stoichiometric ratio of EY and Dendrimer, Dendrimer-EY with different conjugation levels can be obtained. The optimum conjugation level used for islets encapsulation was 3.4 EY/Dendrimer.

The conjugation level of Dendrimer-EY was determined by UV-Vis. The maximum absorption at 523 nm was measured of the Dendrimer-EY solution in 50 mM $(NH_4)_2CO_3$.

The conjugation level was calculated using the extinction coefficient of 5(6)-Carboxyeosin, $\Sigma=8.4\times10^4$.

Triethanol amine (TEoA), 2-Acrylamido-2-methyl-1-propanesufonic acid (AMPS) and N-Vinylpyrrolidinone (NVP) were purchased from Aldrich without further purification.

Trimethylolpropane ethoxylate triacrylate (PEG 1.1K-TA) was purchased from Sartomer and used without purification. The acrylation level varied from higher 60s to higher 80s. Molecular weights were between 1100 to 1300.

Ethoxylated trimethylolpropane (PEG 3.5K-Triol) was custom synthesized by Carbotech. Poly (ethylene glycol) 3400 (PEG 4K-Diol) was purchased from Union Carbide. PEG 3.5K-triol and PEG 4K-Diol were dissolved in water for injection and lyophilized before use.

Example 3

Encapsulation of Islets

Encapsulating Mouse Islets

A preferred method of coating mouse islets is described as follows. Fifteen milliliters of 20 mM low ionic HEPES buffer (containing 1.8 mM $CaCl_2$ and 260 mM Manitol, pH=7.0) was added to a 15 ml conical tube, containing 10 µl of islets. The supernatant was removed after centrifugation. 15 ml of Den-EY solution (0.1 mg/ml to 0.4 mg/ml in low ionic HEPES buffer) was added into the pellet and the tube was kept horizontal for 10-30 minutes at room temperature. The stained islets were washed twice with low ionic 20 mM HEPES buffer, which was sparged with Argon for at least 30 minutes. The stained islet pellet was mixed with 10 ml of photoactive polymer solution, which was also sparged with Argon and pre-equilibrated in a 8° C. waterbath for at least 30 minutes. The photoactive polymer solution was made in 20 mM HEPES buffer, pH=8.0, which contained up to 20% PEG, 100 mM TEoA, 32 mg/ml AMPS and 2 µl/ml NVP, and 13% Nycodenz. The suspension was transferred into a petri dish and the solution was irradiated with an Argon laser at an irradiance density of 200 $mW/cm^2$ for 1 minute. The polymerization was quenched by adding 1-2 ml of M199 into the petri dish. The contents in the petri dish was transferred into a 50 ml conical containing 40 ml of M199. After washing with M199, the encapsulated islets were put back into culture.

Encapsulating Primate Islets

Islets were loaded with the photoinitiator (Eosin Y) and placed into the PEG encapsulation solution containing the acrylated PEG monomer, TEoA, and NVP. When the argon laser illuminated the islets, the bound Eosin Y was activated to a higher energy state that was captured by the TEoA to produce free radicals. These TEoA radicals diffused off the surface of the islets, broke carbon—carbon double bonds (C=C) between acrylates that covalently bonded the acrylated PEG's together, forming the conformal PEG coatings directly around each islet. The encapsulated islets were then cultured at 37° C. in CMRL supplemented with 10% heat-inactivated Cynomolgus primate allograft serum for 4 to 21 days prior to implantation.

Cynomolgus primate isolated islets were readily encapsulated in a conformal manner surrounding all of the islet surface regardless of shape or size. FIG. 1A shows unencapsulated isolated islets from a Cynomolgus primate. FIG. 1B shows PEG encapsulated isolated islets from a Cynomolgus primate under phase microscopy showing the uniform, conformal coating of the islets.

Example 4

In Vitro Characterization of the Encapsulated Islets

Coating efficiency of encapsulated islets was assessed by Evan's blue staining. Fifteen milliliters of 0.008% Evan's Blue in M199 was added to 0.5 ml of encapsulated islets suspension. After incubating for three minutes, the supernatant was removed by centrifugation and aspiration. The islets were washed three times with M199. The islet suspension (in M199) was placed on a microscope. PEG hydrogel stained light blue.

Viability of encapsulated islets was assessed by fluorescein diacetate (FDA)/ethidium bromide (EB) staining. 2.5 ml of EB stock solution (1 mg in 50 ml PBS) and 12.5 µl of FDA stock solution (5 mg/ml in acetone) was added to 0.5 ml of encapsulated islets suspension in serum free media. Ten minutes after adding the stain, the sample was placed on the fluorescence microscope using the field block for fluorescein. Dead cells stained red and viable cells stained green. The percentage of islets cells that were viable was assessed. Example shown in FIG. 4.

Permeability of the encapsulated islets was assessed by SDS-PAGE. A small aliquot of encapsulated islets was submitted to SDS-PAGE analysis before they were put into media containing serum. One or two average-size islets were picked up under microscopy and incubated separately in a 96-well culture plate with 0.1% SDS solution for about 14-16 hours at room temperature. Normally a minimum of eight sets of islets were picked and incubated. In addition, a pool of 10 islets was picked and incubated at the same time. After incubation, the supernatants were taken out and incubated at 100° C. for 5 minutes. After cooling down, the nine supernatants were loaded onto each polyacrylamide gel. The last well was loaded with the standard molecular weight marker mixture. After electrophoresis of the material in the wells, the gel was fixed and stained with silver stain for a controlled period. The molecular weight cutoff of the PEG gel on each set of the encapsulated islets was determined by comparing with the standard molecular weight marker. Example shown in FIG. 5

Function of encapsulated islets was assessed by static glucose stimulation (SGS) or perfusion study. For static glucose stimulation, four aliquots of 20 islets were hand picked and placed into four wells of a 12-well plate. The islets were washed twice and incubated with a G50 basal solution (glucose concentration—50 mg/DL) for 45 min, followed by a G300 stimulation solution (glucose concentration—300 mg/DL) for 45 min, followed by an IBMX solution for 45 minutes, followed by the G50 basal solution for 45 minutes. A 0.5 ml sample of supernatant was collected at the end of each incubation. The islets were washed twice between incubations. After collecting the last basal samples, all the islets were incubated with acid alcohol overnight for insulin extraction. 0.5 ml samples of the supernatant were collected after insulin extraction. For all the samples collected, insulin concentrations were measured using an appropriate insulin RIA or ELISA kit. For some encapsulated islets, the insulin release was delayed and only a minimum amount of insulin was detected after 45 minutes incubation with the G300 stimulation media. Those islets were incubated in the G300 stimulation media for an extended period of time, and the samples of the supernatant were collected at various time points, such as 1 hour, 2 hours and 3 hours to follow the insulin release kinetics. Example shown in FIG. 6.

For perifusion study, the islet preparation was placed on a filter in a perifusion system first exposed to a G50 basal solution for 40 min, followed by a stimulation with the G300 stimulation solution for 40 minutes, followed by an additional stimulation with G300 plus Theophylline or IBMX. The perifusion of the islets was concluded with a return to a basal level of glucose. Samples were collected at 5 minutes intervals, and assessed by an appropriate RIA or ELISA kit to determine the insulin concentration.

Example 5

Implantation of Conformally Coated Islets into Mice

Mouse islets were conformally coated in a similar method as Example 2. The encapsulated islets were implanted into intraperitoneal (IP) and subcutaneous (SQ) sites of athymic mice, and blood glucose levels were monitored prior to and following implantation.

Figure 7:
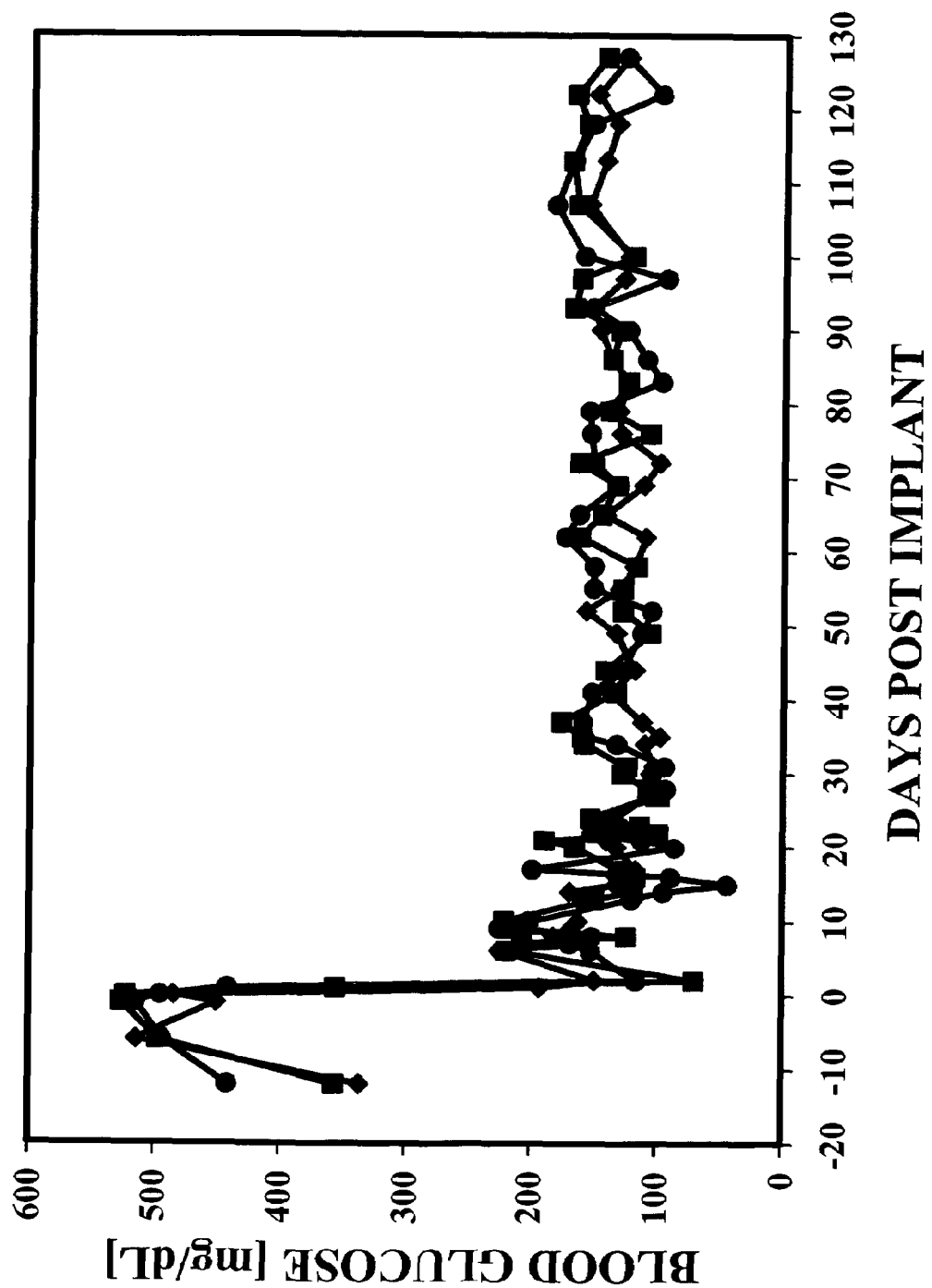
FIG. 7 is a graphical representation of the blood glucose levels measured in athymic mice in which conformally coated mouse islets were implanted at the intraperitoneal site.

FIG. 7 illustrates the blood glucose levels in two athymic mice in which conformally coated mouse islets [2805 IEQ] were implanted at the intraperitoneal site. The implanted islets were able to regulate the blood glucose levels to near normal range for up to 130 days post-implantation.

Figure 8:
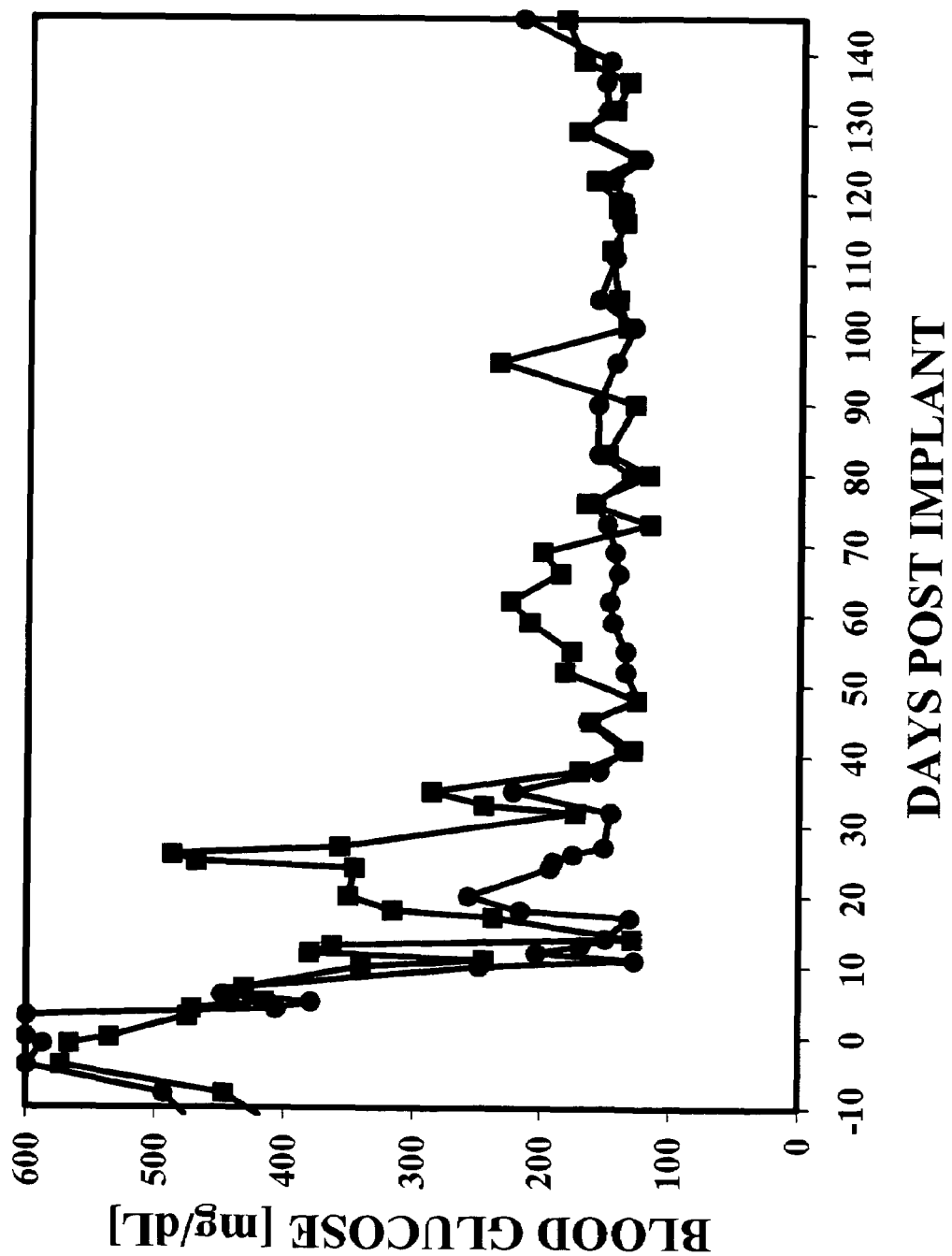
FIG. 8 is a graphical representation of the blood glucose levels measured in athymic mice in which conformally coated mouse islets were implanted at the subcutaneous site.

FIG. 8 illustrates the blood glucose levels in two athymic mice in which conformally coated mouse islets [3300 IEQ] were implanted at the subcutaneous site. Both mice showed reduced blood glucose levels after implantation with only a few spikes between 20 and 30 days post implantation. One of the mice had a steady near normal blood glucose level until day 145 post-implantation. The other mouse showed occasional spikes in blood glucose but the implanted islets were able to reduce the level to near normal after 30 days.

The conformal coatings permitted long-term survival of the islets in the IP site and the coated islets also functioned well in the SQ implants, depending on the islet dosage. The SQ site exhibited excellent biocompatibility in athymic mice.

Figure 9:
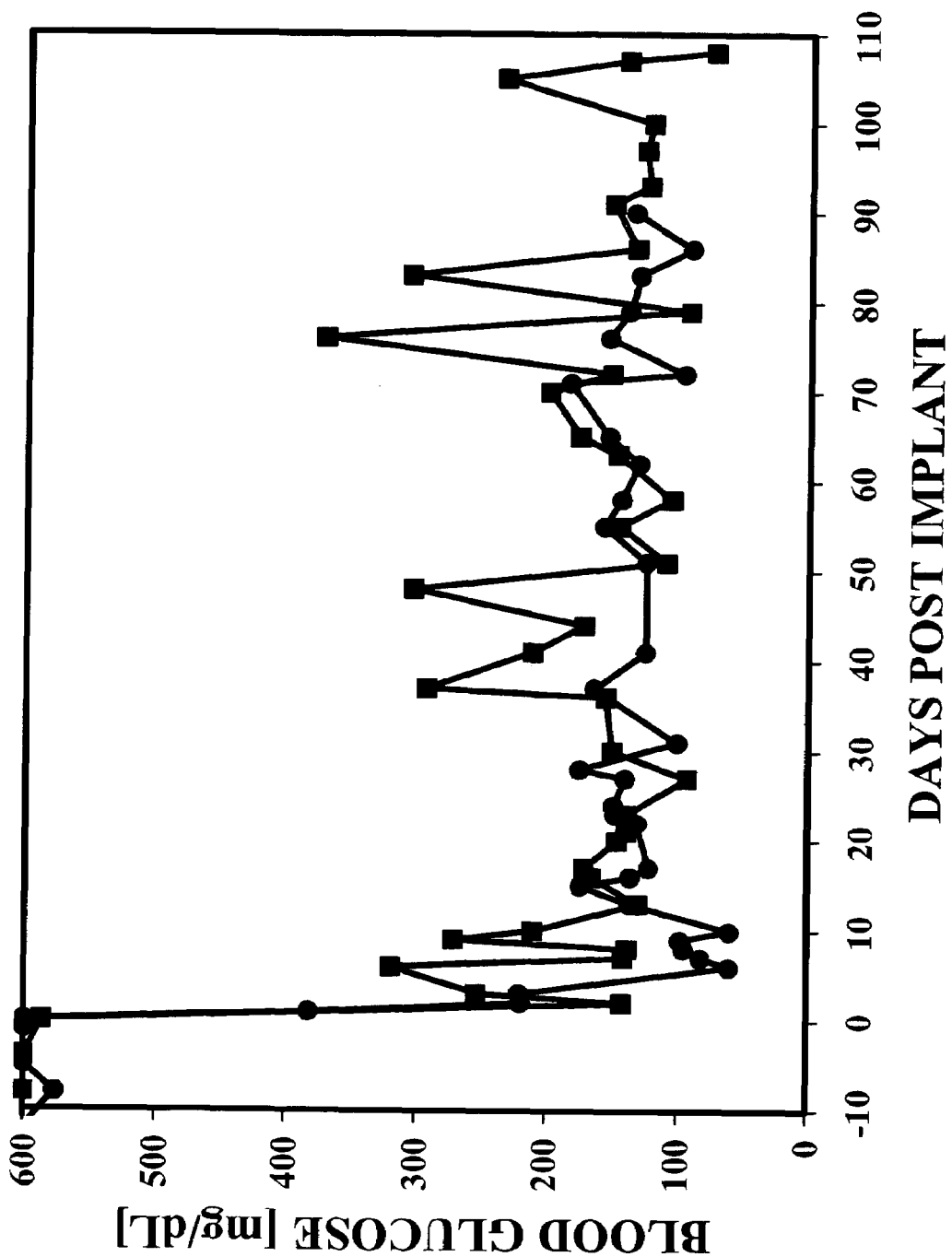
FIG. 9 is a graphical representation of the blood glucose levels measured in CD1 mice in which conformally coated mouse islet allografts were implanted at the intraperitoneal site.

Conformally coated mouse islet allografts were also implanted into CD1 mice in both the IP and SQ sites, respectively. FIG. 9 illustrates the blood glucose levels measured in two CD1 mice in which conformally coated mouse islet allografts [3300 IEQ and 2160 IEQ] were implanted at the intraperitoneal site. The implantation of 3300 IEQ was able to quickly return blood glucose levels to normal and maintain this level up to 90 days post-implantation. The 2160 IEQ implant reduced the blood glucose levels from 600 mg/dL to 100-300 mg/dL with slow oscillations in the daily levels.

Figure 10:
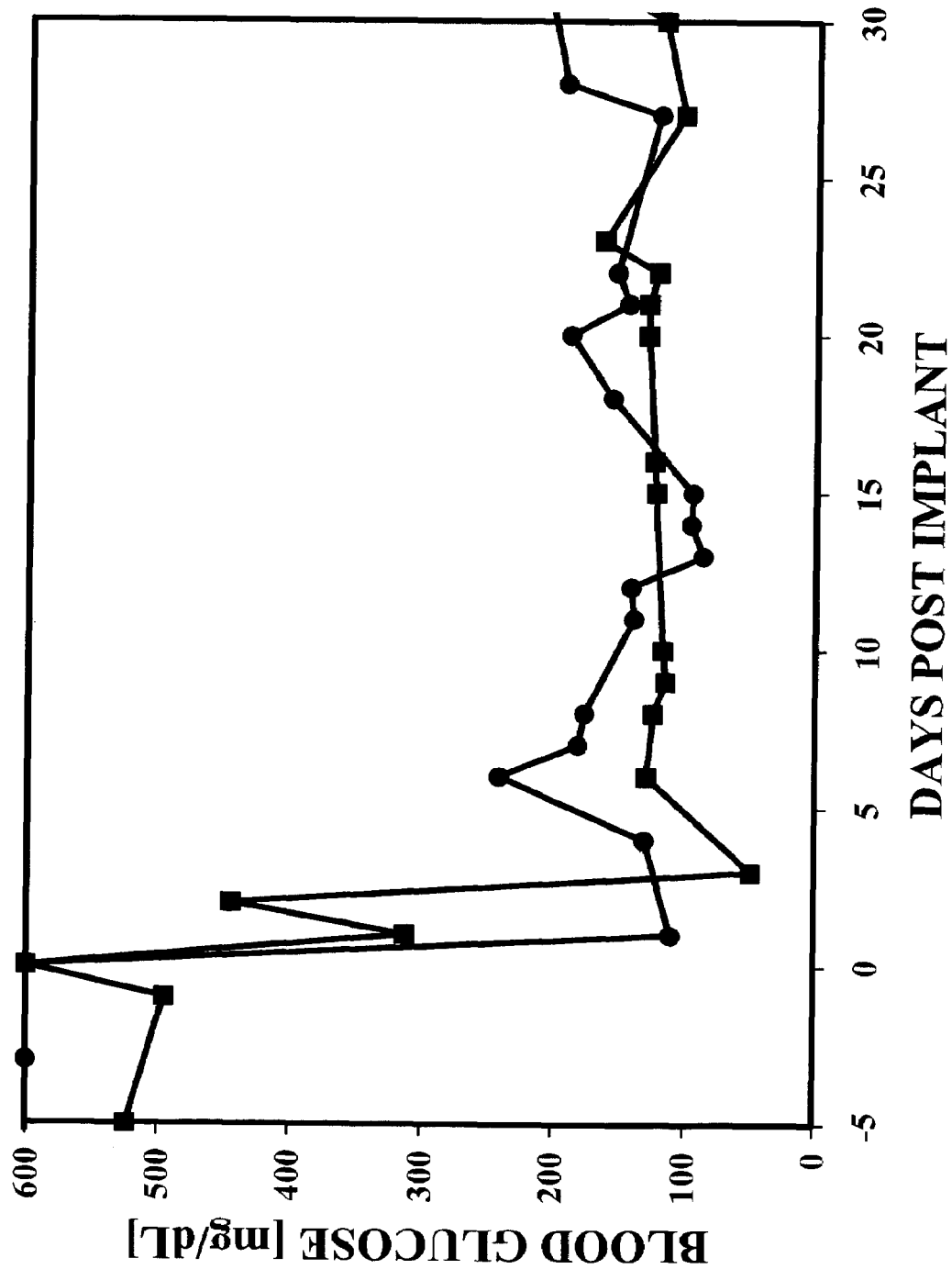
FIG. 10 is a graphical representation of the blood glucose levels measured in CD1 mice in which conformally coated mouse islet allografts were implanted at a high dosage in the subcutaneous site.

FIG. 10 illustrates the blood glucose levels measured in two CD1 mice in which conformally coated mouse islet allografts were implanted at a high dosage [3623 IEQ and 2000 IEQ] in the subcutaneous site. The 3623 IEQ implant was able to reduce the blood glucose level to near normal and maintain this level until day 35 post-implantation. The 2000 IEQ implant reduced the blood glucose levels to normal and maintained this level until day 30.

Figure 11:
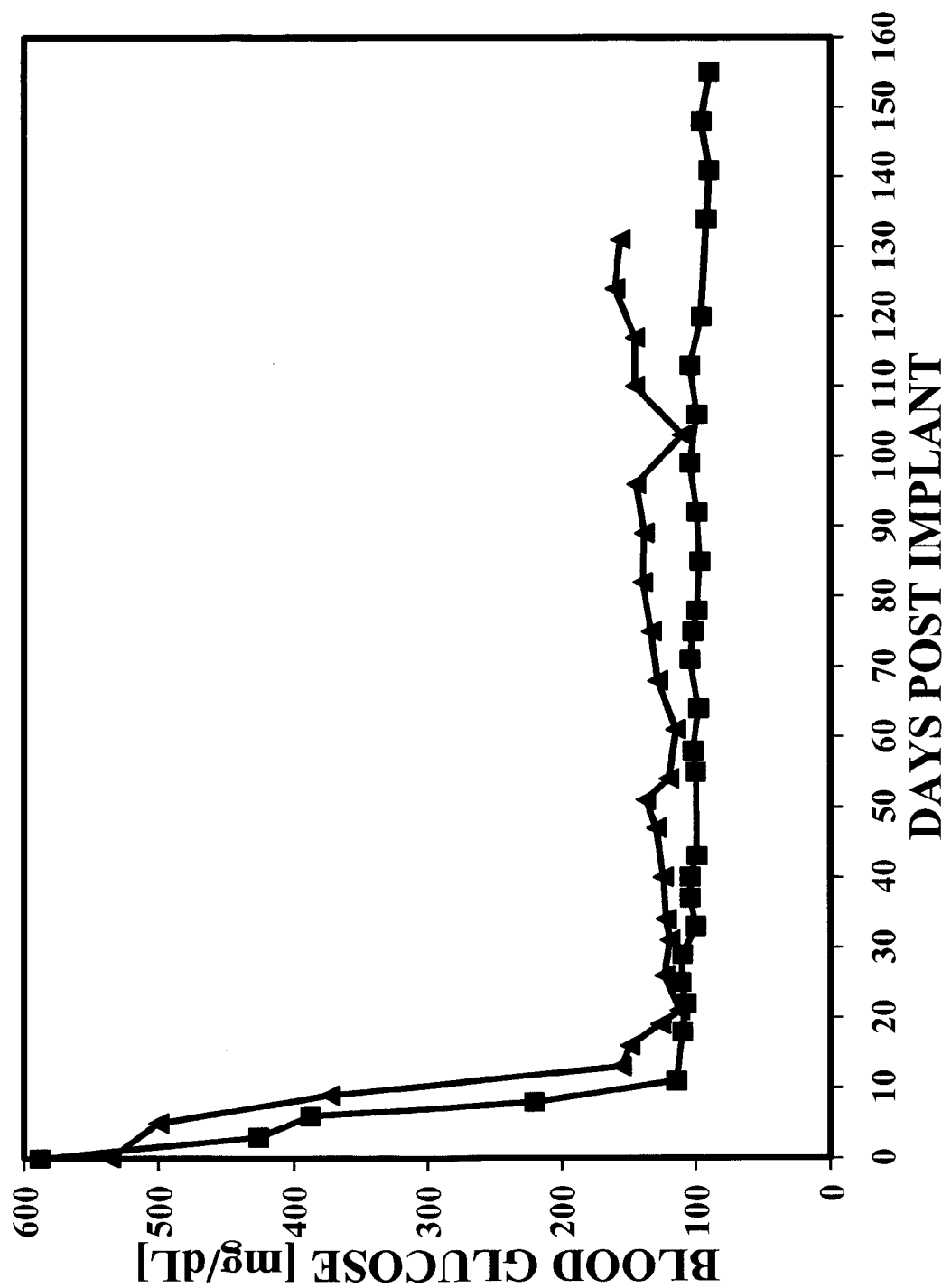
FIG. 11 is a graphical representation of the blood glucose levels measured in two diabetic NOD mice in which PEG conformally coated mouse islet allografts were implanted.

The conformal coatings protected against allograft immune rejection in both the IP and SQ sites. The uniformly minimal functional encapsulated islet dose was found to be ~1500 IEQ/mouse in the SQ site. Unencapsulated mouse islet allografts did not survive in the SQ site. PEG conformally coated mouse islets allografts were also implanted in NOD mice (600-700 islets per recipient). The conformal coatings not only protected against allograft immune rejection, but also protected against autoimmune recurrence of diabetes in this mouse model of Type I diabetes in humans. FIG. 11 illustrates the blood glucose levels measured in diabetic NOD mice in which PEG conformally coated mouse islet allografts were implanted.

Figure 12:
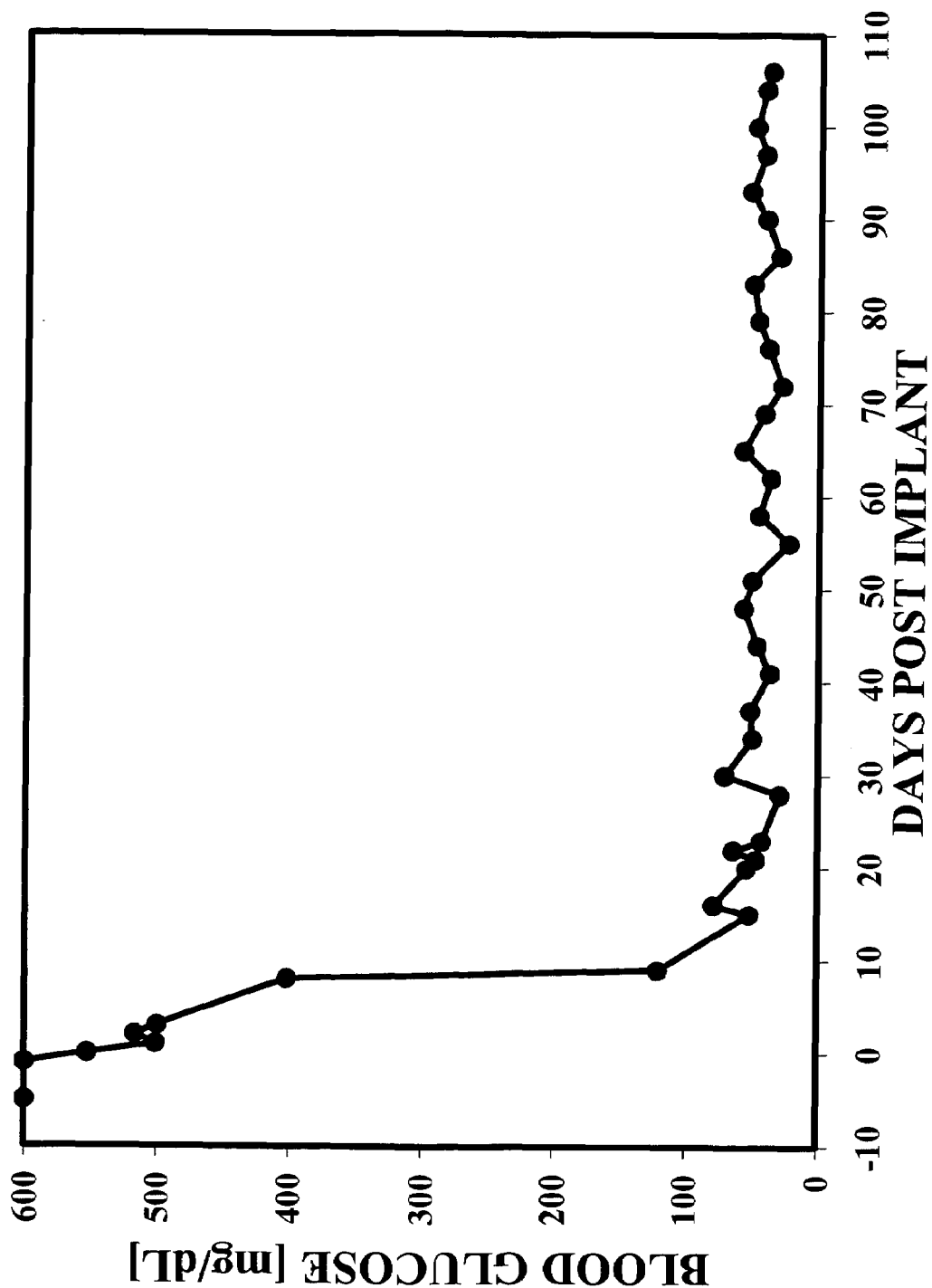
FIG. 12 is a graphical representation of the blood glucose levels measured in diabetic athymic mice in which conformally coated sub-human primate islets were implanted in the subcutaneous site.

FIG. 12 illustrates the blood glucose levels measured in athymic mice in which conformally coated sub-human primate islets [5,000 IEQ] were implanted in the subcutaneous site. The implant quickly reduced the blood glucose levels from above 600 mg/dL to ~35 mg/dL from day 15 until day 105 post-implantation.

Figure 13:
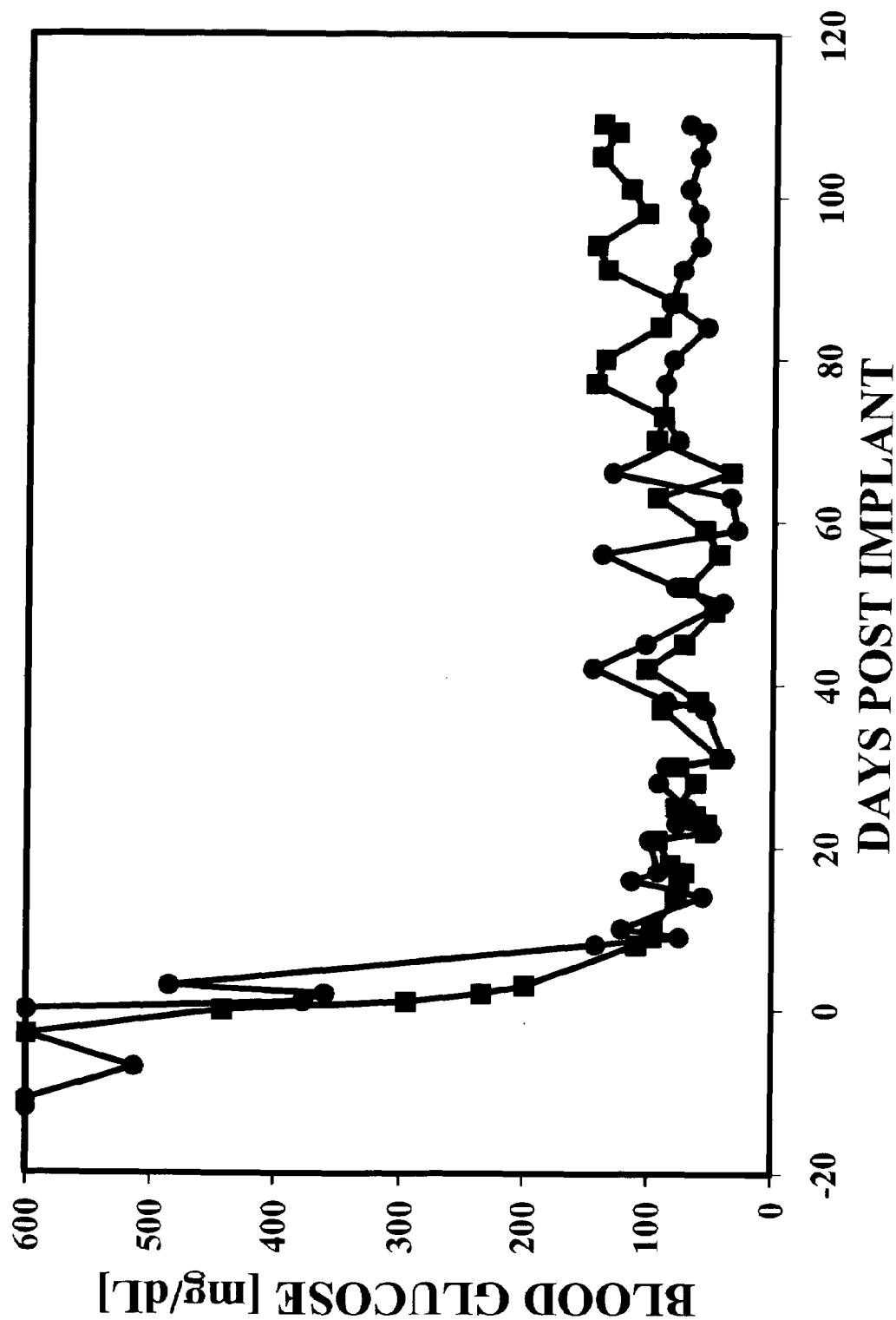
FIG. 13 is a graphical representation of the blood glucose levels measured in diabetic athymic mice in which conformally coated human islets were implanted in the intraperitoneal site.

FIG. 13 illustrates the blood glucose levels measured in two athymic mice in which conformally coated human islets [11,573 IEQ and 14, 688 IEQ] were implanted in the IP site. The implants reduced the blood glucose levels to normal and maintained this level up to 110 days post-implantation.

Figure 14:
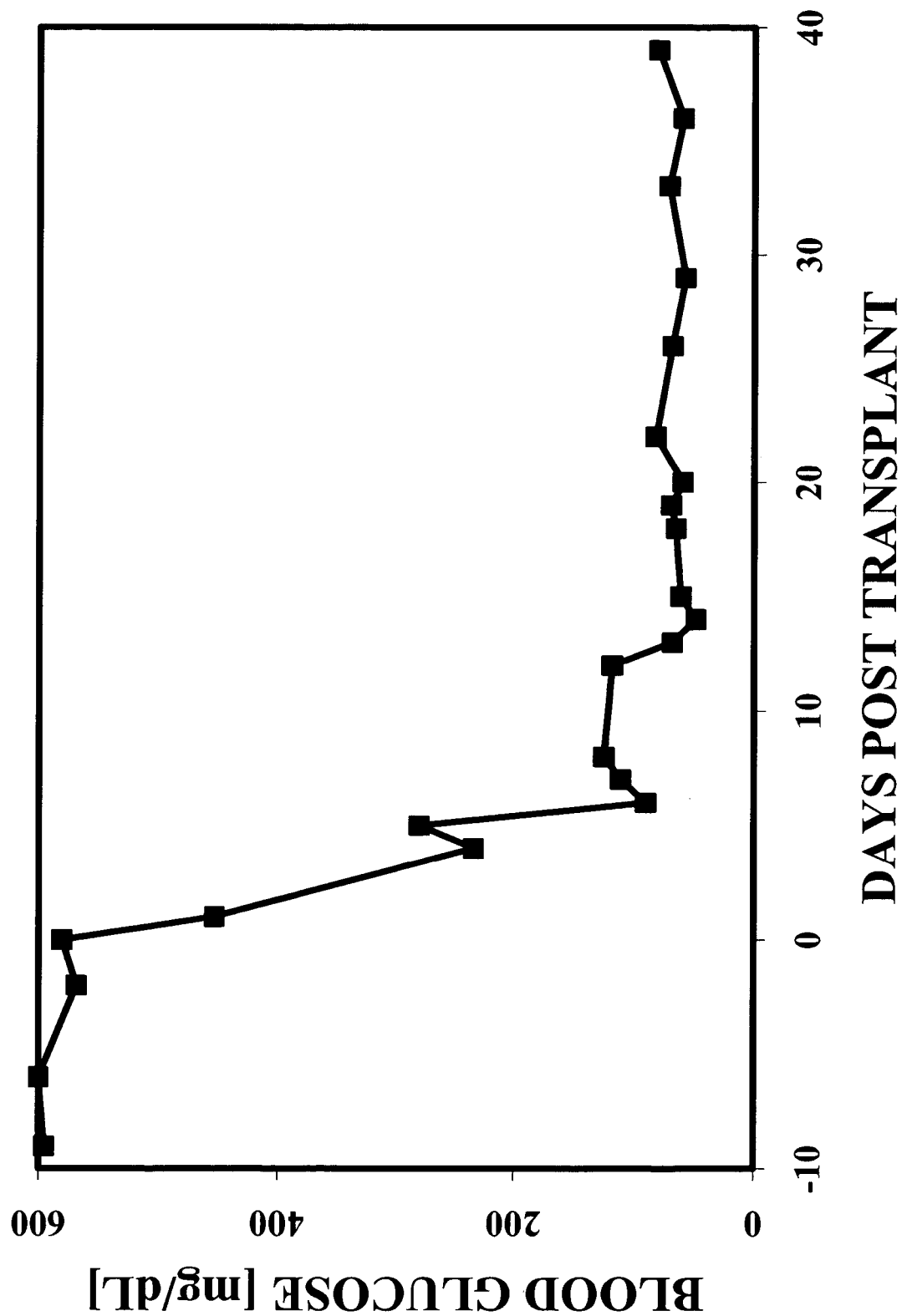
FIG. 14 is a graphical representation of the blood glucose levels measured in diabetic athymic mice in which conformally coated human islets were implanted in the subcutaneous site.

FIG. 14 illustrates the blood glucose levels measured in an athymic mouse in which conformally coated human islets [10,000 IEQ] were implanted in the SQ site. The implants have reduced the blood glucose levels to normal and have maintained this level up to 40 days post-implantation These results have shown that conformally coating both sub-human primate and human islets permitted survival of the islets in both the IP and SQ sites of athymic mice.

Example 6

Subcutaneous Implant of Encapsulated Islets in Cynomolgus Primates

Recipient Primate Subjects

Figure 15:
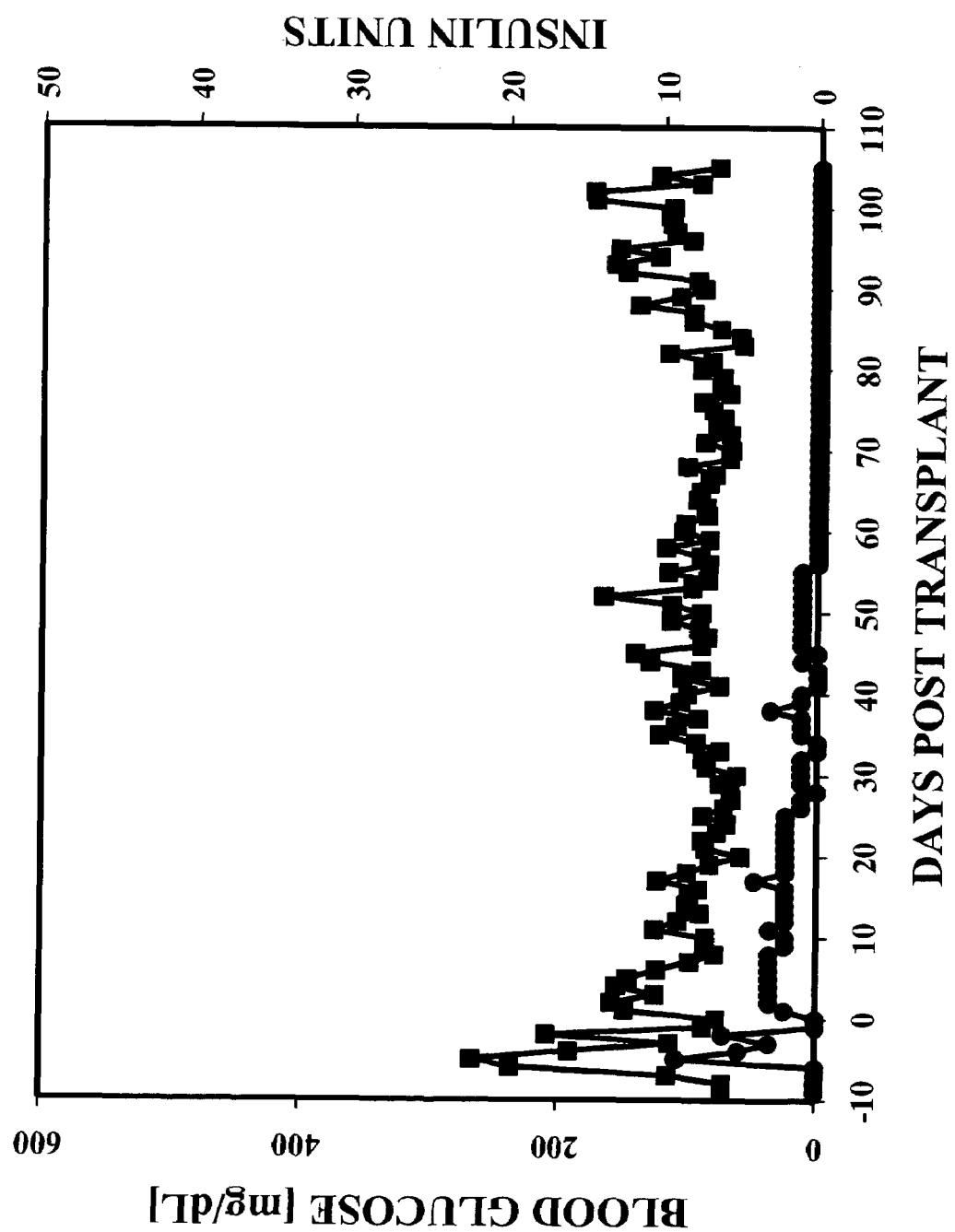
FIG. 15 is a graphical representation of the glucose levels and insulin requirements of partially pancreatectomized Cynomolgus primates following subcutaneous implantation of PEG conformally coated islet allografts.
Figure 16:
FIG. 16A is a histological photograph of subcutaneous implants of encapsulated islet allografts after 100 days, following anti-insulin staining.
FIG. 16B is a histological photograph of subcutaneous implants of encapsulated islet allografts after 100 days, following anti-insulin staining.
FIG. 16C is a histological photograph of residual pancreas tissue from a partially pancreatectomized Cynomolgus primate, following anti-glucagon staining.
FIG. 16D is a histological photograph of residual pancreas tissue from a partially pancreatectomized Cynomolgus primate, following anti-glucagon staining.
Figure 16:
Figure 16:
Figure 16:

A normal Cynomolgus primate was partially pancreatectomized (95%) prior to a subcutaneous implant of conformally coated islet allografts. FIG. 15 illustrates the glucose levels and insulin requirements of the partially pancreatectomized Cynomolgus primate for 10 days before and 105 days after subcutaneous implantation of PEG conformally coated islet allografts. The animal began with normal blood glucose levels without the need for any supplemental insulin. A few days after partial pancreatectomization the blood glucose levels increased to 300 mg/dL with an accompanying need for insulin to reduce the level to normal. Upon subcutaneous implantation of PEG conformally coated islet allografts the blood glucose levels decreased but not to the previously normal levels. Insulin was needed for several days after implantation but the amount was slowly reduced until 55 days post transplant when insulin shots were no longer required to maintain the blood glucose levels. From day 55 to day 105 post transplant, the blood glucose levels in the primate were slightly elevated over the baseline levels before the partial pancreatectomization; however, the levels were maintained by the implanted PEG coated islets without the need for insulin shots.

At necropsy, well-granulated encapsulated islets were found in the subcutaneous site with minimal host reaction. Glucose and insulin staining was demonstrated in the capsules containing islet tissue (FIG. 16A-D). Many encapsulated islets were devoid of islet tissue, which presumably were destroyed following implantation. Inflammatory cytokines from the surgical insertion and from an allograft response involving those capsules violated by the host. While one of the limitations of the partially pancreatectomized model of diabetes in young primates was the potential for the residual pancreas to recover from diabetes by expansion of the remaining islet tissue, there was little evidence of islet expansion in the form of enlarged islets in the residual pancreas.

Since partial pancreatectomy results in a variable diabetes model in primates with the potential of spontaneous recovery from the islets remaining in the head of the pancreas, streptozotocin was used to induce diabetes. The next four consecutive recipients all had diabetes induced by intravenous injection of streptozotocin.

Induction of diabetes in the other implanted animals was accomplished by the intravenous injection of Streptozotocin dissolved in saline at the dose of 150 mg/kg. The normal Cynomolgus primates were monitored with glucose tolerance testing for 1 week prior to the induction of diabetes by a streptozotocin injection. After 3-4 weeks of diabetes, glucose tolerance testing was performed again prior to islet implantation. Two diabetic Cynomolgus primates were kept diabetic as controls without receiving encapsulated islets. There was a rapid loss of blood glucose homeostasis with levels reaching 500 mg/dL. Large doses of insulin were required to reduce the blood glucose levels to near normal. The blood glucose levels had large oscillations with an accompanying need for insulin shots. There also were several episodes of significant low levels of blood glucose or hypoglycemia. The animals were unable to maintain normal, constant levels of blood glucose, even with daily insulin shots. Injections of streptozotocin caused rapid destruction β-islets with the animals unable to maintain blood glucose homeostasis.

Islet Implants

After a Ketamine, zylozine, and atropine injection, the abdomen of the Cynomolgus primate was shaved, prepped, and draped for the sterile injections. A 14-gauge intracatheter was inserted under the skin on either side of the midline. The needle was removed, replaced by a trochar, and 4-5 pockets were made laterally from the insertion sight in radial directions by forcing the trochar into the subcutaneous tissue. After the pockets were made, the trochar was removed, leaving the catheter in place. The encapsulated islets were pooled from the flasks and loaded into a 10 ml syringe that was attached to the inserted subcutaneous catheter. Different passages were made into the created subcutaneous pockets while injecting the encapsulated islets into these subcutaneous sites by moving the catheter into each space. A 4-0 prolene purse string suture sealed the injection site in the skin. This encapsulated islet injection procedure was repeated in each recipient, as necessary, along both sides of the midline until all the encapsulated islets were completely injected. The recipient was allowed to recover and returned to its cage for additional glucose monitoring.

Drug Treatment

No drugs were given to the partially pancreatectomized recipient and one of the Streptozotocin recipients. Low dose cyclosporine was given to three of the four Streptozotocin recipients of encapsulated islet allografts from day −7 prior before implant to day +30 after implant. The low dose Neoral cyclosporine (10-30 mg/kg/day) was given orally twice a day by squirting it into the Cynomolgus primate cheek pouch at feeding time. The 12-hour trough level was kept within a range of 25-100 ng/ml by ELISA. This dose was determined to be unable to prevent renal allograft rejection in Cynomolgus primate.

Metabolic Testing

Daily AM fasting blood glucose and PM 2 hour postprandial blood glucose measurements were made using Accucheck monitors and averaged for the daily value. OGTT was performed by using 7 kcal/kg Boost & 2 gm/kg glucose in gavage under Ketamine, zylazine, and atropine anesthesia. Samples were taken for glucose and C-peptide measurements at 0, 30, 60, 90, & 120 minutes.

Necropsy

The partially pancreatectomized animal was necropsied at 100 days post-implant. All major tissues were removed and processed for histological evaluation.

Assays

Accucheck glucose monitors were used to collect the daily blood glucose levels. C-peptide was measured with an ELISA assay from Linco and a human C-peptide antibody confirmed to cross-react with Cynomolgus primate C-peptide at the 100% level. Glycated hemoglobin determinations were made by a radioimmunoassay test. Routine blood chemistries were run on all diabetics and recipients at regular intervals. Viability testing of encapsulated islets was performed by Fluorescein diacetate/Ethidium bromide (FDA/EB) assay.

Streptozotocin-Induced Diabetic Recipient without any Drug Treatment

Figure 17:
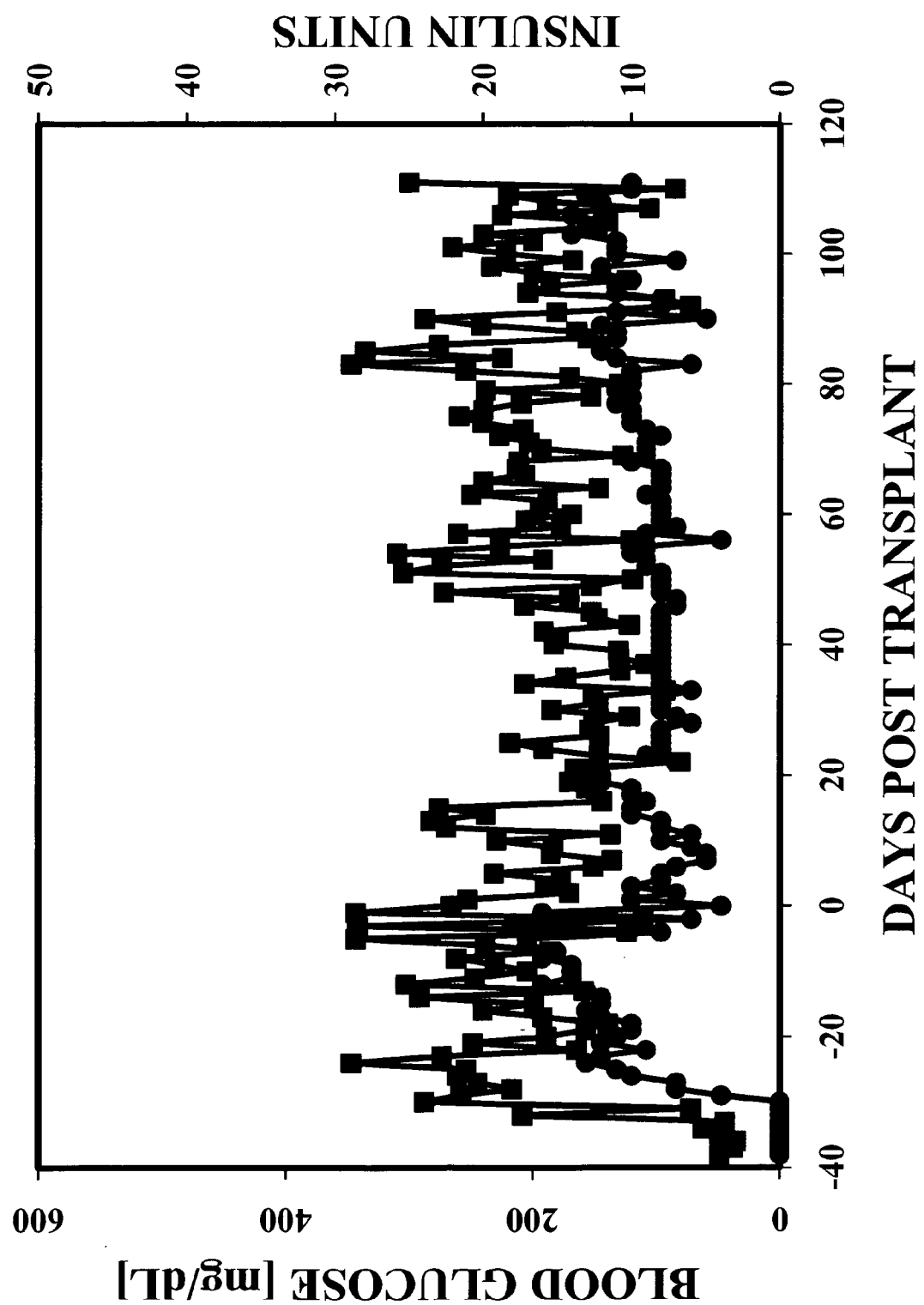
FIG. 17 is a graphical representation of the Blood Glucose levels (mg/dL) and Insulin requirements in a streptozotocin-induced diabetic Cynomolgus primate with a subcutaneous implant of an encapsulated islet allograft without immunosuppression drugs [♦=Blood Glucose, ●=Insulin].

The Streptozotocin-induced diabetic Cynomolgus primate recipients were severely diabetic (glucose: 150-350 mg/dL) and required 16-18 U insulin per day prior to implantation, which was more than the partially pancreatectomized recipient. There were typical wide excursions of the glucose levels as well as hypoglycemic episodes. The C-peptide values observed in these diabetic controls from glucose tolerance testing were very low and without response to glucose challenge. Encapsulated islets were implanted into the subcutaneous site without immunosuppressive drugs. The results for this Cynomolgus primate were shown in FIG. 17.

After subcutaneous implant, a 50% reduction in the insulin requirement was observed for 80-90 days, followed by some reduction of islet function. Although insulin independence was not achieved, C-peptide results from the OGTT were similar to pre-diabetic or normal values after implant, demonstrating functional implanted islets. This result would represent that seen in diabetic patients that have partial graft function following islet transplantation under full immunosuppression in clinical trials underway today.

Histologic evaluation of the recipient's subcutaneous implants showed encapsulated islets with insulin and glucagon staining scattered in the implant sites among many empty capsules. This raises the question as to why so many encapsulated islets were lost. One possibility was that the encapsulated islets that were breached by the host macrophages result in a focal allograft immune reaction around this violated capsule that also results in destroying the surrounding islets that were not breached by the macrophages. Instead, these encapsulated islets may be killed by the local cytokines coming from the immune cells reacting to the broken capsules. Another possibility was that there was not enough angiogenesis in this site so that many islets die soon after implant of hypoxia. A third explanation for many empty capsules was that the poor quality of the encapsulated Cynomolgus primate islets coming from the juvenile donors does not permit them to survive and function well in vivo. To answer some of these questions, different approaches were explored to improve these partial function results in this study.

Streptozotocin-Induced Diabetic Recipients with 30 days of Low Dose Cyclosporine The subsequent Streptozotocin-induced diabetic animals were as severely diabetic as the previous one. All animals received approximately 45,000 IEQ PEG conformally coated islets implanted into the subcutaneous site of the anterior abdominal wall. A low dose of cyclosporine was added from day −7 to day +30 in an attempt to reduce the focal allograft immune reaction that occurs around broken capsules and to determine if islet function could be improved. Low dose of cyclosporine was defined as a dose that results in 24 hour trough blood levels of 50-90 ng/ml of cyclosporine, which was below the immunosuppressive therapeutic dose of 100-300 ng/ml. After day +30, the low dose of cyclosporine was discontinued as the only drug given to the recipients (except for post-operative pain medication, insulin as required, and the Ketamine cocktail for testing procedures).

Figure 18:
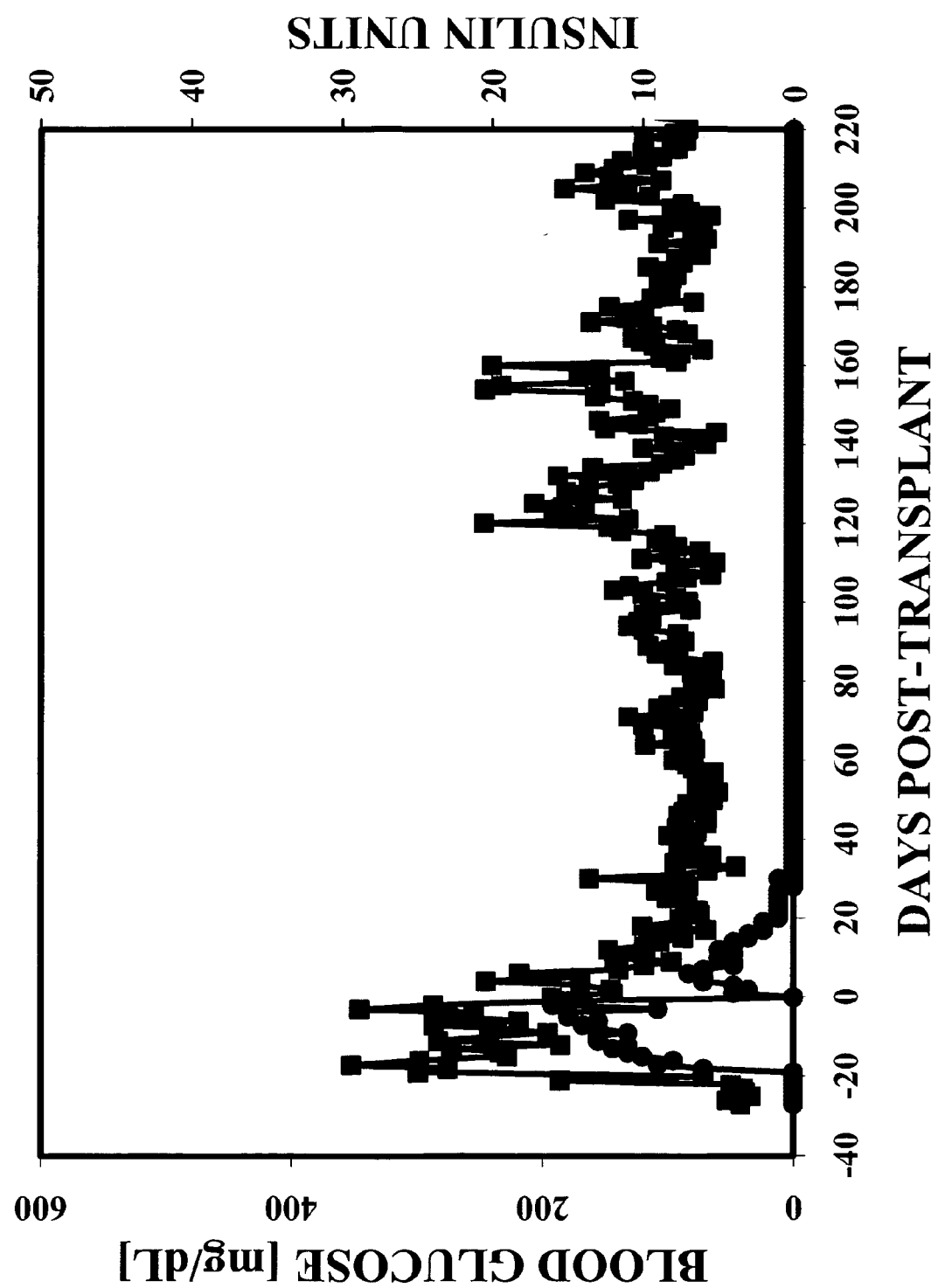
FIG. 18 is a graphical representation of the Blood Glucose levels (mg/dL) and Insulin requirements in a streptozotocin-induced diabetic Cynomolgus primate with a subcutaneous implant of an encapsulated islet allograft with 30 days of low dose cyclosporine and Metformin [♦=Blood Glucose, ●=Insulin].

The first recipient had a 50% reduction in glucose levels and insulin dosage during the first 10 days following subcutaneous implant. These values continued to decrease until insulin was discontinued at 30 days post-implant (the time of stopping cyclosporine) and remained with blood glucose levels between 75-150 mg/dL out to 220 days. The blood glucose results and insulin requirements are shown in FIG. 18.

At 120 days post-implant, some hyperglycemic values were obtained and Metformin dosing was started, returning the hyperglycemic values back to the normal range. Metformin is a Type II diabetes drug that reduces hepatic and muscular gluconeogenesis that is routinely used in patients with Type II diabetes. It is also used to improve glucose levels in Type I patients that are immunosuppressed for islet transplantation. This observation indicated that the implanted islets were at a reduced mass and were slowly losing function.

A second encapsulated islet allograft was implanted subcutaneously accompanied by another 30 days of low dose cyclosporine. The animal returned to normoglycemia for another 120 days. By 235 days from the first implant, higher glucose levels were observed, indicating diminished glycemic control, and low dose insulin was restarted. Over the next two months, the islets slowly lost function requiring full insulin treatment. Assuming the surviving islet dosage was on the margin to maintain this diabetic recipient long term, a second encapsulated implant was performed subcutaneously at 80 days post-implant under low dose cyclosporine levels for a second 30 day treatment. The blood glucose stayed at 150-225 mg/dL following the second implant and low dose cyclosporine treatment. Evaluation of the results of the OGTT demonstrates significant C-peptide release from the implanted islets even after the return to insulin therapy.

Figure 19:
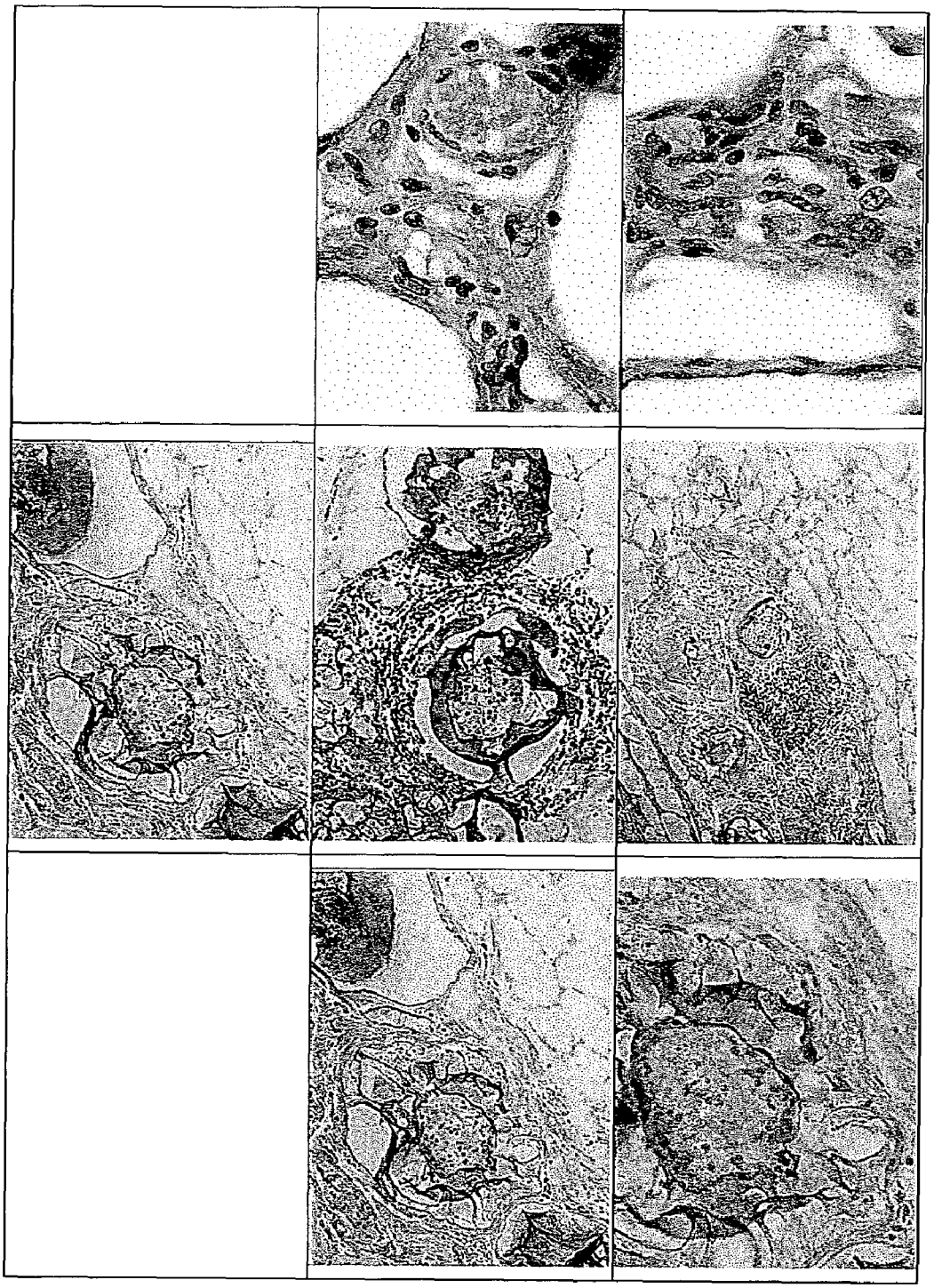
FIG. 19 is photographs of the histology of the subcutaneous implant site in Streptozotocin Induced Diabetic Cynomolgus primate an encapsulated islet allograft with 30 days of low dose cyclosporine and Metformin at 285 days

The animal was sacrificed at 285 days for histology evaluation as shown in FIG. 19. The histology samples from this animal exhibited many surviving islets in the subcutaneous site. There were some islets with focal lymphocytes around them without evidence of broken capsules. Their significance was unclear, but may suggest that these capsules were beginning to biodegrade at 9 months after implant. There also was clear evidence of many capillaries adjacent to the capsules. The encapsulated islets line up within the trochar-induced pockets in the subcutaneous site. There was observed, but there were no foreign body giant cells or other evidence of ongoing inflammation for most encapsulated islets.

The third diabetic Cynomolgus primate was implanted with encapsulated islets and received 30 days of low dose cyclosporine.

Figure 20:
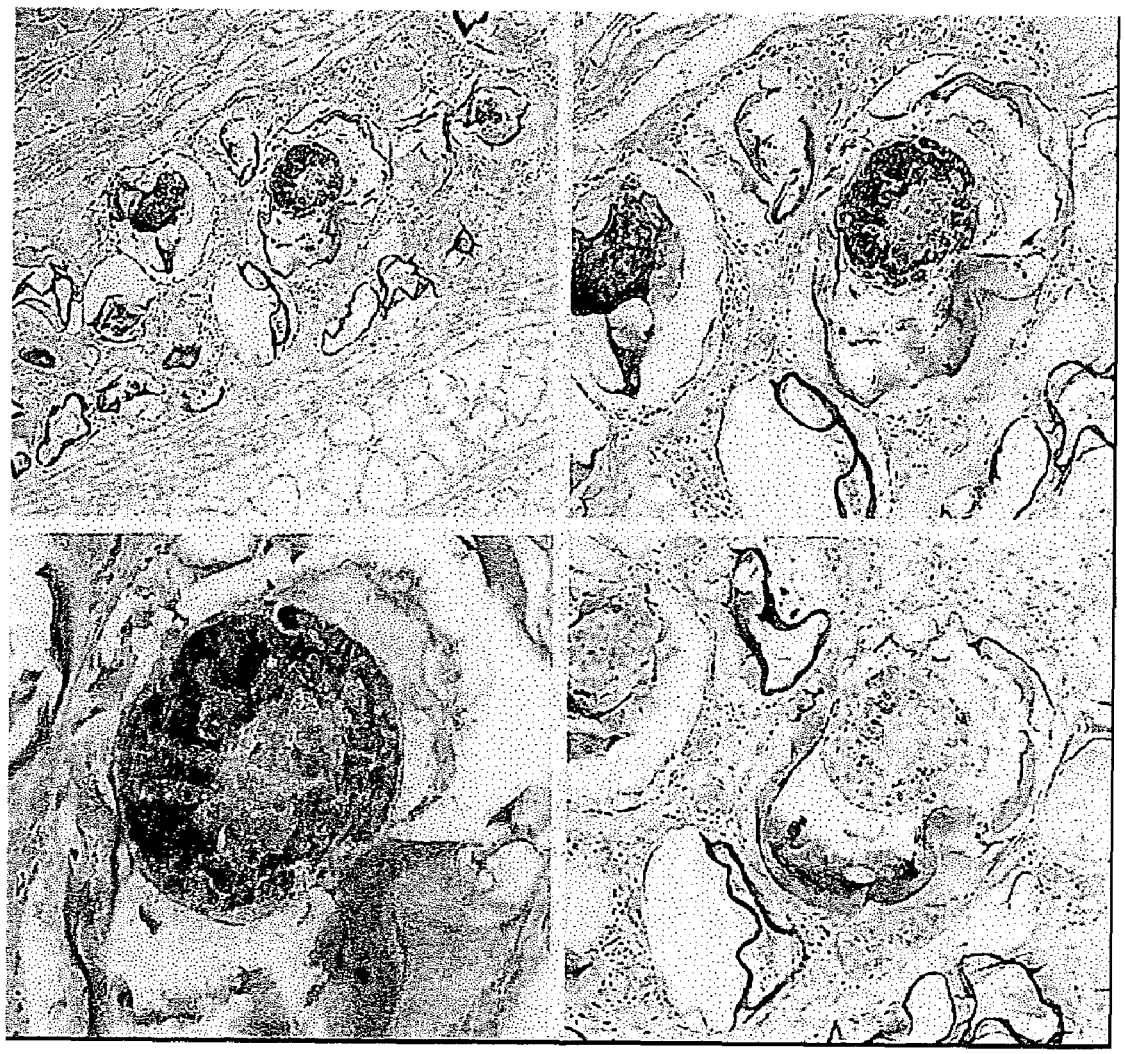
FIG. 20 is photographs of the histology of the subcutaneous implant site in Streptozotocin Induced Diabetic Cynomolgus primate with an encapsulated islet allograft with 30 days of low dose cyclosporine and Metformin at 248 Days, following anti-insulin staining.

It was difficult maintaining the cyclosporine 24-hour trough levels at the low dose target in this animal, and evidence of cyclosporine toxicity to the islets was observed after the first implant. Once the cyclosporine was stopped on day +30, the insulin requirement rapidly fell to a low level with normal blood glucose values observed for a short time. At 120 days, the insulin requirement began to increase, so a second implant with low dose cyclosporine was performed, stabilizing the insulin requirement at 50% of the pre-implant requirement. Insulin requirement began to increase approximately 230 days indicating diminishing glycemic control. C-peptide responses demonstrated ongoing encapsulated islet graft function, despite the return to insulin therapy. This animal was sacrificed at 248 days and the histologic findings are shown in FIG. 20.

At low power, the encapsulated islets were lined up in the micro-pocket made by the trochar during insertion. There were many surviving encapsulated islet allografts in these sites, as well as a number of empty capsules. Occasional encapsulated islets were also observed that had been recently surrounded by the host with a ring of lymphocytes and macrophages. Examination at higher power, showed many of these islets had excellent histology, including strong insulin staining of the islets. Some capsules appeared empty and had lost the islet cells at some time. Examination of the implant site at high power, showed there was ubiquitous evidence of capillaries at high density throughout the implant site surrounding the encapsulated islets. This capillary bed surrounded the outside of the PEG coatings in most directions at a markedly increased density compared with capillaries in the surrounding non-implanted subcutaneous site. The new capillaries associated with the encapsulated islets may have been stimulated to develop in response to signals coming from the encapsulated islet graft, and explained the ability of these encapsulated islets to continue long term islet function. The empty capsules were probably due to the islets being unable to support themselves prior to angiogenesis over the first few weeks following islet implantation. Also, there might have been cytokine damage in close proximity to these capsules from early immune reactions to capsules violated by the host.

The fourth Streptozotocin diabetic Cynomolgus primate also was implanted into the subcutaneous site using low dose cyclosporine. Two separate subcutaneous implants, 2 weeks apart, were initially performed to achieve insulin independence in this animal, which was achieved at 30 days. At approximately 115 days post-implant, insulin treatment was restarted due to rising glucose levels. Another subcutaneous implant was performed under low dose cyclosporine. After a temporary improvement, hyperglycemia returned along with increasing insulin requirement. C-peptide responses were observed during OGTT performed throughout the time of insulin independence, as well as, after return to partial islet function. The histology from this recipient was similar to the others with many capsules containing healthy islets and others without cells. Some capsules were ringed with lymphocytes.

Results of Oral Glucose Tolerance Testing

The C-peptide values in 4 Cynomolgus primates were measured at different times: a] prior to the induction of diabetes (Baseline), b] after induction of diabetes (Pre-Transplant), c] 30 days after encapsulated islet implant, d] 60 days after encapsulated islet implant, and e] 90 days after encapsulated islet implant. Prior to the gavage of the Boost and glucose, the pre-dose C-peptide was ~2.5 ng/ml, which were elevated compared with historic values of pre-dose samples done in recipients without Ketamine. Following the gavage, the mean values remained essentially the same, although some animals began to elevate their peripheral blood C-peptide response. By 120 minutes after gavage, the mean value significantly increased to nearly 4 ng/ml. At least 3 weeks following Streptozotocin, none of the four diabetic Cynomolgus primates increased their C-peptide in response to the OGTT challenge. The very narrow ranges of the standard deviations from the glucose challenges during the diabetic state confirm this lack of C-peptide response. The absolute values of the C-peptides during the diabetic state were at variance to some reports in the literature. This may be due to the six available C-peptide kits from different manufacturers vary in the cross reactivity of the human C-peptide to the Cynomolgus primate C-peptide from 30% cross reactivity to 100% cross reactivity. The antibody used by Linco has been shown to be 100% cross-reactive. Following subcutaneous islet implants in all four diabetic recipients, in spite of different insulin requirements at 30 days, the C-peptide levels increased significantly at each time point compared to the diabetic state. This was also true for 60 days post-implant. There was no significant difference in these four recipients comparing their normal baseline C-peptide responses to those following subcutaneous islet implants at 30 and 60 days post-implant.

Glycated Hemoglobin Results

Figure 21:
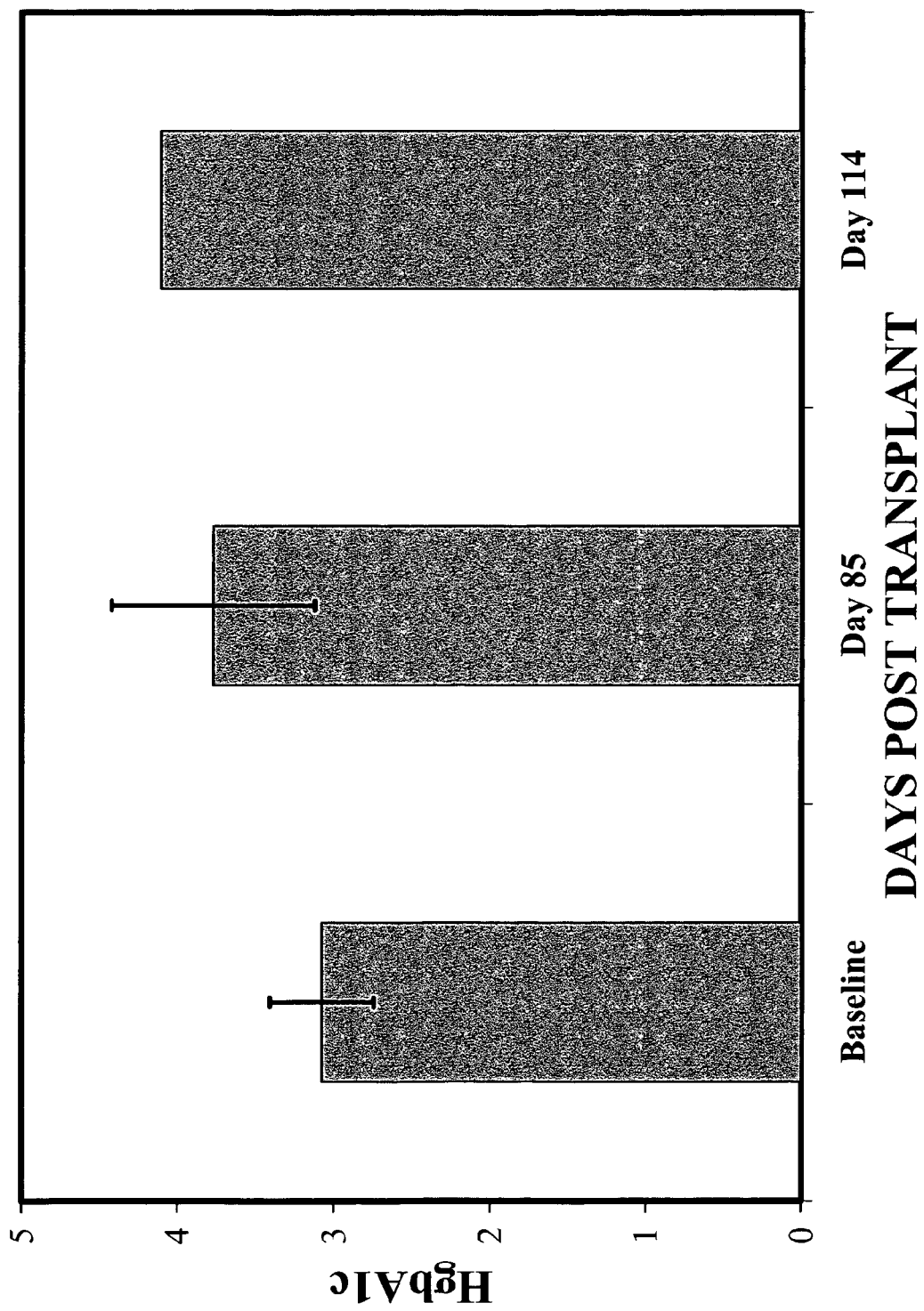
FIG. 21 is a graphical representation of glycated hemoglobin values from Cynomolgus primates prior to the induction of diabetes (Baseline, n=4), and 85 days, n=3; and 114 days, n=1 after transplant.

FIG. 21 illustrates the glycated hemoglobin values from Cynomolgus primates prior to the induction of diabetes (Baseline, n=4; after 85 days, n=3; and after 114 days, n=1). Since glycated hemoglobin levels measure a protein that lasts 90 days, little information was gained in testing prior to that date. Baseline values of 3.0 HbgAlc were obtained in these four primates prior to the induction of diabetes. At 85 days post-implant, repeated glycated hemoglobin values were slightly elevated to 3.8, but the increase was not significant. A reading in a single animal at 114 days was slightly higher at 4.1. While little was known of Cynomolgus primate glycated hemoglobin values, the results at 85 days not only include the 30 days of diabetic values with significantly elevated glucose values but also 85 days post-implant without significant elevation over the baseline values. This was in spite of evidence of some hyperglycemia noted in the daily glucose values.

Summary of Subcutaneous Implant of Encapsulated Islets in Cynomolgus Primates

Implanting PEG conformally coated islet allografts into the subcutaneous site of four Streptozotocin-diabetic Cynomolgus primates demonstrated that nearly normal blood glucose levels were obtained with the elimination of insulin treatment for up to 120 days without the need for long-term immunosuppression. The use of low-dose cyclosporine for the first 30 days after implant increased the percent of surviving encapsulated islets in the subcutaneous site in all three of the recipients receiving it compared to the one that did not receive it which had partial function of the implanted islets. Metabolic testing by an OGTT challenge of the recipients after subcutaneous implants of encapsulated islet allografts demonstrated that there were significantly increased C-peptide responses at all times following gavage compared to the diabetic values and C-peptide responses that followed subcutaneous implants of allografted islets were not statistically different from their normal responses prior to the induction of diabetes. The results of the Cynomolgus primate implant studies are summarized in Table 2.

TABLE 2

Cynomolgus Primate Implants

Positive Factors

Biocompatibility is excellent
Islets survive encapsulation & function
Subcutaneous site works
Cyclosporine helps with early loss of islets
Coatings provide immunoprotection long term
Re-transplant can be done without difficulty
Residual C-Peptide confirms partial function after loss of insulin independence
Encapsulated islets recovered at nearly 300 days
Evidence of vascularization of the encapsulated islets in subcutaneous site suggest mechanisms of long term function Example 7

Subcutaneous Implant of Encapsulated Islets in Baboons

Surgical Procedures

Baboon pancreata were removed from the donors, cannulated, and flushed with pancreas preservation solution and then shipped to Novocell for islet preparation and encapsulation. They were subsequently cultured, shipped to the holding facility for implantation, and then prepared for surgical implant by suspension in culture medium, using similar protocols as are proposed for human islet preparation. The baboons were anesthetized, and a 16 gauge catheter was placed into the subcutaneous site of the anterior abdomen. A trochar was inserted through the implanted catheter to create a "fan shaped" area of 5 subcutaneous tracts (~3" each in length) under the skin of the abdomen. The test material (~17% of the total islet implant in ~2.5 mL volume) was gently suspended, pulled into a 5 cc syringe, and deposited along the subcutaneous tracts (or "pockets") with an even pattern of deposition throughout the pockets. The needle insertion site was closed with a 4-0 purse string suture to prevent any leakage from the insertion site. This resulted in long, low lying areas of test material and buffer. The liquid portion was quickly resorbed and left a slightly granular surface texture. A total of 6 sites were used for the complete implantation procedure. The area was tattooed to mark the injection site location. No local reaction was noted indicating inflammation.

Drug Treatments:

Cyclosporine (at a sub-immunosuppressive dosage with 24 hour trough levels from 50-95 ng/ml) was administered on days −7 through +30 post-implant. Cyclosporine was administered to prevent collateral loss of encapsulated islets due to immediate focal allograft immune response to some weakly encapsulated islets in the implant. Additionally, to mimic clinical concomitant medications, metformin was administered starting on day +1 and throughout the duration of the study. The dose of coated islets delivered at least 4 weeks post streptozotocin administration to induce diabetes was approximately 40K IEQ/kg body weight. The difference between the effective islet dose used during our studies and the dose used in current human studies (15K IEQ/kg) was likely due to the implant site (subcutaneous vs. portal vein) and loss of islets following implantation.

Monitoring:

The aim of the in-life monitoring was to provide comprehensive assessment of information needed to track both diabetic management and implant activity, as well as standard indicators of local tolerance and global indicators of overall health/safety assessment. The groups were monitored during the pre-diabetic period (baseline), during the diabetic period, and post-implant. Pre-diabetic, diabetic and monthly post-implant measurements included OGTT and AST (Arginine Stimulation test) (with blood glucose, insulin and c-peptide assays), and hemoglobin Alc. Daily monitoring of diabetic and post-implant periods included blood glucose (fasting, 2 hour post prandial and pre-dinner), urinary glucose and ketones (morning fasting and pre-dinner), food intake (grams of carbohydrate, fat and protein), amount of insulin injected (diabetes management) and other medication doses. Weekly measurements included body weight and clinical observations.

Necropsy:

Histopathologic examination of the subcutaneous implant site and a non-implanted control site were performed using hematoxylin and eosin (H&E) staining and immunohistochemistry staining (insulin, glucagon, angiogenic actin, macrophages, and lymphocytes, CD3, CD4, CD8). Histopathologic examination of all standard organs and tissues were conducted using H&E staining and evaluated by a board-certified veterinary pathologist. Immunohistological staining of the pancreas was conducted to evaluate the presence of insulin and glucagon.

Encapsulated Islet Allograft in Streptozotocin Diabetic Baboons

Figure 22:
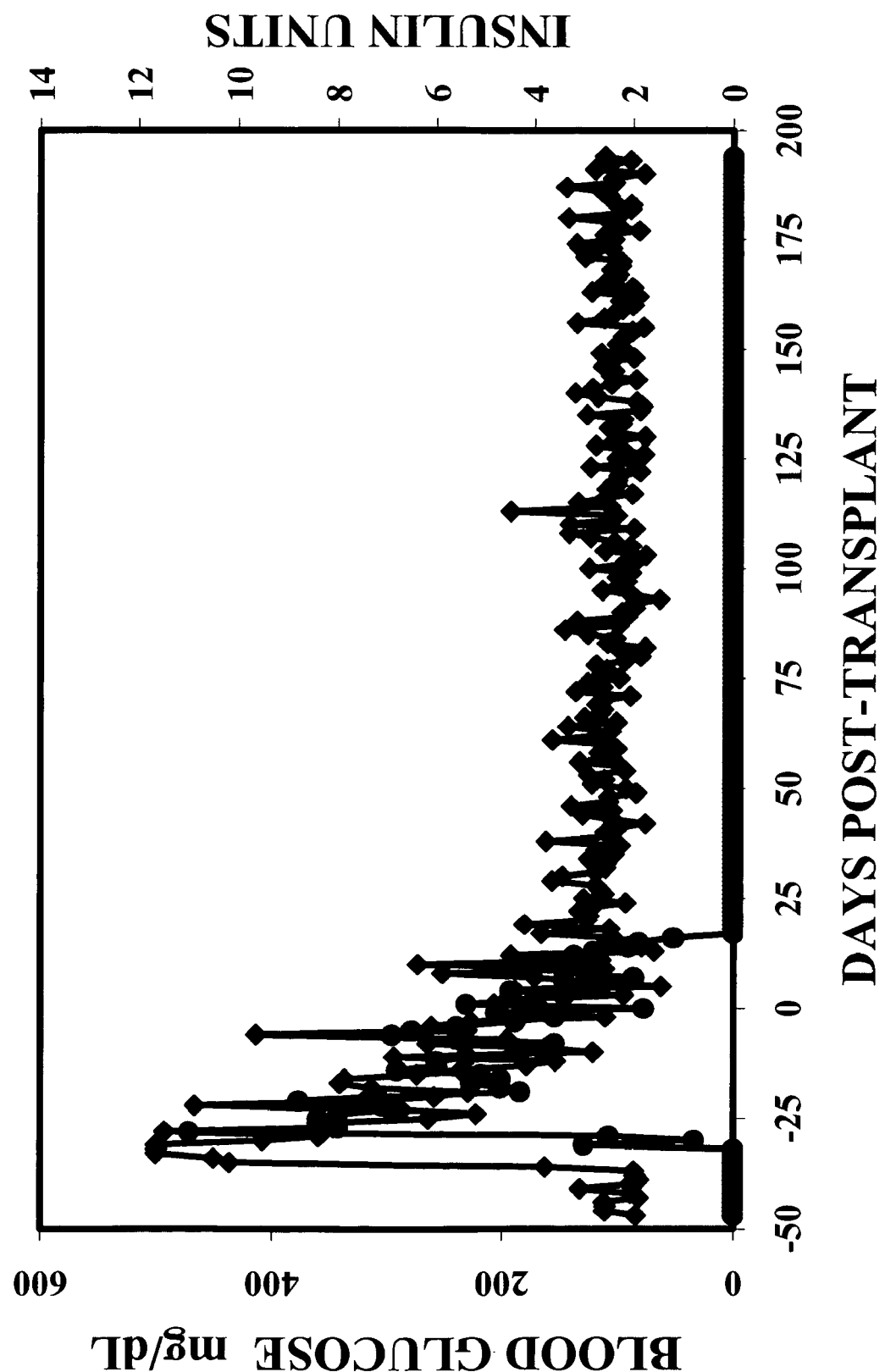
FIG. 22 is a graphical representation of the Blood Glucose levels (mg/dL) and Insulin requirements in a streptozotocin-induced diabetic baboon with a subcutaneous implant of an encapsulated islet allograft with 30 days of low dose cyclosporine and Metformin [♦=Blood Glucose, ●=Insulin].
Figure 23:
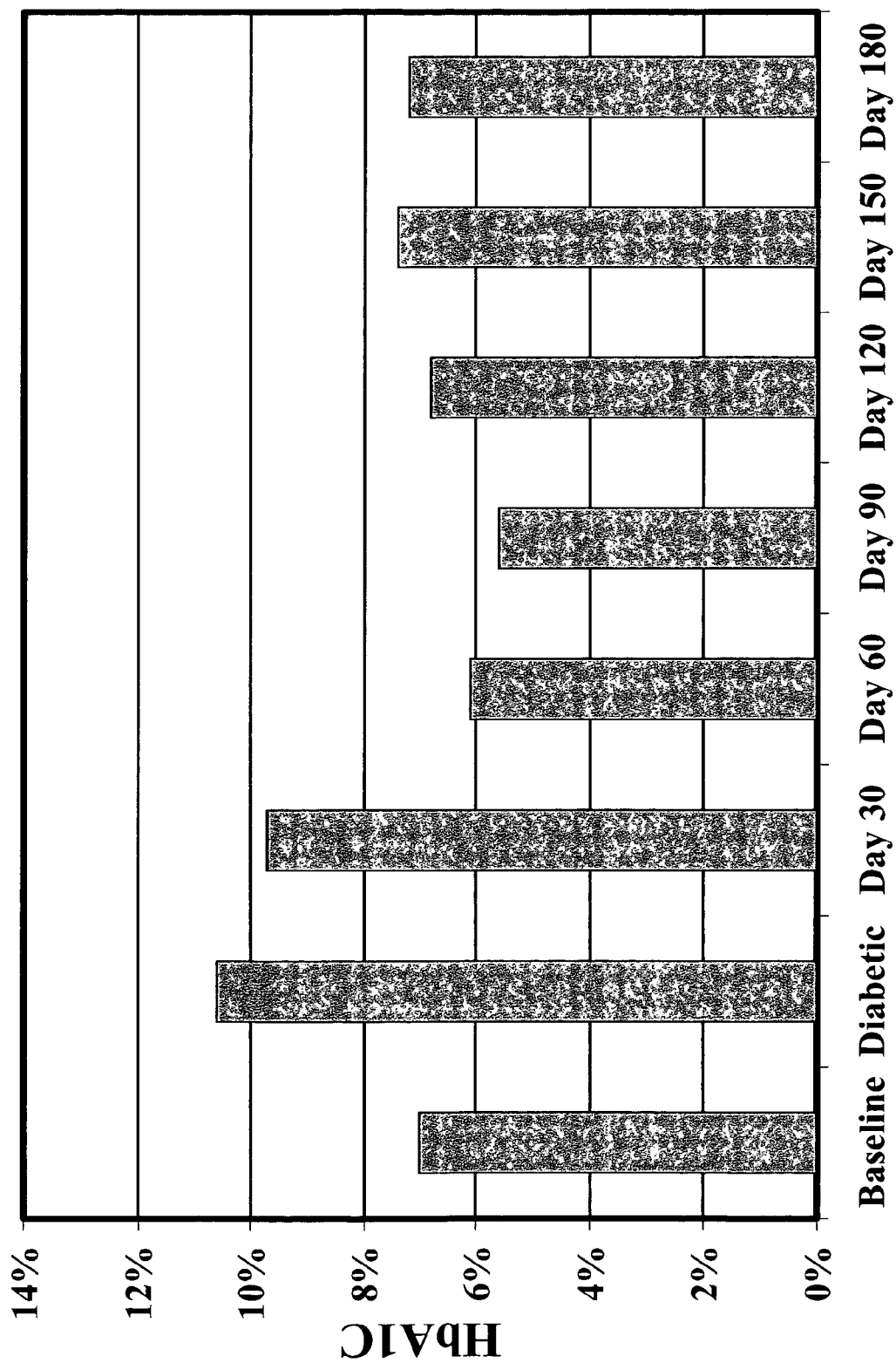
FIG. 23 is a graphical representation of Glycated Hemoglobin A1c in a streptozotocin-induced diabetic baboon with a subcutaneous implant of an encapsulated islet allograft with 30 days of low dose cyclosporine and Metformin.

FIG. 22 shows the early results of the first diabetic baboon implanted with encapsulated islet allografts in the study. This diabetic baboon recipient showed the ability to achieve insulin independence within 17 days after subcutaneous implantation of encapsulated islet allografts. This was in contrast to the Cynomolgus primate diabetics where none achieved insulin independence before 30 days after islet implantation. The baboon diabetic model was changed from using oral injected cylosporinen administration, as in the Cynomolgus primate, to IM injection in the large baboons. This eliminated the variances observed in the Cynomolgus primate model of 24 hour trough levels. FIG. 23 shows that this recipient achieved normal Hemoglobin A1c levels by 60 days post-implant and remained in the normal level through 180 days while continuing off insulin.

Results of the OGTT and AST demonstrated significant C-peptide release following all time points after implantation. The normal response showed a peak of C-peptide at the 30 minute time frame with the values decreasing thereafter resulting in normal glucose values at all time frames. During the diabetic time, the glucose values continued to rise throughout due to very low levels of C-peptide that were not responsive to the glucose challenge. Following the implantation, there were large responses of C-peptide to glucose challenge but these responses were delayed with peaks occurring at 60 and 90 minutes post-challenge. Examining the glucose values, the 30 and 60 minute values were higher than normal due to this delay in C-peptide responsiveness. However, by 90 and 120 minutes, the glucose values returned close to normal. At this time, it is not known whether this delay in C-peptide responsiveness was due to the subcutaneous site of implantation or to the encapsulation of the islets. These results were very analogous with implanted islets in the portal vein of human diabetics under immunosuppression.

A second baboon was implanted in the subcutaneous site again with low dose cyclosporine. A lowering of the glucose values occurred while maintaining nearly the same insulin requirement. The insulin requirement slowly dropped at the 100 day value, but slowly rose until nearly the 200 day period, while the glucose values remained lowered. Examination of the hemoglobin A1c values showed that partial function was clearly achieved by lowering the levels significantly from 12% to 8.0% by 90 days and to normal levels at 120 days. The values slowly rose to the 8% level where they remained at 180 days. These values showed a partial function that was compatible with those being achieved with islet transplant recipients that do not achieve insulin independence but who maintain near normal levels of hemoglobin A1c levels post-implant.

Examination of the OGTT and AST results showed lower C-peptide values and higher glucose values throughout the post-implant period compared to the first recipient. Yet, the C-peptide responses were significantly higher than the values obtained during the time of diabetes.

Figure 24:
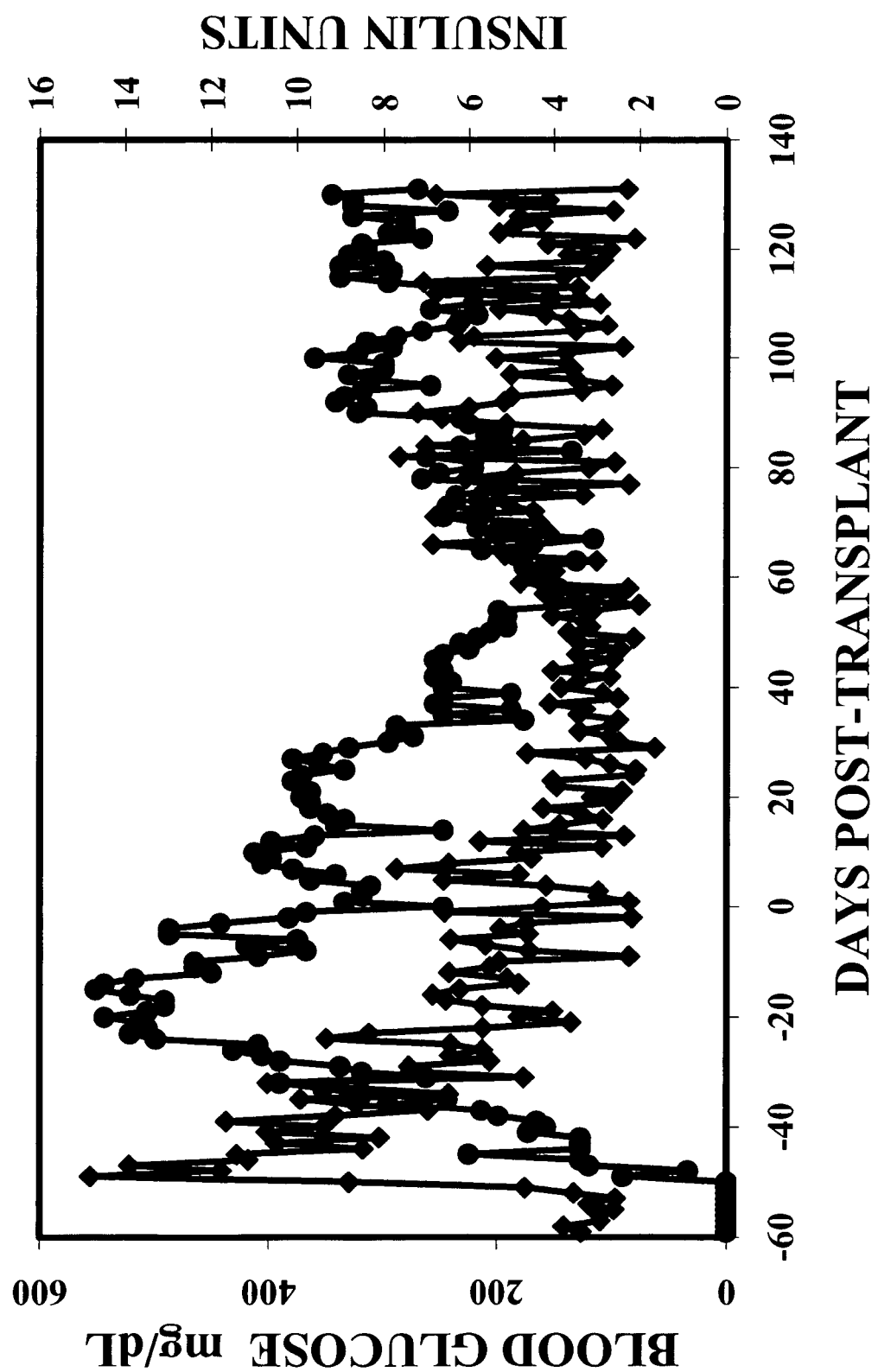
FIG. 24 is a graphical representation of the Blood Glucose levels (mg/dL) and Insulin requirements in a streptozotocin-induced diabetic baboon with a subcutaneous implant of an encapsulated islet allograft with 30 days of low dose cyclosporine [♦=Blood Glucose, =Insulin].

A third recipient also received encapsulated islet allografts in the subcutaneous site with low dose cyclosporine (FIG. 24). This recipient also demonstrated a partial response following implantation with over a 50% decrease in both the glucose and insulin values compared to the diabetic period. These values were maintained at 140 days post-implantation.

Figure 25:
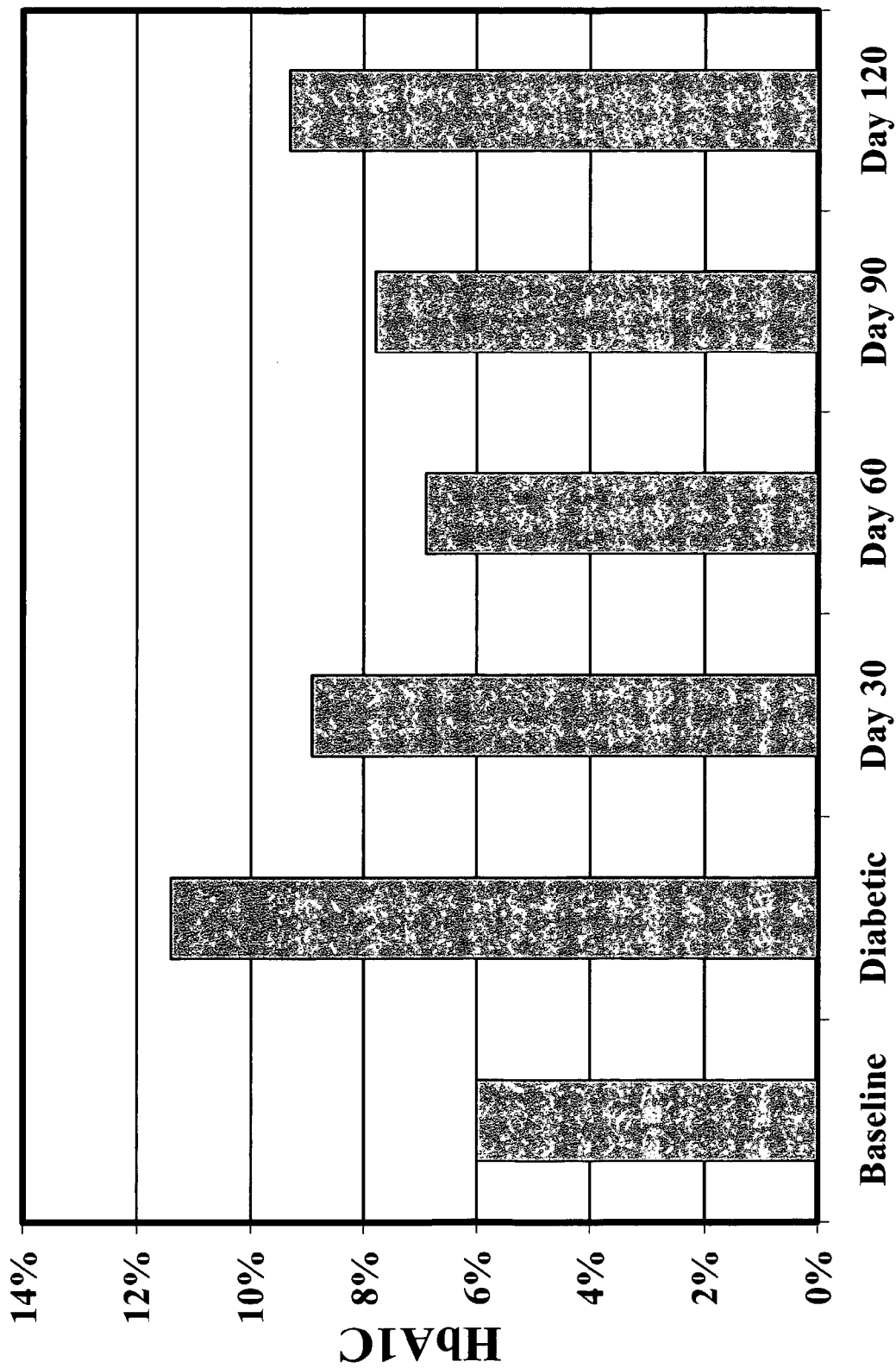
FIG. 25 is a graphical representation of Glycated Hemoglobin A1c in a streptozotocin-induced diabetic baboon with a subcutaneous implant of an encapsulated islet allograft with 30 days of low dose cyclosporine.

The hemoglobin A1c values (FIG. 25) for this recipient showed that it reached a normal range by 60 days post-implant, but rose to diabetic levels by 120 days. This again demonstrated a partial islet function for 90 days with reduced responsiveness after that time period.

The responses to both OGTT and AST were similar to those observed for the previous partially functioning recipient with elevated C-peptide values post-implant that peak in the 60 to 90 minute time frame.

With one normal islet transplant recipient and two partial recipients, it was important to understand how these results compared to those following implantation into the portal vein of a diabetic recipient. To accomplish this task, a pre-study baboon recipient that had been the first to receive encapsulated islets in the subcutaneous site at a time that was before the baboon islet isolation results had achieved acceptable levels was used for this study. This one recipient had been used to practice the logistics of shipping pancreases and the encapsulating islets for implantation. Two marginal subcutaneous encapsulated islet implants were performed with expected poor results. The recipient was kept on study and used to test the potential of an intra-portal vein injection of encapsulated islet allografts that had been isolated and encapsulated under similar conditions as those used in the first three recipients.

The first two marginal implants were performed at day 0 and at day 110. Both had transient improvements that did not last as expected from the marginal grafts that were implanted. But then on day 240 after the first implant, an intra-portal vein injection of encapsulated islet allografts was made without any significant rise in portal venous pressure or any change in liver function tests by a direct injection into the portal vein as a surgical procedure. There was a dramatic response to the implant with a greater than a 50% drop in the insulin requirement within a few days. After the cyclosporine was stopped at 30 days post-implant this recipient came off insulin treatment with normal glucose level to 290 days post-implant. Examining the hemoglobin A1c values for this recipient, a reduction followed the marginal subcutaneous implants, but not to normal levels. The only value obtained to date following the portal vein implant was taken at the 30 day post-implant time frame, which was too early to see the expected improvement. Hemoglobin A1c levels lag behind the clinical results by approximately 30 days in the baboon.

Following the marginal subcutaneous islet implants there were clearly low levels of C-peptide remaining that were clearly higher than the diabetic values, but this responsiveness was not able to normalize the hemoglobin A1c levels, although they were reduced. Only the 30 day values are available at this time following the portal vein implant. Examining the glucose response, there was a marked drop that was associated with a significant rise in C-peptide. The significant improvement in the first portal vein implant suggested the potential of enhancing the subcutaneous site to obtain improved results.

Example 8

Cells Encapsulated in Alginate Microcapsules with and without PEG

Cells and tissues may be coated in matrices containing alginate or other hydrogels. Preferred methods of coating islets in alginate microcapsules, with and without PEG, are described as follows.

Coating of Islets with Alginate Microcapsules

100 µl of cultured islets was suspended uniformly in 1.25 ml of a 1.6% sodium alginate solution in 10 mM HEPES buffer. Alginate microcapsules containing islets were produced by syringe pump/argon jet extrusion through a 21-gauge needle with argon pressure set at 10.5 PSI [72, 394.95 Pa (N/m2)], and collected in 100 ml 80 mM calcium chloride in 10 mM HEPES solution. The alginate microcapsules were washed three times with M199 by settling with gravity for 15 minutes and decantation. The alginate microcapsules had a size distribution from 250-350 µm.

Coating of Islets Containing Alginate Microcapsules with PEG

Fifteen milliliters of 20 mM low ionic HEPES buffer (containing 1.8 mM $CaCl_2$ and 260 mM Manitol, pH=7.0) was added to a 15 ml conical tube containing 100 µl of islets containing microcapsules. The tube was centrifuged to form a pellet, supernatant was removed, 15 ml of Den-EY solution (0.1 mg/ml in low ionic HEPES buffer) was added into the pellet, and the tube was kept horizontal for 10 minutes at room temperature. The stained islets were washed with low ionic 20 mM HEPES buffer, which was sparged with Argon for at least 30 minutes. The stained islets were mixed with 20 ml of photoactive polymer solution, which was sparged with Argon, and pre-equilibrated to 8° C. for at least 30 minutes in a waterbath. The photoactive polymer solution was made in 20 mM HEPES buffer, pH=8.0, which contained 5% PEG 1.1K-TA, 10% PEG 3.5K-Triol or PEG 4K-Diol, 100 mM TEoA, 32 mg/ml AMPS and 2 µl/ml NVP, and 13% Nycodenz. The suspension was transferred into a 10 ml beaker and the beaker was irradiated with an Argon laser at irradiance density of 200 $mW/cm^2$ for 1 minutes. The polymerization was quenched by adding 1-2 ml of M199 into the petri dish and the contents inside the beaker was transferred into a 50 ml conical tube containing 40 ml of M199. After washing with M199 three times, the encapsulated islets were put back into culture.

Implantation of Alginate Microcapsules and Alginate/PEG Microcapsules Containing Pig Islets as Xenografts into the Subcutaneous Site of Non-Diabetic Primates In a primate study, both alginate and alginate/PEG coated microcapsules were implanted into three, non-diabetic Cynomolgus primates. The PEG coated microcapsules were made under different conditions to vary their permselectivity. All of the implanted microcapsules (alginate alone & alginate/PEG) contained primary pig islets as a xenograft to the primate. These recipients were treated with an experimental anti-CD 154 monoclonal antibody. The subcutaneous implants were excised 7 days after implantation and the percentage of encapsulated porcine islets surviving in these different microcapsules was evaluated.

Figure 26:
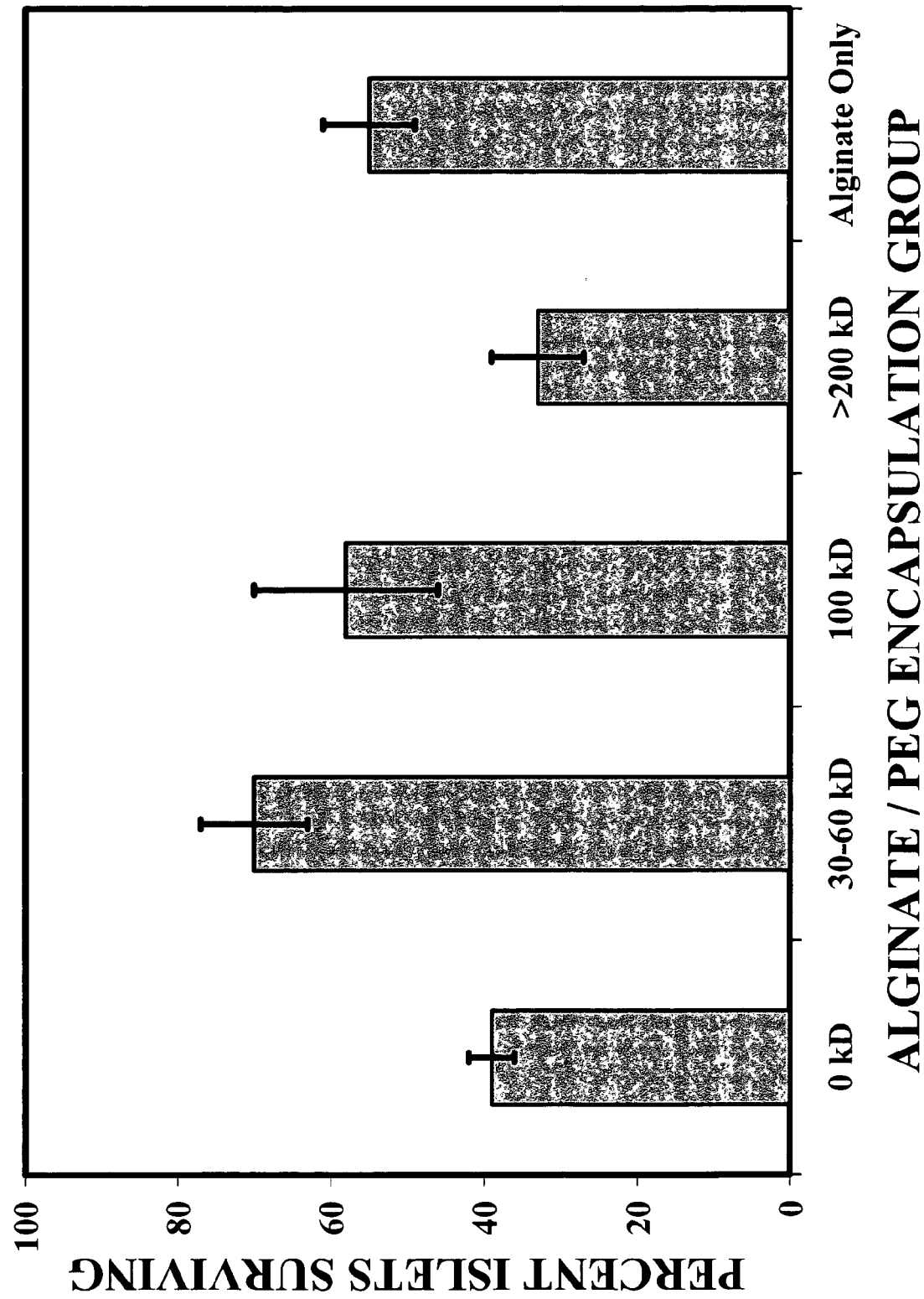
FIG. 26 shows the percent survival of porcine islets encapsulated in alginate only, as well as different configurations of alginate/PEG microcapsules, with different permselectivity profiles of the coatings after they had been implanted for 7 days into normal Cynomolgus primates. The different permselective values were 0 kD, 30-60 kD, 100 kD, and greater than 200 kD.

FIG. 26 illustrates the percent survival of porcine islets encapsulated in alginate only, as well as different configurations of alginate/PEG microcapsules, with different permselectivity profiles of the coatings after they have been implanted for 7 days into normal Cynomolgus primates. The different permselective values were 0 kD, 30-60 kD, 100 kD, and greater than 200 kD. The percent survival of porcine islets in the alginate only capsules was 55%. There was a difference in the percent islet survival between the alginate/PEG coated microcapsules. Survival at 24 hours was 37% for those that had very tight permselectivity (0 kD or <30 kD sized proteins) diffusion. Survival at 24 hours had increased to 70% for those that had permselectivity diffusion for 30-60 kD sized proteins. The microcapsules that permitted diffusion of <100 kD sized proteins had a survival at 24 hours of 58%. The microcapsules that were wide open (diffusion of >200 kD sized proteins) had a reduced islet survival at 24 hours of 32%.

Staining for Insulin and Glucagon in alginate/PEG encapsulated neonatal porcine islet tissue that had been implanted into the subcutaneous site of normal Cynomolgus primates for 7 days demonstrated the ability of alginate/PEG microcapsules to permit the survival of the encapsulated neonatal pig islet tissue for 7 days with the systemic delivery of low dose cyclosporine.

Figure 27:
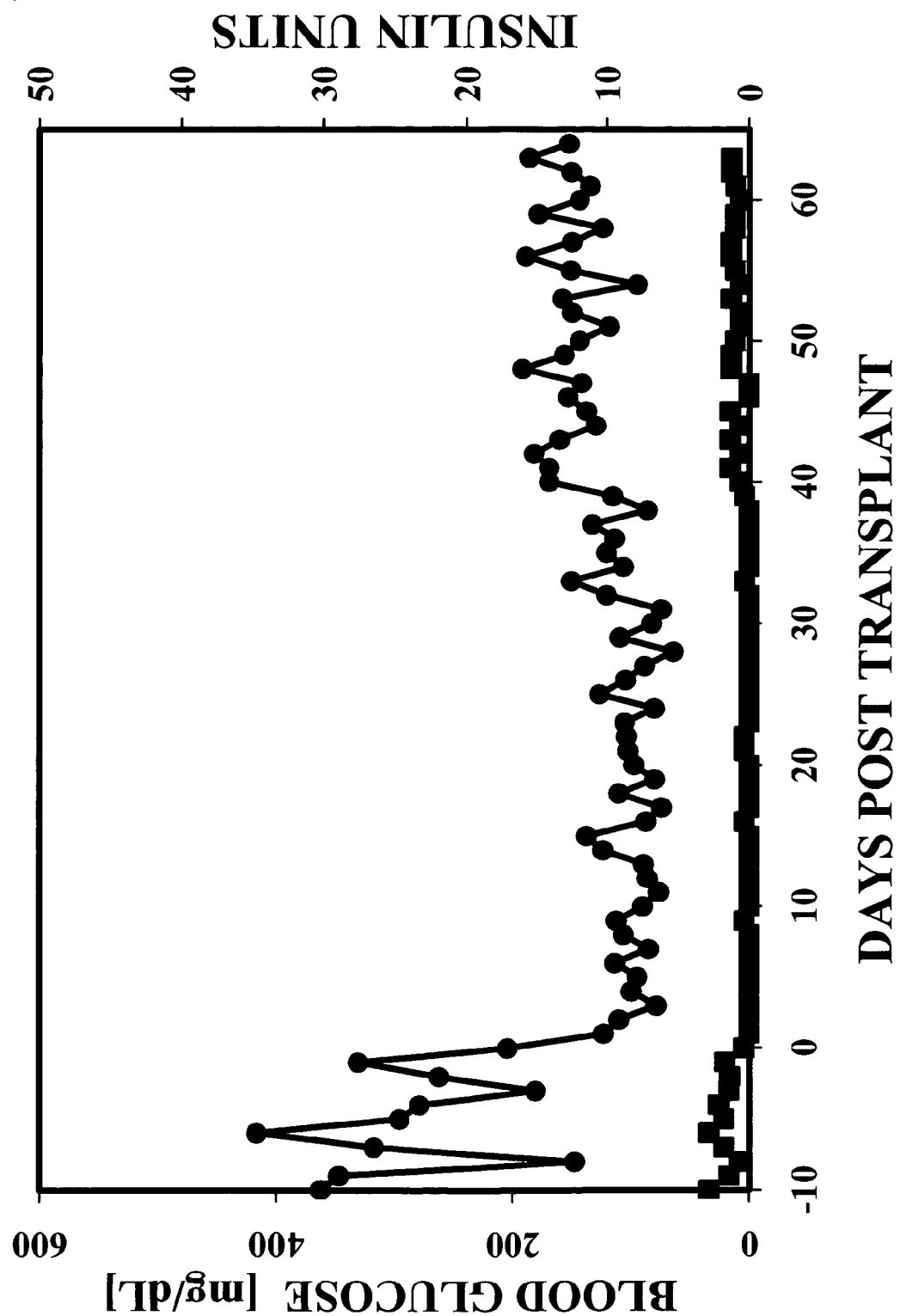
FIG. 27 presents the results of implanting alginate/PEG microcapsules encapsulated porcine islets that were implanted into the peritoneal cavity of a diabetic Cynomolgus primate that also received anti-CD154 antibody treatment for 30 days.

Implants of Alginate/PEG Microcapsule Encapsulation of Porcine Islet Xenografts into the Peritoneal Cavity of Diabetic Primates A follow-up study into diabetic primates demonstrated that porcine islets encapsulated in alginate/PEG microcapsules alleviated the insulin requirement for 30 days with the associated use of anti-CD154 systemic treatment. FIG. 27 illustrates the results of implanting alginate/PEG microcapsules encapsulating porcine islets into the peritoneal cavity of a diabetic Cynomolgus primate that also has received anti-CD154 antibody treatment for 30 days. The implanted islets were capable of maintaining normal blood glucose levels without insulin shots.

Producing Alginate/PEG Coated Microcapsules Containing Islets at Different Protein Permselectivity Islets were encapsulated in alginate/PEG microcapsules under different encapsulation conditions to alter the pore size within the coatings and placed into tissue culture. The encapsulated islets were treated with a detergent (SDS) to kill the encapsulated cells and to dissolve the proteins. These treated microcapsules were placed into culture medium without proteins and the media gathered at different times. The protein size was determined by placing the diffusates onto polyacrylamide gels and separating the different sizes of proteins under with PAGE electrophoresis. The results demonstrated that changing the concentrations of the PEG, the size of the PEG, the concentrations of the comonomers, the intensity of the laser, and the time of islet exposure were some of the many ways of changing the permselectivity of the PEG coating.

Figure 5:
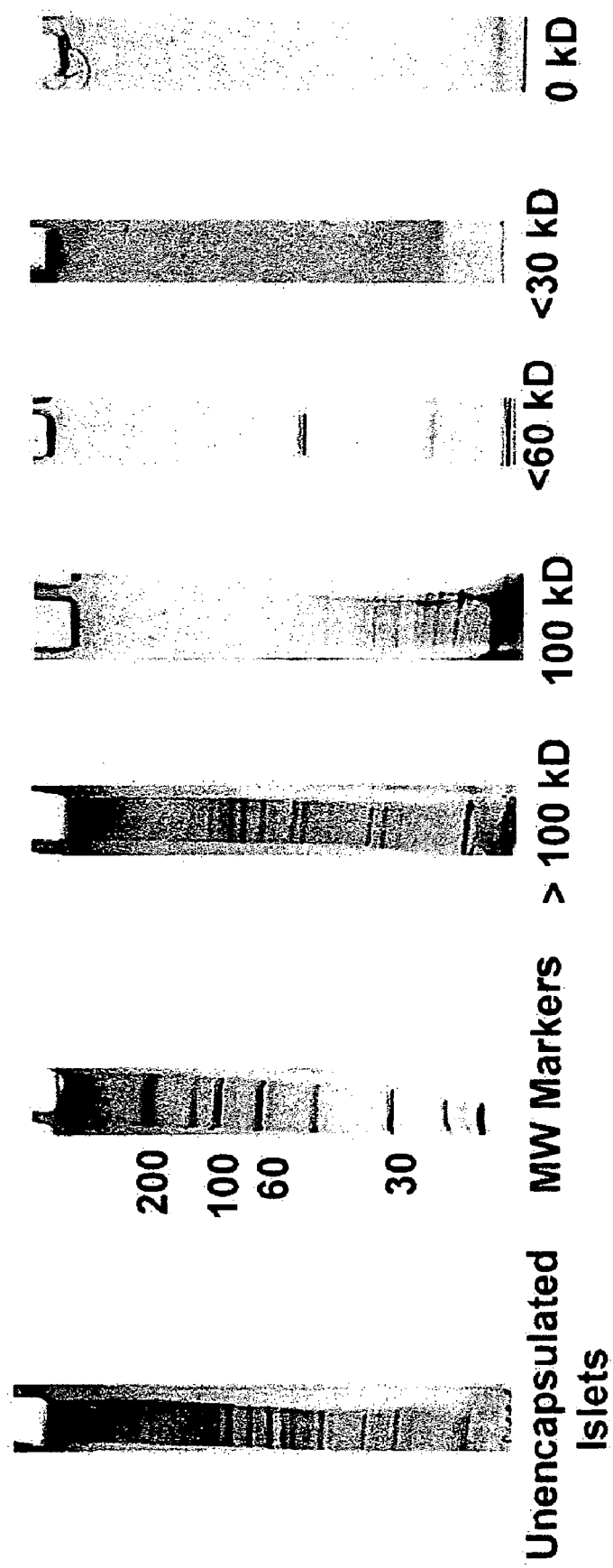
FIG. 5 shows the ability to alter the permselectivity profile of alginate/PEG microcapsules by altering the variables involved in the formation of the PEG coating. Alginate/PEG encapsulated islets were incubated over time and the proteins released from the cells were measured to determine the molecular weights. The proteins released from unencapsulated islets are shown in the left most row, followed by a column or molecular weight markers. The next columns show proteins released from alginate/PEG encapsulated islets, which released proteins of more than 100 kD, 100 kD, less than 60 kD, less than 30 kD, and 0 kD, respectively.

FIG. 5 illustrates the ability to alter the permselectivity profile of alginate/PEG microcapsules by altering the variables involved in the formation of the PEG coating. Alginate/PEG encapsulated islets were incubated and the proteins released from the cells over time were measured to determine the molecular weights. The proteins released from unencapsulated islets are shown in the far left row, followed by a column of molecular weight markers. The next columns show the proteins released from alginate/PEG encapsulated islets. The released proteins were more than 100 kD, 100 kD, less than 60 kD, less than 30 kD, and 0 kD, respectively.

Example 9

Alginate Encapsulation/PEG Coatings of Cell Types Other than Islets

In addition to islets, similarly aggregated cells were encapsulated in alginate microcapsules in a manner similar to Example 3, except that the cells were made into clusters prior to using the described technique for encapsulating islets in alginate microcapsules of different sizes. These methods were able to conformally coat an insulin producing tumor cell line, BHC8 mouse insulinoma cells with PEG. Also, using some types of cells that do not readily aggregate, cells were encapsulated first in the alginate capsule, even if they had not aggregated into cell clusters. This method was able to conformally coat cells from an insulin producing tumor cell line, rat insulinoma (RIN), with PEG.

Cells from the C-127 cell line, which have been engineered to produce ApoE2, were grown in an alginate matrix, rather than in clusters. Then the PEG coating was applied to these cells grown in the alginate matrix. Additionally is was possible to capture non-aggregating cells (CHO) in alginate microcapsules, which permitted them to expand within these alginate spheres in culture, and then coating them with PEG coatings, which completed the alginate/PEG coating.

Example 10

Formation of Alginate/PEG Coatings on Islets or Other Cells by the Use of Co-Extrusion of Alginate and PEG Polymer Mixes Either cell aggregates or single cells were mixed into an alginate solution that was loaded into one syringe in the syringe pump/argon jet system. The output of this syringe was connected to the inner #21-gauge needle of a coaxial needle system containing three needles. The second syringe contained only the PEG encapsulation mixture and was connected to the middle #18 gauge needle of the coaxial needle system. Argon gas was connected to the outer #16-gauge needle. The alginate syringe containing the cells and the PEG syringe were connected to the same pump so that the flow rates were identical from the two syringes. The amount of gas to form the droplets was set to control the droplet size. The resulting droplets from this two syringe/argon air jet were collected in a long glass column containing a non-aqueous solvent, such as oil, on the top ¾ and calcium or barium containing (80 mM) solution in the bottom ¼ of the column. The argon laser light was shone through the non-aqueous portion of the collecting column, which crosslinked the PEG outer coating prior to the encapsulated capsule falling through the non-aqueous portion of the collecting column. When the PEG crosslinked capsule containing the cells reached the bottom ¼ of the collecting column, the alginate in the core became crosslinked. The crosslinked alginate core/PEG coated capsules were collected from the bottom of the column and washed to remove the non-aqueous solvent. Additional PEG crosslinking was accomplished, when necessary, by exposing these capsules to additional argon laser light in the aqueous phase, in the presence of additional eosin y. The result of this example demonstrated 1] the ability to encapsulate single cells and 2] to provide a growth center within the PEG capsule that can permit the growth of new cells that are encapsulated. The examples using this type of coating were done with red blood cells (RBC's).

Encapsulation of Islets in PEG Microcapsules 500 islets suspended in M199 medium containing 10% fetal bovine serum were pelleted by centrifuging at 100 g for 3 min. The pellet was resuspended in 1 ml of a 10% w/v solution of PEG 3.5 KD triacrylate macromer in M199 medium containing eosin Y (1 mg/ml) vinyl pyrrolidone (16 mg/ml), and triethanolamine (100 mM). Mineral oil (20 ml) was then added to the tube which was vigorously agitated to form a dispersion of droplets 200-500 um in size. This dispersion was then exposed to an argon ion laser with a power of 200 mW/cm2, emitting at 514 nm, for 60 sec. The mineral oil was then separated by allowing the microcapsules to settle, and the resulting microcapsules were washed twice with PBS, once with hexane and finally thrice with media.

Example 11

Conformally Coating Islet Cells or Other Cells on Microbeads

One method of encapsulating cells that will not aggregate, and thus prevent the formation of a conformal coating, is to grow them on microcarrier beads. Following this growth, a similar PEG conformal coating technique as described in Example 2 for isolated islets was used to place PEG conformal coatings of these microcarrier beads containing the outer layers of the tumor cells. Conformal coatings were produced using this method and were shown to have acceptable viability. One would recognize that different types of microcarrier beads used to grow a variety of different cells on their surface would be successful in the conformally coating procedure described herein.

There are many different types of microcarrier beads produced for the purpose of growing cells on their surface. A C-127 cell line engineered to produce ApoE2 (previously presented in Example 7) did not aggregate but grew on Cytodex beads. These cells, including the microcarrier beads, were readily encapsulated using PEG conformal coatings directly on the outer surface of the carrier bead and the attached cells.

Example 12

Other Cell Types Encapsulated by PEG Conformal Coatings

Figure 28:
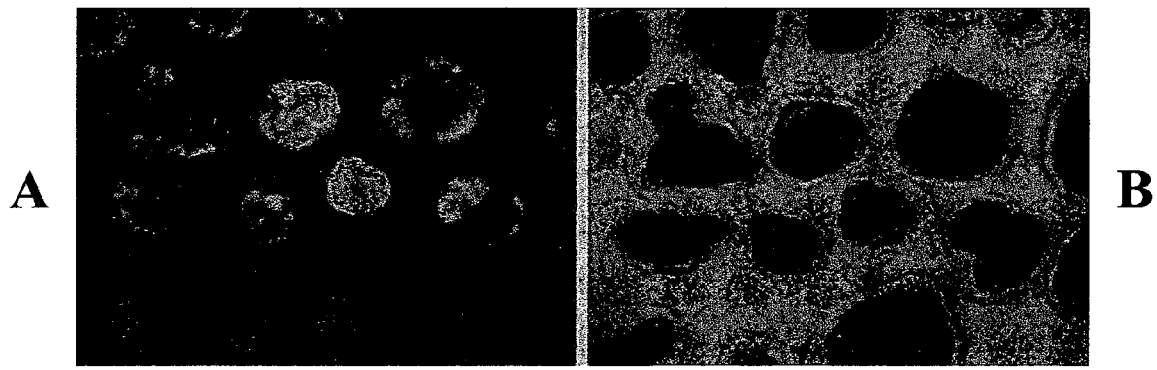
FIGS. 28A and B show using PEG conformal coating techniques to coat a different insulinoma tumor cell line (NIT) that will aggregate and demonstrating they can be maintained viable in tissue culture for 2 weeks. The coated cells are shown under normal light (FIG. 26A) and under fluorescent light with FDA/EB staining (FIG. 26B).
FIG. 28B shows human cells after 2 weeks of culture under normal light.
FIGS. 28C and 28D show mouse cells under fluorescent light with FDA/EB staining (89C) and normal light (89D).

Another cell type that can be aggregated and conformally coated with PEG includes the NIT, mouse insulinoma, cell line. The result of this is shown in FIG. 28 where thin conformal coatings have been applied by the techniques described above for islet cell aggregates and maintained viable in tissue culture for 2 weeks. After one week of culture, the encapsulated cells are clearly viable by staining with ethidium bromide/fluorescein diacetate staining. The coated cells are shown under normal light (FIG. 28A) and under fluorescent light with FDA/EB staining (FIG. 28B).

Figure 29:
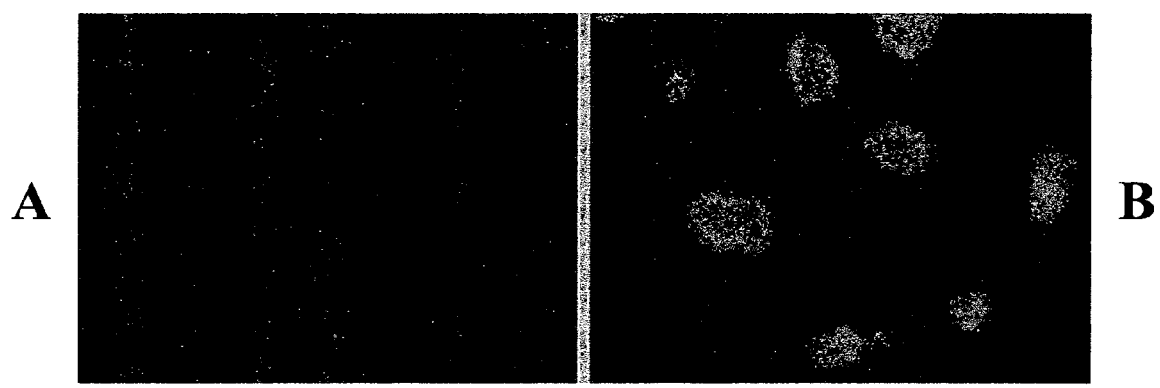
FIGS. 29A and B show conformally coating with PEG another cell line of monkey fetal lung cells that maintain viability after encapsulation.

A monkey kidney cell line was made to aggregate in tissue culture and then successfully conformally coated with PEG. FIG. 29A illustrates the cells under normal light and FIG. 29B illustrates the cells under fluorescent light with FDA/EB staining. Again, viability of these encapsulated tumor cells are demonstrated by FDA/EB staining.

Figure 30:
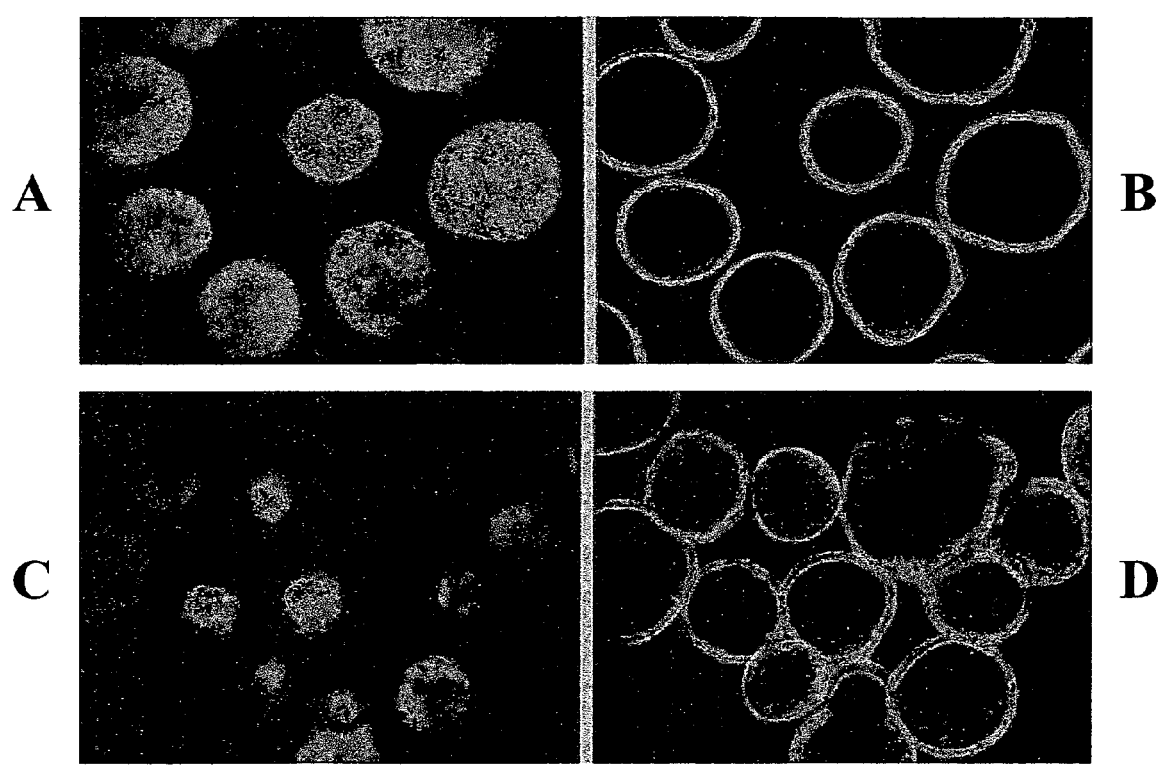
FIG. 30A-D show conformally coating with PEG cell aggregates produced from primary liver cells (hepatocytes) from both human and mouse origin and maintaining their viability for two weeks of culture.

In another example, primary cells other than pancreatic islet cells, were made to aggregate and then successfully conformally coated by PEG. FIG. 30 illustrates PEG conformally coating of cell aggregates produced from primary liver cells (hepatocytes) from both human and mouse origin, and maintaining their viability for two weeks of culture. FIG. 30A illustrates human cells after 2 weeks of culture under normal light. FIG. 30B illustrates human cells after 2 weeks of culture under fluorescent light with FDA/EB staining. FIG. 30C illustrates mouse cells under normal light and FIG. 30D illustrates the cells under fluorescent light with FDA/EB staining. Both human and mouse hepatocyte aggregates were successfully coated with PEG conformal coats and result in viable cells even after two weeks of culture.

Example 13

Estimating Curative Dose of Islets Encapsulated in Microcapsules or Conformally Coated Tables 3 and 4 provide data that may guide one of skill in the art to determine the curative dose of islets for a subject. The data below were calculated based on several assumptions: a] all microcapsules are spherical, b] 1,500 cells per islet, c] the minimum curative dose is 15,000 IEQ/kg of body weight, d] there are 5% empty microcapsules or 0% empty conformally-coated capsule e] maximum packing of microcapsule/conformal-coated capsules is 75% of the total volume, and f] each microcapsule/conformal-coated capsules contains one islet with a diameter of 150 μm. The maximum density of cells, $8.2 \times 10^8$ cells/ml, would be obtained by conformally coating islets with an 1 μm capsule.

The volumes do not account for the volume of suspension liquid or matrix. One of skill in the art would recognize that the data below might be used as guidance in calculating a curative dose, however the numbers below are not meant to be limiting on the range of number and concentration of islets that may be used. The assumptions made in making these calculations are not limiting on the invention. These numbers simply pertain to embodiments of the invention. (V islets (ml)=0.0264938)

TABLE 3

Islets encapsulated in Microcapsules

| Diameter of Microcapsule [μm] | Volume of Microcapsule [ml × 10⁻⁶] | Volume of Islet [ml × 10⁻⁶] | Volume ratio of microcapsule to islet | islets/ml | Curative Dose [ml/kg] | Curative Dose [ml per 100 kg person] | Cell Density Pancreatic islet cells [10⁶/ml] |
|---|---|---|---|---|---|---|---|
| 1000 | 523.60 | 1.77 | 296 | 1,910 | 7.8540 | 785 | 2.0 |
| 900 | 381.70 | 1.77 | 216 | 2,620 | 5.7256 | 573 | 2.8 |
| 800 | 268.08 | 1.77 | 151 | 3,730 | 4.0212 | 402 | 4.0 |
| 700 | 179.59 | 1.77 | 101 | 5,568 | 2.6939 | 269 | 6.0 |
| 600 | 113.10 | 1.77 | 64 | 8,842 | 1.6965 | 170 | 9.4 |
| 500 | 65.45 | 1.77 | 37 | 15,279 | 0.9817 | 98 | 16.3 |
| 400 | 33.51 | 1.77 | 19 | 29,842 | 0.5027 | 50 | 31.9 |
| 300 | 14.14 | 1.77 | 8 | 70,736 | 0.2121 | 21 | 75.6 |
| 200 | 4.19 | 1.77 | 2 | 238,732 | 0.0628 | 6 | 255.1 |

TABLE 4

Conformal-Coated Islets

| Thickness of Coating [μm] | Volume of Microcapsule [ml × 10⁻⁶] | Volume of Islet [ml × 10⁻⁶] | Volume ratio of microcapsule to islet | islets/ml | Curative Dose [ml/kg] | Curative Dose [ml per 100 kg person] | Cell Density Pancreatic islet cells [10⁶/ml] |
|---|---|---|---|---|---|---|---|
| 400 | 448.92 | 1.77 | 254 | 2,228 | 6.7338 | 673 | 2.5 |
| 350 | 321.56 | 1.77 | 182 | 3,110 | 4.8233 | 482 | 3.5 |
| 300 | 220.89 | 1.77 | 125 | 4,527 | 3.3134 | 331 | 5.1 |
| 250 | 143.79 | 1.77 | 81 | 6,954 | 2.1569 | 216 | 7.8 |
| 200 | 87.11 | 1.77 | 49 | 11,479 | 1.3067 | 131 | 12.9 |
| 150 | 47.71 | 1.77 | 27 | 20,959 | 0.7157 | 72 | 23.6 |
| 100 | 22.45 | 1.77 | 13 | 44,545 | 0.3367 | 34 | 50.1 |
| 75 | 14.14 | 1.77 | 8 | 70,736 | 0.2121 | 21 | 79.6 |
| 50 | 8.18 | 1.77 | 5 | 122,231 | 0.1227 | 12 | 137.5 |
| 25 | 4.19 | 1.77 | 2 | 238,732 | 0.0628 | 6 | 268.6 |
| 10 | 2.57 | 1.77 | 1 | 388,736 | 0.0386 | 4 | 437.3 |

Estimating Number of Cells Encapsulated in Microcapsules or Conformally Coated

Tables 5 and 6 provide data that may guide one of skill in the art to determine the curative dose of cells needed for a subject with various diseases and disorders. The data below were calculated based on several assumptions: a] the cells encapsulated or conformally-coated have an average diameter of 50 μm, b] the total volume of the cell aggregate in each microcapsule is 1.77×10-6 ml, c] there are 5% empty microcapsules or 0% conformal-coated capsules, d] maximum packing of microcapsules/conformal-coated capsules is 75% of the total volume, and e] each microcapsule/conformal-coated capsules contains one islet with a diameter of 150 μm. The maximum density of cells, $1.36 \times 10^7$ cells/ml, would be obtained by conformally coating islets with an 1 μm capsule.

The volumes do not account for the volume of suspension liquid or matrix. One of skill in the art would recognize that the data below might be used as guidance in calculating a curative dose, however the numbers below are not meant to be limiting on the range of number and concentration of cells that may be used. The assumptions made in making these calculations are not limiting on the invention. These numbers simply pertain to embodiments of the invention.

TABLE 5

Cells encapsulated in Microcapsules

| Diameter of Microcapsule [μm] | Volume of Microcapsule [ml × 10⁻⁶] | Volume of Cells [ml × 10⁻⁶] | Volume ratio of microcapsule to Cells | Cell Density (Average Human cell) [10³/ml] |
|---|---|---|---|---|
| 1000 | 523.60 | 1.77 | 296 | 34.0 |
| 900 | 381.70 | 1.77 | 216 | 46.7 |
| 800 | 268.08 | 1.77 | 151 | 66.4 |
| 700 | 179.59 | 1.77 | 101 | 99.2 |
| 600 | 113.10 | 1.77 | 64 | 157.5 |
| 500 | 65.45 | 1.77 | 37 | 272.2 |
| 400 | 33.51 | 1.77 | 19 | 531.6 |
| 300 | 14.14 | 1.77 | 8 | 1,260.0 |
| 200 | 4.19 | 1.77 | 2 | 4,252.4 |

TABLE 6

Conformal-Coated Cells

| Thickness of Coating [μm] | Volume of Microcapsule [ml × 10⁻⁶] | Volume of Cells [ml × 10⁻⁶] | Volume ratio of microcapsule to Cells | Cell Density (Average Human cell) [10³/ml] |
|---|---|---|---|---|
| 400 | 448.92 | 1.77 | 254 | 41.8 |
| 350 | 321.56 | 1.77 | 182 | 58.3 |
| 300 | 220.89 | 1.77 | 125 | 84.9 |
| 250 | 143.79 | 1.77 | 81 | 130.4 |
| 200 | 87.11 | 1.77 | 49 | 215.2 |
| 150 | 47.71 | 1.77 | 27 | 393.0 |
| 100 | 22.45 | 1.77 | 13 | 835.2 |
| 75 | 14.14 | 1.77 | 8 | 1,326.3 |
| 50 | 8.18 | 1.77 | 5 | 2,291.8 |
| 25 | 4.19 | 1.77 | 2 | 4,476.2 |
| 10 | 2.57 | 1.77 | 1 | 7,288.8 |

Example 14

Characteristics of the Alginate/PEG Microcapsules

Many different types, lengths, and sizes of PEG acrylates were tested in animals to determine biocompatibility and permselectivity of the composition, and the resulting functionality and viability of encapsulated cells after encapsulation. One of the acrylated PEG coatings was 1.1 kD PEG triacrylate. This very short PEG acrylate has unique biocompatibility properties when crosslinked.

The hydrogel encapsulated alginate beads were implanted into both normal small and large animals for a period of 14 days during which no immunosuppression was used. The capsules were then explanted, and the nature and extent of the tissue response towards these capsules were evaluated histologically. Minimal to no tissue reactions were noted on the examined samples, indicating these hydrogel compositions had a very good biocompatibility in vivo.

Figure 31:
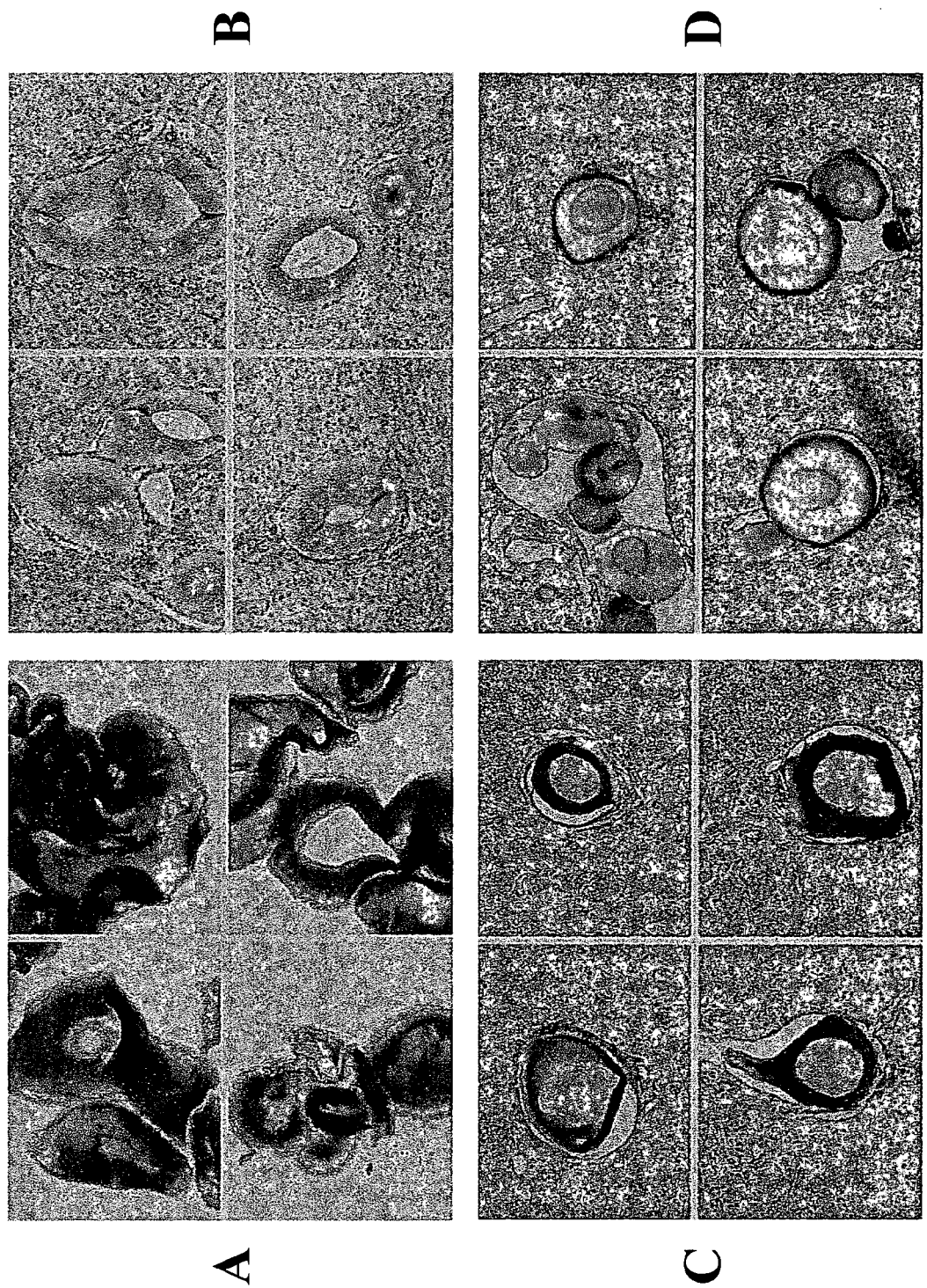
FIG. 31A-D show biocompatibility reactions in four different species (91A—IP in mouse, 91B—PV in pig, 91C—PV in dog and 91D—PV in primate) that have empty alginate/PEG microcapsules implanted at different sites. This figure shows the results of injecting the empty alginate microcapsules coated with 1.1 kD PEG triacrylate when they were injected into the portal vein to the liver.

FIG. 31 shows the biocompatibility reactions in mice, pig, dog, and primate, which have had empty alginate/PEG microcapsules implanted at different sites. Empty alginate microcapsules coated with 1.1 kD PEG triacrylate were injected into the hepatic portal vein. In the pig and primate, there is no reaction to these empty PEG microcapsules after two weeks following implant. The dog showed the most reactivity of all the PEG's injected, but still had very few cells of reactivity.

The composition of the encapsulating material was evaluated and scored to assess biocompatibility, permselectivity, functionality and viability. A scoring system (1 to 4) was used to quantify the response of the animal to implantation with encapsulated cells.

Figure 32:
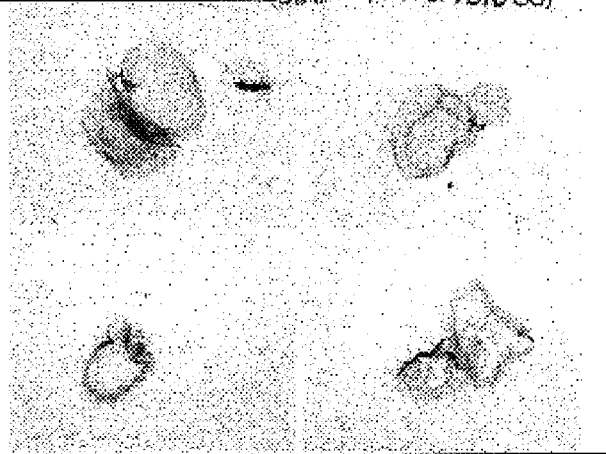
FIG. 32 shows the biocompatibility of encapsulated cells in small animals with representative histology of score values 1, 2, and 3.
Figure 33:
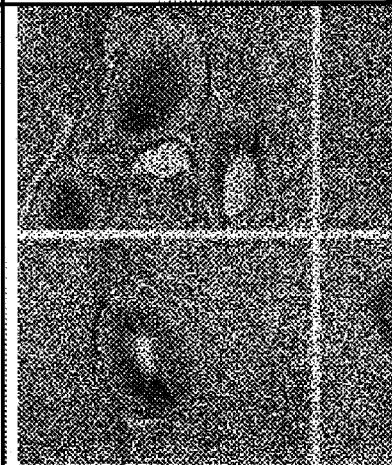
FIG. 33 shows the biocompatibility of encapsulated cells in large animals with representative histology of score values 1, 2, and 4.
Figure 33:
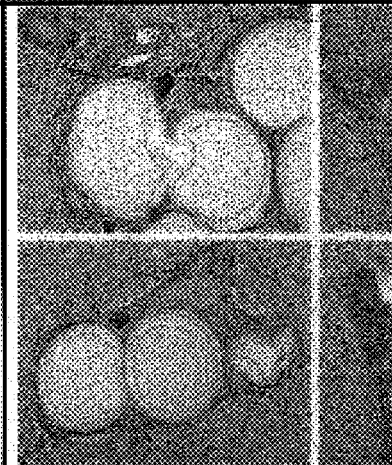
Figure 33:

Table 7 shows the scoring values for the presence of macrophages, FB giant cell, inflammatory response, lymphocytes, and eosinophils. The overall score for biocompatibility is the average score of these five categories. FIG. 32 illustrates the biocompatibility of encapsulated cells in small animals by showing representative histology of score values 1, 2, and 3. FIG. 33 illustrates the biocompatibility of encapsulated cells in large animals by showing representative histology of score values 1, 2, and 4.

TABLE 7

| Score | Macrophages | FB Giant Cell | Inflammatory Response | Lymphocytes | Eosinophils |
|---|---|---|---|---|---|
| 1 | none to minimal | none | none | none | none |
| 2 | mixed activity | scattered, <50% | minimal | few scattered | few scattered |
| 3 | activated, some stacking | >50% | moderate | moderate | moderate |
| 4 | palisading | foamy | extensive | extensive | extensive |

Table 8 shows how the permselectivity can be engineered by changing the ingredients and percentages of the ingredients in the composition. A combination of 10% 3.5K-TA and 10% 10K-TA makes the gel structure very tight and prevents the passage of almost all proteins between the blood and encapsulated cells. If the composition is changed to 5% 3.5K-TA and 5% 8K-DA the gel structure allows medium size (100 to 60 kD) proteins to pass between the blood and encapsulated cells. A composition of 20% 10K-TA produces a gel that allows large molecular weight (>100 kD) proteins to pass between the blood and encapsulated cells.

TABLE 8

| Composition | >100K | <100K | <60K | <30K | <18K | No Bands |
|---|---|---|---|---|---|---|
| 10% 3.5K-TA + 10% 10K-TA | 0 | 0 | 0 | 0 | 0 | 100 |

TABLE 8-continued

| Composition | >100K | <100K | <60K | <30K | <18K | No Bands |
|---|---|---|---|---|---|---|
| 5% 3.5K-TA + | 0 | 0 | 100 | 0 | 0 | 0 |
| 5% 8K-DA | 0 | 11 | 88 | 0 | 0 | 0 |
| 20% 10K-TA | 75 | 25 | 0 | 0 | 0 | 0 |
|  | 100 | 0 | 0 | 0 | 0 | 0 |
|  | 88 | 0 | 12 | 0 | 0 | 0 |

Figure 34:
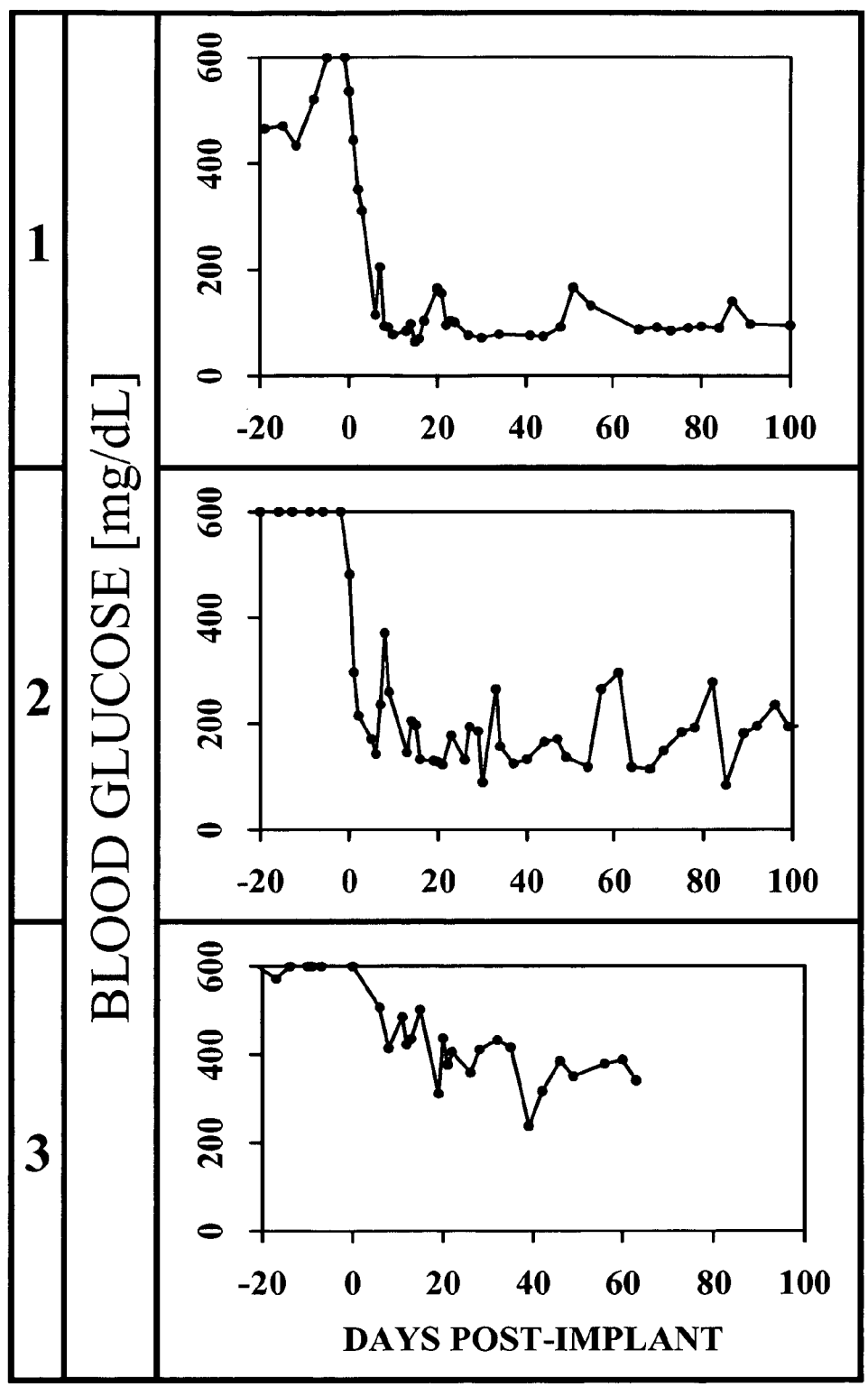
FIG. 34 shows the functionality of the encapsulated islets implanted into a streptozotocin-induced diabetic athymic mouse with representative score values 1, 2, and 3.

The composition of the encapsulating material has a great effect on the resulting functionality and viability of the encapsulated cells. The chemicals and methods used to make the gel can be cytotoxic or damaging to the cell. FIG. 34 illustrates the results of implanting encapsulated islets into a streptozotocin-induced diabetic athymic mouse. A score of "1" represents encapsulated cells that eliminate diabetes and a blood glucose level of <150 ng/ml, "2" represents encapsulated cells that reduce the diabetes but are unable to maintain homeostasis from day to day and a blood glucose level of between 150 and 300 ng/ml, and "3" represents encapsulated cells that are unable to control the diabetes and a blood glucose level of >300 ng/ml.

Figure 6:
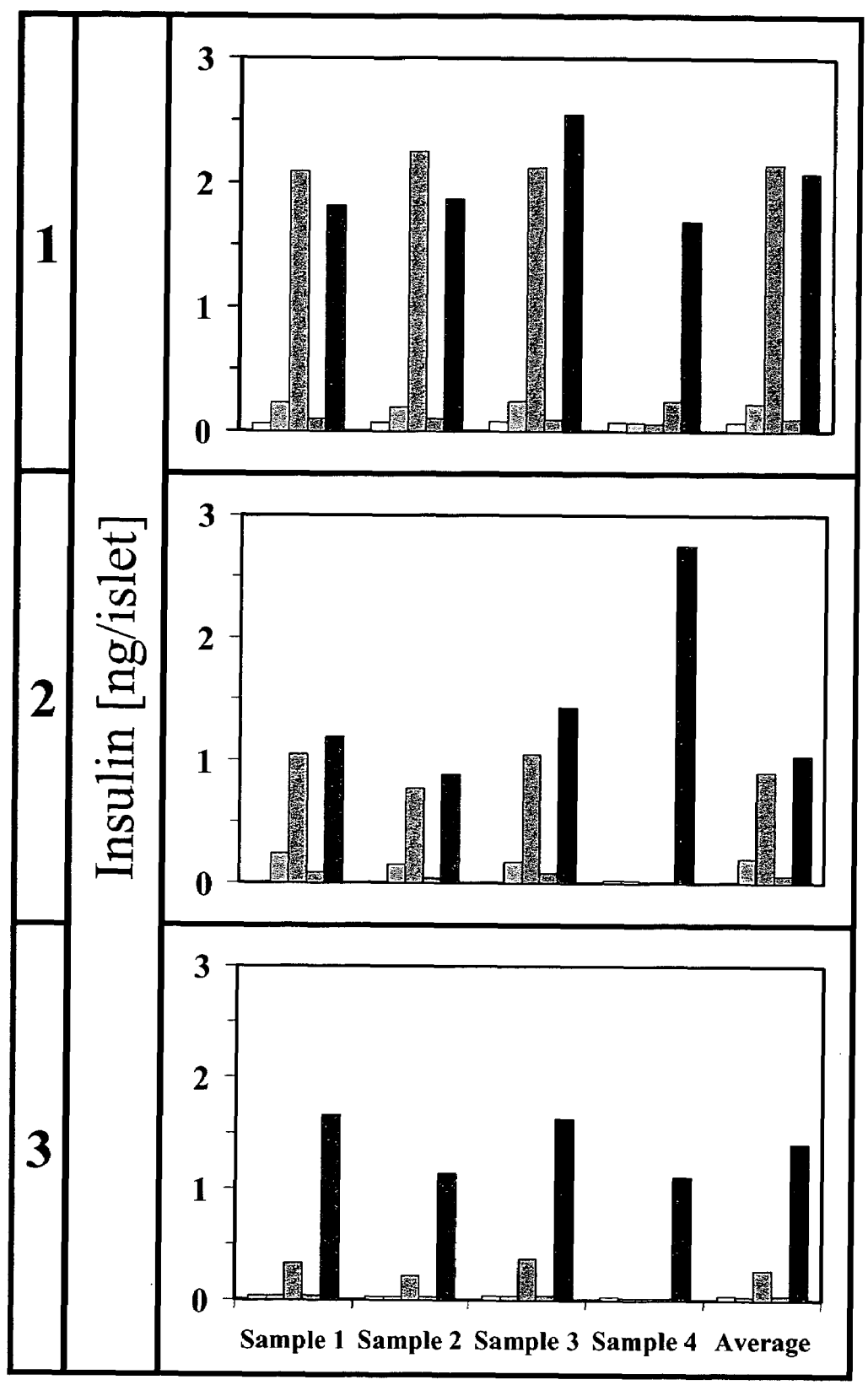
FIG. 6 shows the functionality of the encapsulated islets with the Static Glucose Stimulation test with different representative protein diffusivity profiles scored with open coatings (>200 kD) as "1", intermediate (100-200 kD) as "2", and tight (<100 kD) as "3".

The functionality of the encapsulated cells also can be assessed with a Static Glucose Stimulation test. The test compares the insulin production between Basal production with a low concentration of glucose compared to the insulin production with high glucose (Stimulation) and high glucose with IBMX. FIG. 6 illustrates the scoring of the Static Glucose Stimulation test. A score of "1" represents a Stimulation insulin production >2 times Basal and IBMX insulin production >10 times Basal. A score of "2" represents a Stimulation insulin production 1.5 to 2 times Basal and TBMX insulin production 5 to 10 times Basal. A score of "3" represents a Stimulation insulin production <1.5 times Basal and IBMX insulin production <5 times Basal.

Figure 4:
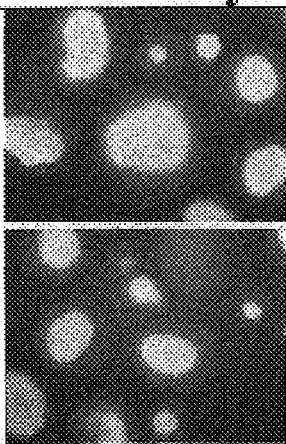
FIG. 4 shows the viability of the encapsulated cells as measured by an FDA/EB test with scores of 1, 2, and 4.

The viability of the cells was assessed the encapsulation process. The scoring system ranks the viability as "1"=>90%, "2"=<90% to 75%, "3"=<75% to 50%, "3"=<50% to 25%, and "4"=<25%. FIG. 4 illustrates the viability and histology of the encapsulated cells with scores of 1, 2, and 4.

Example 15

Ischemic Muscle Implants Using Genetically Engineered Cells Producing Angiogenic Growth Factors that are Conformally Coated with PEG Coatings Many different cell types can be genetically engineered to produce different angiogenic growth factors. These cells are human or animal fibroblasts, vascular cells, or various non-tumorigenic cell lines. The choices of angiogenic growth factors, such as VEGF, bFGF, and PDGF, are made to use as the genetically engineered cell line for encapsulation. Outcome measurements required before considering implantation into animal models with ischemic muscles are the release of the chosen angiogenic growth factor at a level presumed to provide a clinical response in the microenvironment of the ischemic muscle. If the cells were made to aggregate, then conformal coatings of these cell aggregates was done using the similar conditions to those described in Example 2. Implantation of these encapsulated angiogenic growth factor producing cells were made in rodent models with either experimentally induced ischemic myocardium or experimentally induced ischemic limb muscles. Outcome measurements were histologic demonstration of increased muscle mass and functional evidence of increased exertion of the ischemic muscle selected including cardiac muscle. Implants of these angiogenic growth factor producing cells in larger animals including humans was accomplished through vascular access and fluoroscopic control permitting direct injection in the myocardium, for example, without the need for any open surgical procedure.

Example 16

Splenic Implants of PEG Conformally Coated Islets, Hepatocytes, or Genetically Engineered Cells for the Treatment of Different Diseases In the case of islets, unencapsulated islets have been implanted successfully in the spleens of diabetic dogs, as well as diabetic humans, and successfully reversed their diabetes in a similar manner compared with intrahepatic unencapsulated islet implants. Now encapsulating islets permits their successful function in the spleen and in the subcutaneous site. Similarly, implanting genetically engineered cells, such as hepatocytes, into the spleen provides the cells a well-vascularized site as well as one in which the genetically engineered product is first released to the liver. This is important in those diseases in which the liver has a major role in handling or utilizing the genetically engineered cell product that is being implanted in the spleen. The ready access to the spleen and its capacity to hold volumes of cells makes it an attractive site for encapsulated cell therapy.

Example 17

Intrathecal Injection of Encapsulated Cells for Delivering CNS Agents for the Treatment of Diseases or Disorders A number of different CNS diseases are treated by encapsulated cells. Some may require direct injection into a specific location of the diseased brain, such as injecting encapsulated dopamine producing cells into the substantia nigra of patients with Parkinsonism. However, many different CNS diseases or disorders are treated by simply injecting the encapsulated cells producing the CNS factor required into the spinal fluid along the spinal cord or below it, permitting the release of the encapsulated cell product. Circulation of the spinal fluid carries the product to the desired location of the brain or spinal cord involved. A further example of this approach was shown by encapsulating dopamine producing cells in hollow fibers which were inserted into the lumbar spinal canal for the treatment of chronic pain conditions, such as those encountered in metastatic cancer patients. Using these conformal coatings permitted large quantities of cells to be delivered. Another application is to contain these encapsulated cells within hollow tubes that can be tethered to the outside, but not relying on these tubes for any immunoprotection. One such disease is Multiple Sclerosis, which is treated by encapsulating oligodendricytes or other cells making other factors known to make substances needed to repair the myelin damage from the disease. Another example is the treatment of pain where this form of encapsulation increases the amount of cells producing dopamine. The use of dopamine is also helpful in treating different forms of drug and alcohol addiction by increasing the level of dopamine circulating in the spinal fluid of dependent patients. The use of NGF (Nerve Growth Factor) and other agents is helpful in treating patients with spinal cord injuries. The NGF or other agent is released from the encapsulated cells in the spinal fluid of the spinal canal.

Example 18

Implantation of Encapsulated Parathyroid or Adrenal Cells into Muscle, Spleen, or Liver of Patients without the Function of Their Own Parathyroid or Adrenal Cells Due to Disease or Surgical Removal from Actual Tumors or Potential Tumor Risks A number patients have their parathyroids or their adrenal glands removed for actual tumors. A second group of patients has these organs removed for the risk of future tumor formation due to genetic diseases that are inheritable. PEG encapsulation of normal human parathyroid or adrenal cells from cadaver organ donors were done with removal of these tissues at the time of organ donation. These organs have had a number of cell preparations made from them for experimental work and one skilled in the art can readily prepare cells from these organs. PEG encapsulation is accomplished by conformal coating or by alginate based PEG coatings for implanting these encapsulated cells into these patients who have lost the function of one of these organs through actual tumors or potential tumor formation.

Example 19

Implantation of Encapsulated Cells for the Treatment for Genetically Inherited Diseases There are many human and animal diseases caused by genetic defects. The role of gene therapy in directly injecting these genes in the different tissues of the body has not been safely developed at this time. Many of these inherited diseases are treated by encapsulated cells producing the missing gene product using primary cells making the product or using genetically engineered cells making the product. Encapsulation of these cells may be performed by the techniques described elsewhere in the specification. Implantation of these encapsulated cells may be done in most any site if the location of the product is not required in a specific site. Thus, encapsulated cells are injected subcutaneously, in the liver by portal vein injection or by direct injection, in the spleen by vascular or direct injection, in the muscle by vascular or direct injection, in the kidney by vascular or direct injection, in the heart by vascular or direct injection, in the spinal canal by injection, in the brain by vascular or direct injection, in the eye by vascular or direct injection, in the lung by vascular or direct injection, in the thyroid by vascular or direct injection, in the bone marrow by direct injection, in any joint by direct injection, or directly into any wound by direct injection or application.

Example 20

The Use of Encapsulated Cells Producing Growth Hormone for Use in Farm or Production Animals to Increase the Rate of Growth or the Production of Milk Growth hormone is being used in dairy cattle to increase the production of milk. It has also been suggested to be useful for injecting into porcine weanlings to increase their meat production and size, and thus decrease the time to market. Encapsulating growth hormone producing cells and implanting them into these production animals accomplishes the same results without the need for daily expensive injections. In the case of the porcine model, the PEG coating may be engineered in a manner allowing it to biodegrade in 6 weeks so that the animal would be free of the growth hormone at the time of slaughter and following human consumption of the meat. Alternatively, the encapsulated cells are contained in a readily removable insertion container to eliminate the production of growth hormone.

It is to be understood that the foregoing description is exemplary and explanatory in nature, and is intended to illustrate the invention and its preferred embodiments. Through routine experimentation, the artisan will recognize apparent modifications and variations that may be made without departing from the spirit of the invention. Therefore, it should be clearly understood that the forms of the present invention are illustrative only and are not intended to limit the scope of the present invention. All references cited herein are hereby expressly incorporated by reference.

What is claimed is:

1. A composition comprising:
    encapsulating devices comprising a conformal coating, and
    cell aggregates,
   wherein said composition has a cell density of at least about 100,000 cells/ml, wherein the conformal coating for the encapsulating devices comprises a polymerizable high density ethylenically unsaturated PEG having a molecular weight between 900 and 3,000 Daltons, and a sulfonated comonomer, and wherein the coating conforms to the size and shape of the cell aggregates.

2. The composition of claim 1, wherein the encapsulating devices are microcapsules.

3. The composition of claim 2, wherein the microcapsules are conformally coated cell aggregates.

4. The composition of claim 3, wherein the cell aggregates are pancreatic islets.

5. The composition of claim 4, wherein the cell density is at least about 6,000,000 cells/ml.

6. The composition of claim 1, where the cell is selected from the group consisting of neurologic, cardiovascular, hepatic, endocrine, skin, hematopoietic, immune, neurosecretory, metabolic, systemic, and genetic.

7. The composition of claim 6, where the cell is selected from the group consisting of autologous, allogeneic, xenogeneic and genetically-modified.

8. The composition of claim 7, where the endocrine cell is an insulin producing cell.

9. A composition comprising a plurality of encapsulating devices having an average diameter of less than 400 µm, said encapsulating devices comprising encapsulated cells aggregates conformally coated in an encapsulation material, wherein the composition comprises at least about 500,000 cells/ml and wherein the encapsulation material comprises a polymerizable high density ethylenically unsaturated PEG having a molecular weight of between 900 and 3,000 Daltons, and a sulfonated comonomer, wherein the coating conforms to the size and shape of the cell aggregates.

10. The composition of claim 9, wherein the average diameter of the encapsulating device is less than 300 micron.

11. The composition of claim 9, wherein the average diameter of the encapsulating device is less than 200 micron.

12. The composition of claim 9, wherein the average diameter of the encapsulating device is less than 100 micron.

13. The composition of claim 9, wherein the average diameter of the encapsulating device is less than 50 micron.

14. A composition comprising a plurality of encapsulating devices having an average diameter of less than 400 µm, said encapsulating devices comprising encapsulated cells aggregates conformally coated in an encapsulation material, wherein the composition comprises a ratio of volume of encapsulating device to volume of cells of less than about 20:1 and wherein the encapsulation material comprises a polymerizable high density ethylenically unsaturated PEG having a molecular weight between 900 and 3,000 Daltons, and a sulfonated comonomer, and wherein the encapsulation material conforms to the size and shape of the cell aggregates.

15. The composition of claim 14, wherein the composition comprises a ratio of volume of encapsulating device to volume of cells of less than about 10:1.

16. The composition of claim 14, wherein the composition comprises a ratio of volume of encapsulating device to volume of cells of less than about 2:1.

17. The composition of any one of claims 1, 9, or 14, where the polymerizable high density ethylenically unsaturated PEG is a high density acrylated PEG.

18. The composition of claim 17, where the polymerizable high density acrylated PEG has a molecular weight of 1.1 kD.

19. The composition of any one of claims 1, 9, or 14, where the sulfonated comonomer is selected from the group consisting of 2-acrylamido-2-methyl-1-propanesulfonic acid, vinylsulfonic acid, 4-styrenesulfonic acid, 3-sulfopropyl acrylate, 3-sulfopropyl methacrylate, and n-vinyl maleimide sulfonate.

20. The composition of claim 19, where the sulfonated comonomer is 2-acrylamido-2-methyl-1-propanesulfonic acid.

21. The composition of any one of claims 1, 9, or 14, further comprising a cocatalyst selected from the group consisting of triethanolamine, triethylamine, ethanolamine, N-methyl diethanolamine, N,N-dimethyl benzylamine, dibenzyl amino, N-benzyl ethanolamine, N-isopropyl benzylamine, tetramethyl ethylenediamine, potassium persulfate, tetramethyl ethylenediamine, lysine, omithine, histidine and arginine.

22. The composition of claim 21, where the cocatalyst is triethanolamine.

23. The composition of any one of claims 1, 9, or 14, further comprising an accelerator selected from the group consisting of N-vinyl pyrrolidinone, 2-vinyl pyridine, 1-vinyl imidazole, 9-vinyl carbazone, 9-vinyl carbozol, acrylic acid, n-vinylcarpolactam, 2-allyl-2-methyl-1,3-cyclopentane dione, and 2-hydroxyethyl acrylate.

24. The composition of claim 23, where the accelerator is N-vinyl pyrrolidinone.

25. A composition comprising encapsulating devices comprising encapsulating cells in an encapsulation material with a polyethylene glycol (PEG) coating having a molecular weight between 900 and 3,000 Daltons, wherein said composition has a cell density of at least about 6,000,000 cells/ml.

26. The composition of claim 25, wherein the encapsulating devices are microcapsules.

27. The composition of claim 26, wherein the microcapsules are conformally coated cell aggregates.

28. The composition of claim 27, wherein the cell aggregates are pancreatic islets.

29. The composition of claim 25, where the cell is selected from the group consisting of neurologic, cardiovascular, hepatic, endocrine, skin, hematopoietic, immune, neurosecretory, metabolic, systemic, and genetic.

30. The composition of claim 29, where the cell is selected from the group consisting of autologous, allogeneic, xenogeneic and genetically-modified.

31. The composition of claim 30, where the endocrine cell is an insulin producing cell.

32. A composition comprising a plurality of encapsulating devices having an average diameter of less than 400 μm, said encapsulating devices comprising encapsulated cells in an encapsulation material, wherein a cell density is at least about 6,000,000 cells/ml.

33. The composition of claim 32, wherein the average diameter of the encapsulating device is less than 300 micron.

34. The composition of claim 32, wherein the average diameter of the encapsulating device is less than 200 micron.

35. The composition of claim 32, wherein the average diameter of the encapsulating device is less than 100 micron.

36. The composition of claim 32, wherein the average diameter of the encapsulating device is less than 50 micron.

* * * * *

UNITED STATES PATENT AND TRADEMARK OFFICE
CERTIFICATE OF CORRECTION

PATENT NO. : 7,427,415 B2
APPLICATION NO. : 10/684859
DATED : September 23, 2008
INVENTOR(S) : Scharp et al.

It is certified that error appears in the above-identified patent and that said Letters Patent is hereby corrected as shown below:

Page 2, Column 2, Entry 5, (Foreign Patent Documents) "ES 210472T T3" should be changed to --ES 2104727T T3--

Page 2, Column 2, Line 58, (Other Publications) "Procine Pancreatic" should be changed to --Porcine Pancreatic--

Column 12, Line 51, "thoionine, riboflavin" should be changed to --thionine, riboflavin--

Column 13, Line 5, "omithine, histidine" should be changed to --ornithine, histidine--

Column 13, Line 58, "omithine, histidine" should be changed to --ornithine, histidine--

Column 15, Line 50, "at 285 days" should be changed to --at 285 days.--

Column 17, Line 67, "cells or tissue" should be changed to --cells or tissue.--

Column 21, Line 67, "loss of weight" should be changed to --loss of weight.--

Column 22, Line 2, "insulin granules" should be changed to --insulin granules.--

Column 29, Line 2, "omithine, histidine" should be changed to --ornithine, histidine--

UNITED STATES PATENT AND TRADEMARK OFFICE
CERTIFICATE OF CORRECTION

PATENT NO. : 7,427,415 B2
APPLICATION NO. : 10/684859
DATED : September 23, 2008
INVENTOR(S) : Scharp et al.

It is certified that error appears in the above-identified patent and that said Letters Patent is hereby corrected as shown below:

Column 31, Line 25, "CaC12 and" should be changed to --$CaCl_2$ and--

Column 34, Line 14, "post-implantation" should be changed to --post-implantation.--

Column 41, Line 21, "cylosporinen administration" should be changed to --cyclosporine administration--

Column 51, Line 33, "and TBMX insulin" should be changed to --and IBMX insulin--

Column 54, Line 45, "encapsulated cells" should be changed to --encapsulated cell--

Column 54, Line 50, "weight of between" should be changed to --weight between--

Column 55, Line 13, "the polymerizable" should be changed to --the covalently polymerizable--

Column 55, Line 33, "omithine, histidine" should be changed to --ornithine, histidine--

Column 56, Line 8, "a polyethylene" should be changed to --a covalently linked polyethylene--

Signed and Sealed this

Nineteenth Day of May, 2009

JOHN DOLL
*Acting Director of the United States Patent and Trademark Office*